(12) United States Patent
Utsunomiya et al.

(10) Patent No.: US 9,727,779 B2
(45) Date of Patent: Aug. 8, 2017

(54) MOTION INFORMATION PROCESSING APPARATUS

(71) Applicant: TOSHIBA MEDICAL SYSTEMS CORPORATION, Otawara-Shi (JP)

(72) Inventors: Kazuki Utsunomiya, Nasushiobara (JP); Kousuke Sakaue, Nasushiobara (JP); Satoshi Ikeda, Yaita (JP); Hayato Konishi, Sakura (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 55 days.

(21) Appl. No.: 14/804,493

(22) Filed: Jul. 21, 2015

(65) Prior Publication Data
US 2015/0324637 A1 Nov. 12, 2015

Related U.S. Application Data

(63) Continuation of application No. PCT/JP2014/051405, filed on Jan. 23, 2014.

(30) Foreign Application Priority Data

Jan. 23, 2013 (JP) ................ 2013-010524
Jan. 23, 2013 (JP) ................ 2013-010547
Oct. 28, 2013 (JP) ................ 2013-223470

(51) Int. Cl.
G06K 9/00 (2006.01)
A61B 5/11 (2006.01)
(Continued)

(52) U.S. Cl.
CPC .......... *G06K 9/00342* (2013.01); *A61B 5/11* (2013.01); *G06K 9/00348* (2013.01);
(Continued)

(58) Field of Classification Search
CPC ............... A61B 5/00; G06K 9/00; G06T 7/00
(Continued)

(56) References Cited

U.S. PATENT DOCUMENTS 8,345,919 B2 * 1/2013 Seo ................ G08B 13/19602
382/103
2005/0209052 A1 * 9/2005 Ashby ................ A63B 21/005
482/9
(Continued)

FOREIGN PATENT DOCUMENTS

JP 09-56697 A 3/1997
JP 2002-063579 A 2/2002
(Continued)

OTHER PUBLICATIONS

Ikezaki, R. et al., "Gait Analysis with a Mobile 16mm Movie Camera," *Japanese Journal of Rehabilitation Medicine*, vol. 12, No. 2, The Japanese Association of Rehabilitation Medicine, Jun. 18, 1975, pp. 109-113 with English Abstract.
(Continued)

*Primary Examiner* — Abolfazl Tabatabai
(74) *Attorney, Agent, or Firm* — Oblon, McClelland, Maier & Neustadt, L.L.P.

(57) ABSTRACT

A motion information processing apparatus according to an embodiment includes processing circuitry. The processing circuitry obtains pieces of motion information of a subject acquired from mutually-different positions with respect to the subject performing a predetermined motion. The processing circuitry calculates association information used for bringing the pieces of motion information obtained into association with one another. The processing circuitry exercises control so as to cause an output circuitry to output such output information in which the pieces of motion informa-
(Continued)

tion are kept in association with one another on the basis of the association information calculated.

23 Claims, 42 Drawing Sheets

(51) Int. Cl.
| | |
|---|---|
| *G06Q 50/24* | (2012.01) |
| *G06Q 10/06* | (2012.01) |
| *G06T 7/246* | (2017.01) |
| *G06T 7/292* | (2017.01) |
| *H04N 7/18* | (2006.01) |

(52) U.S. Cl.
CPC ............ *G06Q 10/06* (2013.01); *G06Q 50/24* (2013.01); *G06T 7/248* (2017.01); *G06T 7/292* (2017.01); *A61B 2576/00* (2013.01); *G06T 2207/10024* (2013.01); *G06T 2207/30196* (2013.01)

(58) Field of Classification Search
USPC ........ 382/103, 107, 236; 348/154, 155, 169, 348/170, 171, 172, 352
See application file for complete search history.

(56) References Cited

U.S. PATENT DOCUMENTS

| | | |
|---|---|---|
| 2006/0280333 A1 | 12/2006 | Ikeda et al. |
| 2009/0262006 A1* | 10/2009 | McNeill .................. G01S 7/35 342/22 |

FOREIGN PATENT DOCUMENTS

| | | |
|---|---|---|
| JP | 2002-143112 A | 5/2002 |
| JP | 2006-350578 A | 12/2006 |
| JP | 2007-236663 A | 9/2007 |
| JP | 2010-131085 A | 6/2010 |
| JP | 2012-157580 A | 8/2012 |
| WO | WO 2008/026357 A1 | 3/2008 |

OTHER PUBLICATIONS

International Search Report issued Apr. 22, 2014 for PCT/JP2014/051405 filed on Jan. 23, 2014 with English Translation.
Written Opinion issued Apr. 22, 2014 for PCT/JP2014/051405 filed on Jan. 23, 2014.

* cited by examiner

FIG.4

| JOINT IDENTIFICATION INFORMATION | COORDINATE INFORMATION |
|---|---|
| 2a | (x1, y1, z1) |
| 2b | (x2, y2, z2) |
| 2c | (x3, y3, z3) |
| 2d | (x4, y4, z4) |
| 2e | (x5, y5, z5) |
| 2f | (x6, y6, z6) |
| 2g | (x7, y7, z7) |
| 2h | (x8, y8, z8) |
| 2i | (x9, y9, z9) |
| 2j | (x10, y10, z10) |
| 2k | (x11, y11, z11) |
| 2l | (x12, y12, z12) |
| 2m | (x13, y13, z13) |
| 2n | (x14, y14, z14) |
| 2o | (x15, y15, z15) |
| 2p | (x16, y16, z16) |
| 2q | (x17, y17, z17) |
| 2r | (x18, y18, z18) |
| 2s | (x19, y19, z19) |
| 2t | (x20, y20, z20) |

FIG.6

| SUBJECT'S NAME | NAME NUMBER | DATE OF REHABILITATION | SENSOR | MOTION INFORMATION | | | |
|---|---|---|---|---|---|---|---|
| | | | | COLOR IMAGE INFORMATION | DISTANCE IMAGE INFORMATION | SOUND RECOGNITION RESULT | SKELETON INFORMATION |
| A | 1 | 20120801_1 | 10a | COLOR IMAGE INFORMATION | DISTANCE IMAGE INFORMATION | SOUND RECOGNITION RESULT | SKELETON INFORMATION |
| | | | 10b | COLOR IMAGE INFORMATION | DISTANCE IMAGE INFORMATION | SOUND RECOGNITION RESULT | SKELETON INFORMATION |
| | | 20120801_2 | 10a | COLOR IMAGE INFORMATION | DISTANCE IMAGE INFORMATION | SOUND RECOGNITION RESULT | SKELETON INFORMATION |
| | | | 10b | COLOR IMAGE INFORMATION | DISTANCE IMAGE INFORMATION | SOUND RECOGNITION RESULT | SKELETON INFORMATION |
| | | 20120802_1 | 10a | COLOR IMAGE INFORMATION | DISTANCE IMAGE INFORMATION | SOUND RECOGNITION RESULT | SKELETON INFORMATION |
| | | | 10b | COLOR IMAGE INFORMATION | DISTANCE IMAGE INFORMATION | SOUND RECOGNITION RESULT | SKELETON INFORMATION |
| | | ⋅ | ⋅ | ⋅ | ⋅ | ⋅ | ⋅ |
| | | ⋅ | ⋅ | ⋅ | ⋅ | ⋅ | ⋅ |
| ⋅ | ⋅ | ⋅ | ⋅ | ⋅ | ⋅ | ⋅ | ⋅ |

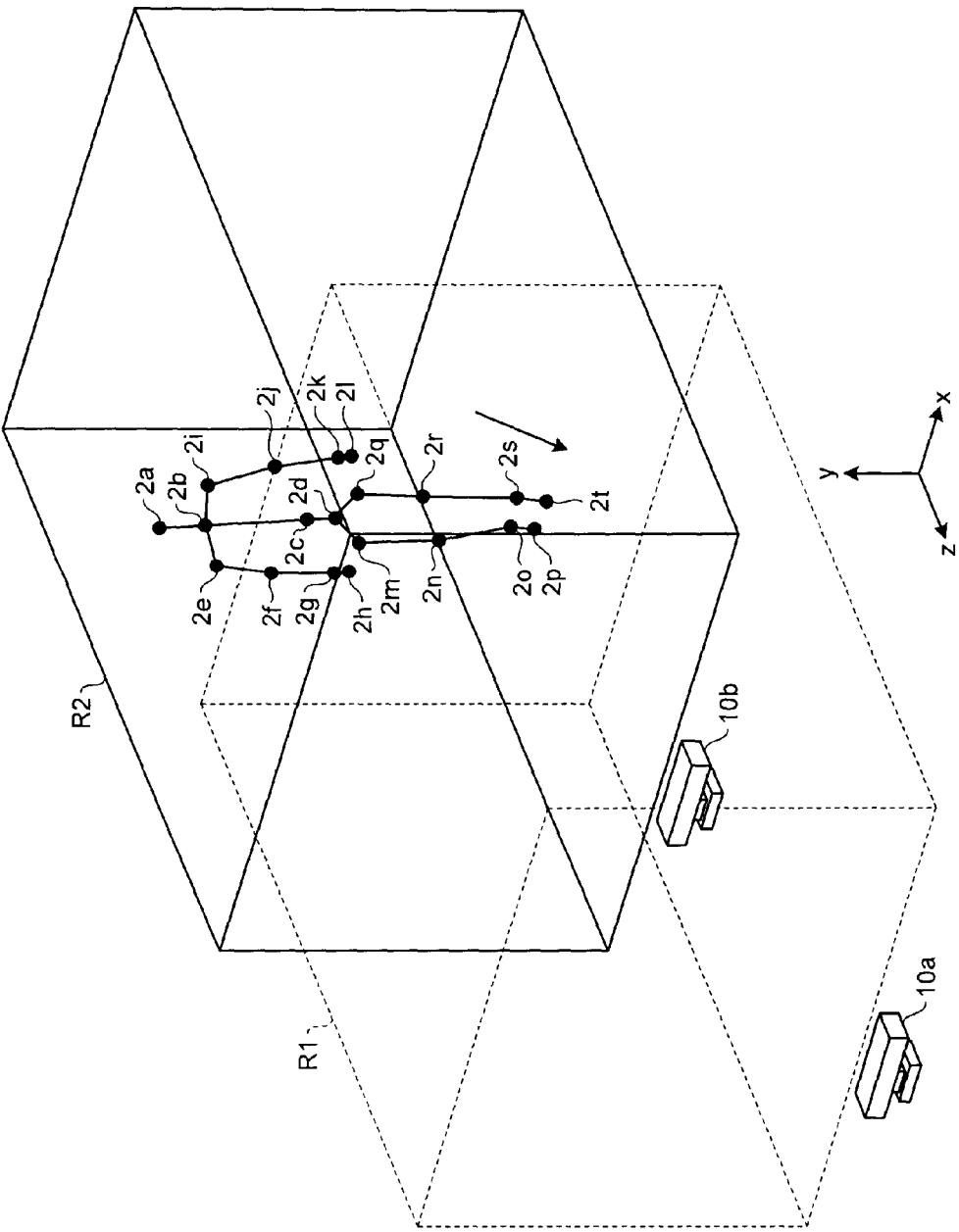

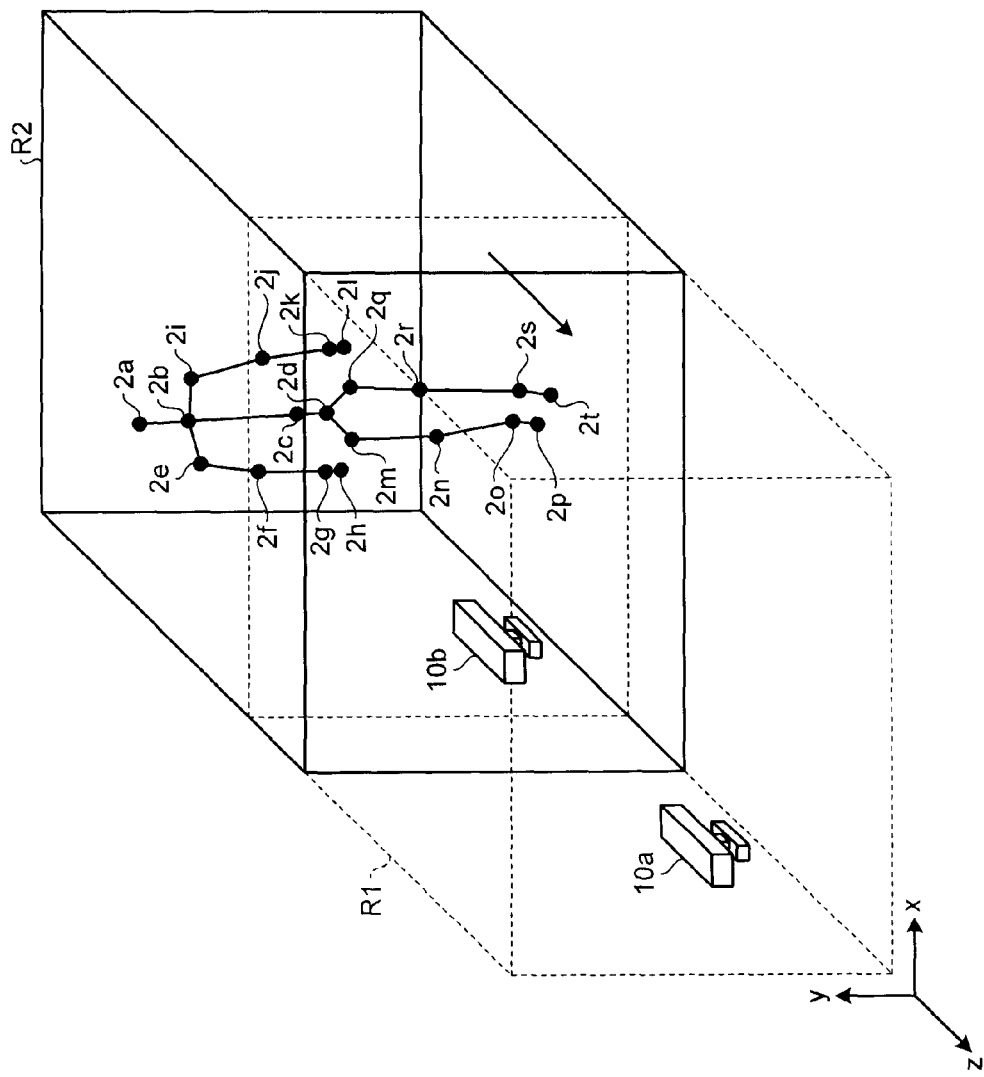

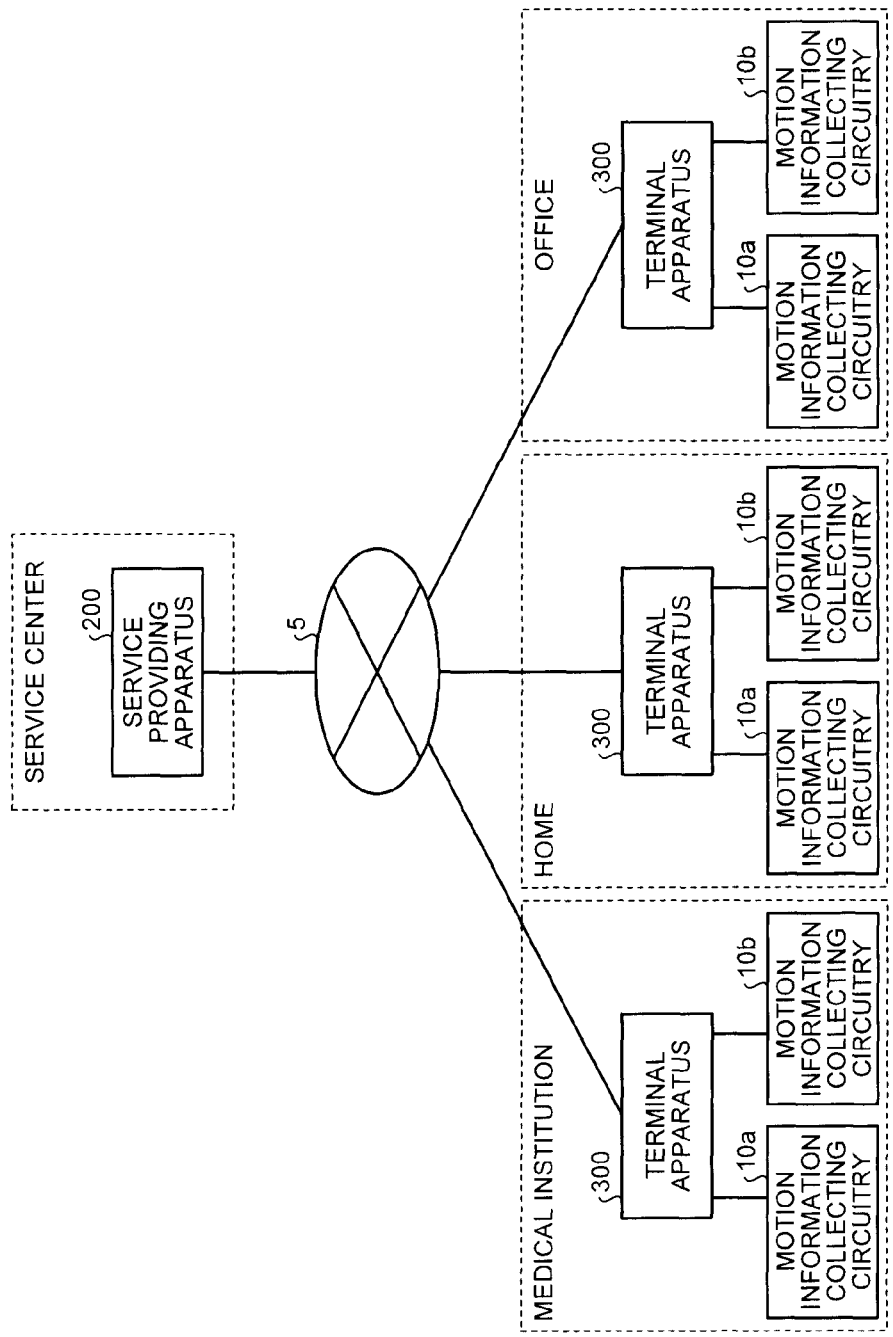

FIG.23

| SUBJECT'S NAME | NAME NUMBER | DATE OF REHABILITATION | MOTION INFORMATION | | | | |
|---|---|---|---|---|---|---|---|
| | | | COLOR IMAGE INFORMATION | DISTANCE IMAGE INFORMATION | SOUND RECOGNITION RESULT | SKELETON INFORMATION | · |
| A | 1 | 20120801_1 | COLOR IMAGE INFORMATION | DISTANCE IMAGE INFORMATION | SOUND RECOGNITION RESULT | SKELETON INFORMATION | · |
| | | 20120801_2 | COLOR IMAGE INFORMATION | DISTANCE IMAGE INFORMATION | SOUND RECOGNITION RESULT | SKELETON INFORMATION | · |
| | | 20120802_1 | COLOR IMAGE INFORMATION | DISTANCE IMAGE INFORMATION | SOUND RECOGNITION RESULT | SKELETON INFORMATION | · |
| | | · | · | · | · | · | · |
| B | 2 | 20120803_1 | COLOR IMAGE INFORMATION | DISTANCE IMAGE INFORMATION | SOUND RECOGNITION RESULT | SKELETON INFORMATION | · |
| | | 20120804_1 | COLOR IMAGE INFORMATION | DISTANCE IMAGE INFORMATION | SOUND RECOGNITION RESULT | SKELETON INFORMATION | · |
| | | 20120805_1 | COLOR IMAGE INFORMATION | DISTANCE IMAGE INFORMATION | SOUND RECOGNITION RESULT | SKELETON INFORMATION | · |
| | | · | · | · | · | · | · |
| · | · | · | · | · | · | · | · |

FIG.24

| SUBJECT'S NAME | NAME NUMBER | DATE OF REHABILITATION | SENSOR | SUBJECT INFORMATION | | | | | | | | | | | | | |
|---|---|---|---|---|---|---|---|---|---|---|---|---|---|---|---|---|---|
| A | 1 | 20120801_1 | PRESSURE SENSOR | PRESSURE INFORMATION | · | · | · | · | · | · | · | · | · | · | · | · | · |
| | | | HIGH-RESOLUTION GESTURE SENSOR | MOTION INFORMATION | · | · | · | · | · | · | · | · | · | · | · | · | · |
| | | 20120801_2 | SPHYGMOMANO- METER | BLOOD PRESSURE | · | · | · | · | · | · | · | · | · | · | · | · | · |
| | | | HEART RATE METER | HEART RATE | · | · | · | · | · | · | · | · | · | · | · | · | · |
| | | 20120802_1 | · | · | · | · | · | · | · | · | · | · | · | · | · | · | · |
| | | · | · | · | · | · | · | · | · | · | · | · | · | · | · | · | · |
| | | · | · | · | · | · | · | · | · | · | · | · | · | · | · | · | · |
| · | · | · | · | · | · | · | · | · | · | · | · | · | · | · | · | · | · |

OBTAIN MOVING DISTANCE "A" OF FLOOR ON BASIS OF ROTATION SPEED OF ROLLER OR THE LIKE

MOTION INFORMATION PROCESSING APPARATUS

CROSS-REFERENCE TO RELATED APPLICATIONS

This application is a continuation of PCT international application Ser. No. PCT/JP2014/051405 filed on Jan. 23, 2014 which designates the United States, incorporated herein by reference, and which claims the benefit of priority from Japanese Patent Application No. 2013-010524, filed on Jan. 23, 2013, Japanese Patent Application No. 2013-010547, filed on Jan. 23, 2013, and Japanese Patent Application No. 2013-223470, filed on Oct. 28, 2013, the entire contents of which are incorporated herein by reference.

FIELD

Embodiments described herein relate generally to a motion information processing apparatus.

BACKGROUND

Conventionally, a large number of experts have been providing collaborative aids for rehabilitation, for the purpose of offering a better life to people with physical or mental disabilities induced by various causes such as diseases, injuries, and aging, and to people with congenital disabilities. For example, rehabilitation is collaboratively aided by a large number of experts including rehabilitation medical specialists, rehabilitation nurses, physiotherapists, occupational therapists, speech pathologists, clinical psychologists, prosthetists, and social workers.

In addition, in recent years, motion capture technology for digitally recording movements of a person or an object has been developed. Examples of known methods that can be used in the motion capture technology include optical, mechanical, magnetic, and camera methods. As an example, a camera method is known by which a person wears a marker, so that a tracker device such as a camera detects the marker, and movements of the person are digitally recorded by processing the detected marker. Further, as for a method that does not use the marker and the tracker device, a method is known by which the distance between a sensor and a person is measured by using an infrared ray sensor, so that movements of the person are digitally recorded by detecting the size of the person and various movements of the skeleton. As an example of a sensor that uses this method, Kinect (registered trademark) is known.

BRIEF DESCRIPTION OF THE DRAWINGS

FIG. 4 is a table of an example of skeleton information generated by the motion information generating circuitry according to the first embodiment;

FIG. 6 is a table of an example of motion information stored in a motion information storage circuitry according to the first embodiment;

FIG. 7C is a schematic drawing for explaining yet another example of the motion information obtained by the obtaining circuitry according to the first embodiment;

FIG. 7D is a schematic drawing for explaining yet another example of the motion information obtained by the obtaining circuitry according to the first embodiment;

FIG. 19 is a diagram for explaining an example in which an aspect of the present disclosure is applied to a service providing apparatus according to the fourth embodiment;

FIG. 23 is a table of an example of motion information stored in a motion information storage circuitry according to the fifth embodiment;

FIG. 24 is a table of an example of subject information stored in a subject information storage circuitry according to the fifth embodiment;

DETAILED DESCRIPTION

According to embodiments, a motion information processing apparatus includes processing circuitry. The processing circuitry configured to obtain pieces of motion information of a subject acquired from a plurality of mutually-different positions with respect to the subject performing a predetermined motion. The processing circuitry configured to calculate association information used for bringing the pieces of motion information obtained into association with one another. The processing circuitry configured to exercise control so as to cause an output circuitry to output such output information in which the pieces of motion information are kept in association with one another on a basis of the association information calculated.

Exemplary embodiments of a motion information processing apparatus will be explained below, with reference to the accompanying drawings. The motion information processing apparatus described below may be used as a stand-alone motion information processing apparatus or may be used as being incorporated in a system such as a medical record system or a rehabilitation department system, for example. In this situation, the motion information processing apparatus according to an aspect of the present disclosure is configured to provide a subject undergoing rehabilitation with an effective aid, by obtaining detailed information about motions of the subject undergoing rehabilitation, by obtaining precise information of the subject undergoing rehabilitation, or by providing the subject performing a spatial move motion with a stable aid. In the following sections, the first to the fourth embodiments will refer to a motion information processing apparatus configured to obtain detailed information about motions of the subject undergoing rehabilitation; the fifth to the seventh embodiments will refer to a motion information processing apparatus configured to obtain precise information of the subject undergoing rehabilitation; and the eighth to the tenth embodiments will refer to a motion information processing apparatus configured to provide the subject performing the spatial move motion with a stable aid.

First Embodiment

Figure 1:
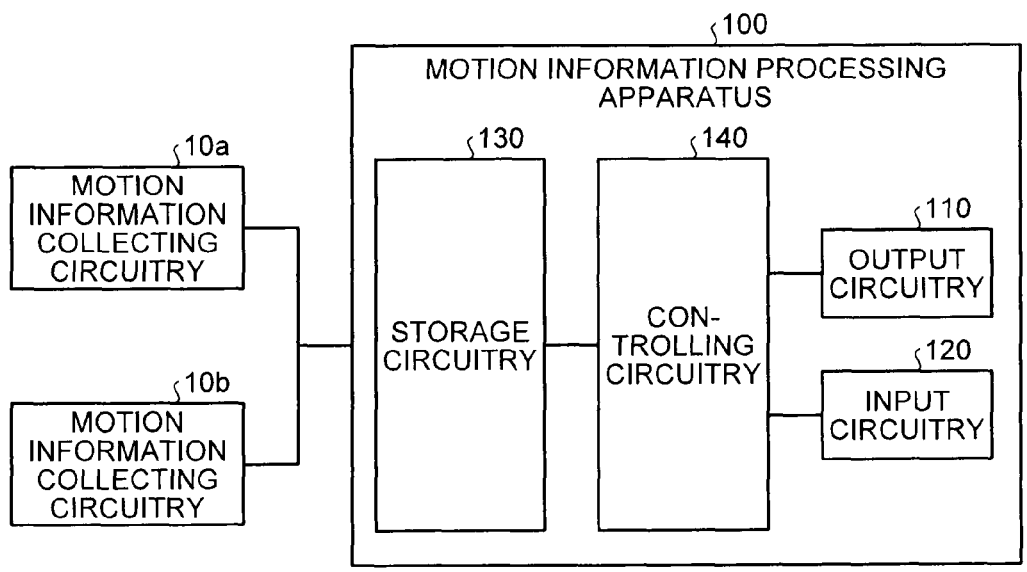
FIG. 1 is a diagram of an exemplary configuration of a motion information processing apparatus according to a first embodiment.

FIG. 1 is a diagram of an exemplary configuration of a motion information processing apparatus 100 according to a first embodiment. The motion information processing apparatus 100 according to the first embodiment is, for example, an apparatus configured to aid rehabilitation performed in a medical institution, a home, an office, or the like. In this situation, "rehabilitation" refers to techniques and methods for recovering or promoting vital functions as well as social functions, by enhancing potential capabilities of patients who have been treated for a long period of time due to disabilities, chronic diseases, geriatric diseases, and the like. Examples of the techniques and methods include functional training performed for recovering or promoting vital functions and social functions. In this situation, the functional training may be, for example, walking training or joint range-of-motion training. Further, a person who undergoes rehabilitation will be referred to as a "subject". The subject may be, for example, a person with a disease, a person with an injury, an elderly person, a person with disability, or the like. A person who assists a subject during rehabilitation will be referred to as a "caregiver". The caregiver may be, for example, a health care provider such as a medical doctor, a physiotherapist, a nurse, or the like who works at a medical institution, or may be a care worker, a family member, a friend, or the like who assists the subject at his/her home. Further, rehabilitation may simply be referred to as "rehab".

As illustrated in FIG. 1, in the first embodiment, the motion information processing apparatus 100 is connected to a motion information collecting circuitry 10a and a motion information collecting circuitry 10b. Although FIG. 1 illustrates the two motion information collecting circuitry, possible embodiments are not limited to this example. For instance, three or more motion information collecting circuitry may be connected to the motion information processing apparatus 100. Further, in the following sections, when having no need to be distinguished from each other, the motion information collecting circuitry 10a and the motion information collecting circuitry 10b may collectively be referred to as "motion information collecting circuitry 10".

Figure 2:
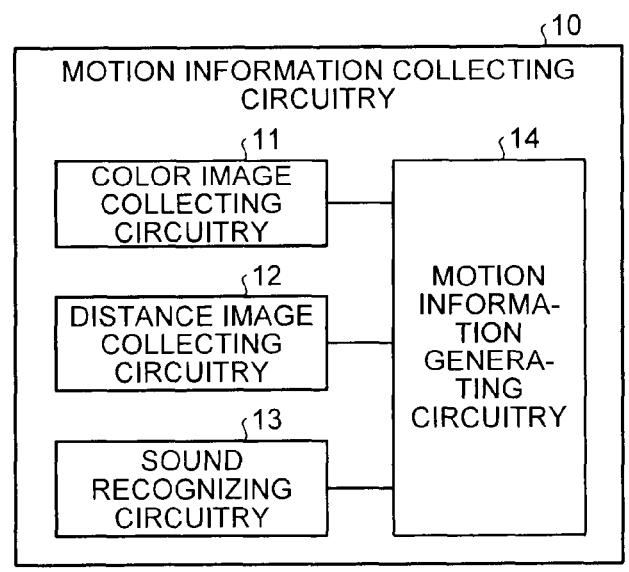
FIG. 2 is a diagram of an exemplary configuration of a motion information collecting circuitry according to the first embodiment.

Next, the motion information collecting circuitry 10a and the motion information collecting circuitry 10b will be explained. Because the motion information collecting circuitry 10a and the motion information collecting circuitry 10b perform the same processes as each other, the following explanation simply refers to either of these circuitry as "motion information collecting circuitry 10". FIG. 2 is a diagram of an exemplary configuration of the motion information collecting circuitry 10 according to the first embodiment. The motion information collecting circuitry 10 is configured to detect a motion of a person, an object, or the like in a space where rehabilitation is performed and to acquire motion information indicating the motion of the person, the object, or the like. The motion information will be explained in detail when processes performed by a motion information generating circuitry 14 are explained below. Further, the motion information collecting circuitry 10 may be configured by using, for example, Kinect (registered trademark).

As illustrated in FIG. 2, the motion information collecting circuitry 10 includes a color image collecting circuitry 11, a distance image collecting circuitry 12, a sound recognizing circuitry 13, and the motion information generating circuitry 14. The configuration of the motion information collecting circuitry 10 illustrated in FIG. 2 is merely an example, and possible embodiments are not limited to this example.

The color image collecting circuitry 11 is configured to acquire color image information by taking images of an imaged target such as the person, the object, or the like in the space where the rehabilitation is performed. For example, the color image collecting circuitry 11 detects light reflected on the surface of the imaged target by using a light receiving element and converts visible light into an electrical signal. After that, by converting the electrical signal into digital data, the color image collecting circuitry 11 generates color image information of one frame corresponding to an image taking region. The color image information corresponding to the one frame includes, for example, image-taking time information and information in which the pixels contained in the one frame are kept in correspondence with Red/Green/Blue (RGB) values. By generating color image information of a plurality of successive frames from a series of visible light that are sequentially detected, the color image collecting circuitry 11 takes a moving picture of the image taking region. The color image information generated by the color image collecting circuitry 11 may be output as color images in which the RGB values of the pixels are arranged in a bitmap. Further, the color image collecting circuitry 11 includes, for example, a Complementary Metal Oxide Semiconductor (CMOS) or a Charge Coupled Device (CCD), as the light receiving element.

The distance image collecting circuitry 12 is configured to acquire distance image information by taking images of the imaged target such as the person, the object, or the like in the space where the rehabilitation is performed. For example, the distance image collecting circuitry 12 radiates infrared rays into the surroundings thereof and detects reflected waves obtained as a result of the radiated waves being reflected on the surface of the imaged target, by using a light receiving element. After that, the distance image collecting circuitry 12 calculates the distance between the imaged target and the distance image collecting circuitry 12, on the basis of a phase difference between the radiated waves and the reflected waves or a time period between the radiation and the detection, and further generates the distance image information of one frame corresponding to the image taking region. The distance image information corresponding to the one frame includes, for example, image-taking time information and information in which each of the pixels included in the image taking region is kept in correspondence with the distance between the imaged target and the distance image collecting circuitry 12 that corresponds to the pixel. By generating distance image information of a plurality of successive frames from a series of reflected waves that are sequentially detected, the distance image collecting circuitry 12 takes a moving picture of the image taking region. The distance image information generated by the distance image collecting circuitry 12 may be output as distance images in which color gradation levels corresponding to the distances of the pixels are arranged in a bitmap. Further, the distance image collecting circuitry 12 includes, for example, a CMOS or a CCD as the light receiving element. The light receiving element may be used in common with the light receiving element used by the color image collecting circuitry 11. Further, for example, the distances calculated by the distance image collecting circuitry 12 may be expressed in the circuitry of meters [m].

The sound recognizing circuitry 13 is configured to collect sound in the surroundings thereof, to identify a direction of the source of the sound, and to perform a sound recognition process. The sound recognizing circuitry 13 has a microphone array including a plurality of microphones and performs a beam forming process. The beam forming process is realized with a technique of selectively collecting sound from a specific direction. For example, by performing the beam forming process that employs the microphone array, the sound recognizing circuitry 13 identifies the direction of the source of the sound. Further, by using a conventionally-known sound recognition technique, the sound recognizing circuitry 13 recognizes one or more words from the collected sound. In other words, for example, the sound recognizing circuitry 13 generates information in which the words recognized by using the sound recognition technique, the direction from which the words were uttered, and the time at which the words were recognized are kept in correspondence with one another, as an sound recognition result.

The motion information generating circuitry 14 is configured to generate the motion information indicating the motion of the person, the object, or the like. The motion information is generated by, for example, capturing the motion (a gesture) of the person, as a series of a plurality of postures (poses). An outline can be explained as follows: First, the motion information generating circuitry 14 obtains the coordinates of each of the joints forming the skeleton of the human body, from the distance image information generated by the distance image collecting circuitry 12, by performing a pattern matching process that uses a human body pattern. The coordinates of each of the joints obtained from the distance image information are values expressed in a coordinate system of the distance images (hereinafter, a "distance image coordinate system"). For this reason, the motion information generating circuitry 14 subsequently converts the coordinates of each of the joints in the distance image coordinate system into values expressed in a coordinate system of a three-dimensional space where the rehabilitation is performed (hereinafter, a "global coordinate system"). The coordinates of the joints expressed in the global coordinate system structure skeleton information corresponding to one frame. Further, pieces of skeleton information corresponding to a plurality of frames structure the motion information. In the following sections, processes performed by the motion information generating circuitry 14 according to the first embodiment will be explained more specifically.

Figure 3A:
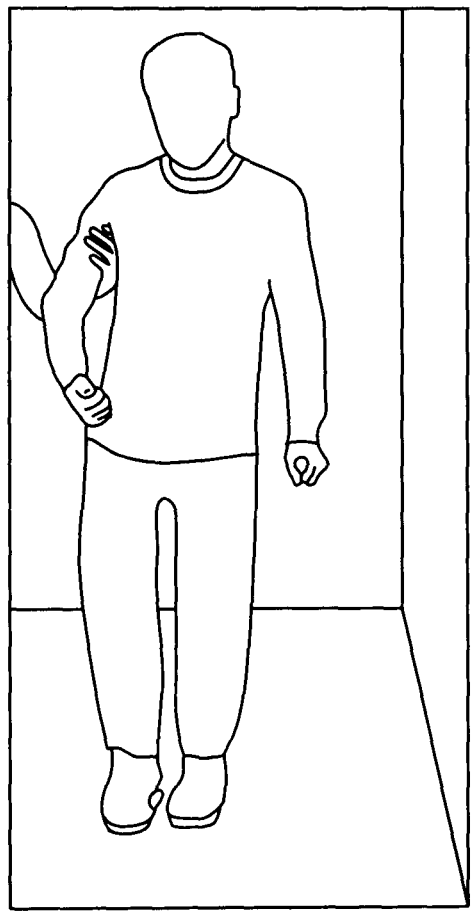
FIG. 3A is a drawing for explaining processes performed by a motion information generating circuitry according to the first embodiment.
Figure 3B:
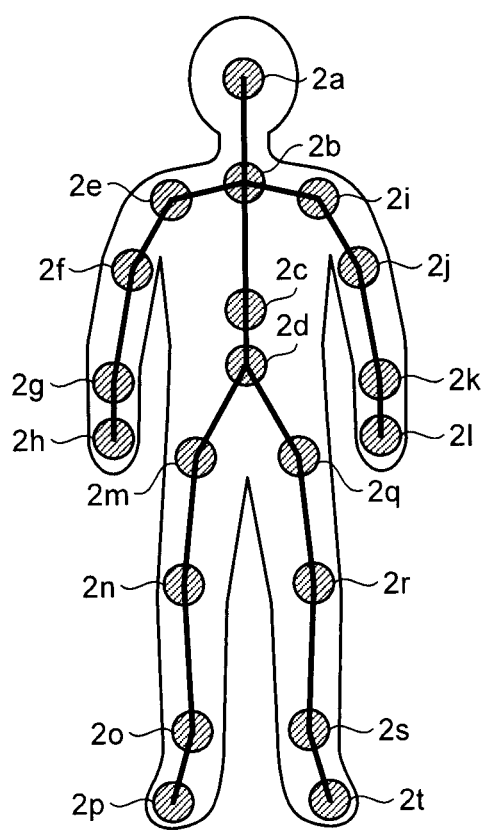
FIG. 3B is another drawing for explaining the processes performed by the motion information generating circuitry according to the first embodiment.
Figure 3C:
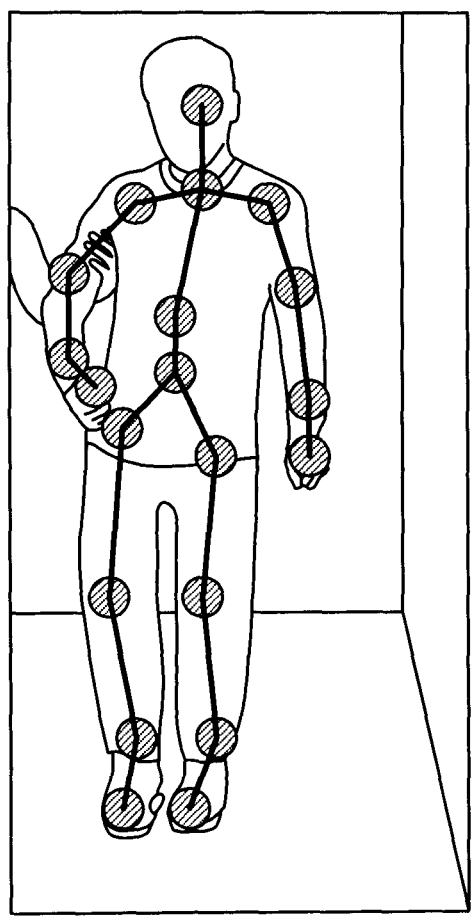
FIG. 3C is yet another drawing for explaining the processes performed by the motion information generating circuitry according to the first embodiment.

FIGS. 3A to 3C are drawings for explaining the processes performed by the motion information generating circuitry 14 according to the first embodiment. FIG. 3A illustrates an example of the distance image generated by the distance image collecting circuitry 12. Although FIG. 3A illustrates the image expressed with a line drawing for the sake of convenience in the explanation, the actual distance image may be an image expressed with a color gradation corresponding to the distances. In the distance image, each of the pixel has three-dimensional values in which a "pixel position X" in the left-and-right direction of the distance image, a "pixel position Y" in the up-and-down direction of the distance image, and a "distance Z" between the imaged target and the distance image collecting circuitry 12 corresponding to the pixel are kept in correspondence with one another. In the following sections, coordinate values in the distance image coordinate system will be expressed by using the three-dimensional values (X, Y, Z).

In the first embodiment, for example, the motion information generating circuitry 14 stores therein, through a learning process in advance, human body patterns corresponding to various postures. Every time a piece of distance image information is generated by the distance image collecting circuitry 12, the motion information generating circuitry 14 obtains the generated piece of distance image information corresponding to a frame. After that, the motion information generating circuitry 14 performs the pattern matching process on the obtained piece of distance image information corresponding to a frame, by using the human body patterns.

Next, the human body patterns will be explained. FIG. 3B illustrates an example of a human body pattern. In the first embodiment, the human body pattern is the pattern used in the pattern matching process with the distance image information. Thus, the human body pattern is expressed in the distance image coordinate system and has information about the surface of a human body (hereinafter, "human body surface"), similarly to the person rendered in the distance image. For example, the human body surface corresponds to the person's skin or the surface of the clothes. Further, as illustrated in FIG. 3B, the human body pattern has information about joints forming the skeleton of the human body. In other words, in the human body pattern, a relative positional relationship between the human body surface and each of the joints is known.

In the example illustrated in FIG. 3B, the human body pattern has information about the joints at twenty points such as joints $2a$ to $2t$. Among these joints, the joint $2a$ corresponds to the head, the joint $2b$ corresponds to a center part between the left and the right shoulders, the joint $2c$ corresponds to the lumbar, and the joint $2d$ corresponds to a center part of the buttocks. The joint $2e$ corresponds to the right shoulder, the joint $2f$ corresponds to the right elbow, the joint $2g$ corresponds to the right wrist, and the joint $2h$ corresponds to the right hand. Further, the joint $2i$ corresponds to the left shoulder, the joint $2j$ corresponds to the left elbow, the joint $2k$ corresponds to the left wrist, and the joint $2l$ corresponds to the left hand. The joint $2m$ corresponds to the right buttock, the joint $2n$ corresponds to the right knee, the joint $2o$ corresponds to the right ankle, and the joint $2p$ corresponds to the right tarsus. The joint $2q$ corresponds to the left buttock, the joint $2r$ corresponds to the left knee, the joint $2s$ corresponds to the left ankle, and the joint $2t$ corresponds to the left tarsus.

Although FIG. 3B illustrates an example in which the human body pattern has the information about the joints at the twenty points, possible embodiments are not limited to this example. The positions and the number of joints may arbitrarily be set by an operator. For example, to capture only changes in movements of the four limbs, it is not necessary to obtain the information about the joints $2b$ and $2c$, among the joints $2a$ to $2d$. In another example, to capture changes in movements of the right hand in detail, it is acceptable to additionally set the joints of the fingers of the right hand, in addition to the joint $2h$. It should be noted that the joints $2a$, $2h$, $2l$, $2p$, and $2t$ illustrated in FIG. 3B represent distal parts of the bones and are actually different from what is generally called "joints". However, because these points serve as important points indicating the positions and the orientations of the bones, these points will be referred to as joints for the sake of convenience in the explanation.

The motion information generating circuitry 14 performs the pattern matching process with the distance image information of each of the frames, by using the human body pattern described above. For example, the motion information generating circuitry 14 extracts the person in a certain posture from the distance image information by performing a pattern matching process between the human body surface of the human body pattern illustrated in FIG. 3B and the distance image illustrated in FIG. 3A. As a result, the motion information generating circuitry 14 obtains the coordinates of the human body surface of the person rendered in the distance image. Further, as noted above, in the human body pattern, the relative positional relationship between the human body surface and each of the joints is known. Accordingly, the motion information generating circuitry 14 calculates the coordinates of each of the joints in the person, on the basis of the coordinates of the human body surface of the person rendered in the distance image. As a result, the motion information generating circuitry 14 obtains, as illustrated in FIG. 3C, the coordinates of each of the joints structuring the skeleton of the human body, from the distance image information. The coordinates of each of the joints obtained in this situation are coordinates expressed in the distance image coordinate system.

When performing the pattern matching process, the motion information generating circuitry 14 may auxiliarily use information indicating positional relationships among the joints. The information indicating the positional relationships among the joints include, for example, information about connection relationships among joints (e.g., "the joint $2a$ is connected to the joint $2b$") and information about a range of motion of each of the joints. Joints are sites at which two or more bones are connected together. The angle formed by bones varies according to changes in the posture. Also, the ranges of motion are different for different joints. For example, the range of motion of a joint may be expressed with the largest and the smallest values of the angle formed by the bones connected together by the joint. For example, when learning a human body pattern, the motion information generating circuitry 14 also learns the range of motion of each of the joints and further stores the learned ranges of motion therein in correspondence with the joints.

Subsequently, the motion information generating circuitry 14 converts the coordinates of each of the joints expressed in the distance image coordinate system into values expressed in the global coordinate system. The global coordinate system is a coordinate system of the three-dimensional space where the rehabilitation is performed. The global coordinate system is expressed while using, for example, the position of the motion information collecting circuitry 10 as the origin, the horizontal direction as the x-axis, the vertical direction as the y-axis, and the direction orthogonal to the x-y plane as the z-axis. In any set of coordinates, the coordinate value in the z-axis direction may be referred to as a "depth".

Next, the conversion process from the distance image coordinate system to the global coordinate system will be explained. In the first embodiment, it is assumed that the motion information generating circuitry 14 has stored therein, in advance, a conversion formula used for the conversion from the distance image coordinate system to the global coordinate system. For example, the conversion formula takes coordinates in the distance image coordinate system and an incident angle of the reflected light corresponding to the coordinates as inputs, and outputs coordinates in the global coordinate system. For example, the motion information generating circuitry 14 inputs coordinates (X1, Y1, Z1) of a certain joint and the incident angle of the reflected light corresponding to the coordinates to the conversion formula, so as to covert the coordinates (X1, Y1, Z1) of the joint into coordinates (x1, y1, z1) in the global coordinate system. Because the correspondence relationship between any set of coordinates in the distance image coordinate system and the incident angle of the reflected light is known, the motion information generating circuitry 14 is able to input the incident angle corresponding to the coordinates (X1, Y1, Z1) to the conversion formula. Further, although the example in which the motion information generating circuitry 14 converts the coordinates in the distance image coordinate system into the coordinates in the global coordinate system has been explained, it is also possible to convert coordinates in the global coordinate system into coordinates in the distance image coordinate system.

After that, the motion information generating circuitry 14 generates the skeleton information from the coordinates of each of the joints expressed in the global coordinate system. FIG. 4 is a table of an example of the skeleton information generated by the motion information generating circuitry 14. The skeleton information of each of the frames includes image-taking time information of the frame and the coordinates of each of the joints. For example, as illustrated in FIG. 4, the motion information generating circuitry 14 generates skeleton information in which joint identification information and coordinate information are kept in correspondence with each other. The image-taking time information is omitted from the table in FIG. 4. The joint identification information is identification information used for identifying each of the joints and is set in advance. For example, joint identification information "2a" corresponds to the head, whereas joint identification information "2b" corresponds to a center part between the left and the right shoulders. Each of the other pieces of joint identification information similarly identifies a corresponding one of the joints. The coordinate information indicates the coordinates of each of the joints in each of the frames, in the global coordinate system.

In the first row of the table in FIG. 4, the joint identification information "2a" is kept in correspondence with the coordinate information "(x1, y1, z1)". It means that, in the skeleton information illustrated in FIG. 4, the head is located in the position at the coordinates (x1, y1, z1) in a certain frame. As another example, in the second row of the table in FIG. 4, the joint identification information "2b" is kept in correspondence with the coordinate information "(x2, y2, z2)". It means that, in the skeleton information illustrated in FIG. 4, the center part between the left and the right shoulders is located in the position at the coordinates (x2, y2, z2) in the certain frame. Similarly, for each of the other joints also, it is indicated that the joint is located in the position expressed by the set of coordinates, in the certain frame.

As explained above, the motion information generating circuitry 14 generates the skeleton information for each of the frames, by performing the pattern matching process on the distance image information of each frame every time the distance image information of a frame is obtained from the distance image collecting circuitry 12 and converting the coordinates in the distance image coordinate system into those in the global coordinate system. After that, the motion information generating circuitry 14 outputs the generated skeleton information of each of the frames to the motion information processing apparatus 100, so as to store the skeleton information into a motion information storage circuitry 1301 (explained later).

The method used by the motion information generating circuitry 14 for performing the processes is not limited to the one described above. For example, in the description above, the method is explained by which the motion information generating circuitry 14 performs the pattern matching process by using the human body pattern; however, possible embodiments are not limited to this example. For instance, another method is acceptable by which instead of or together with the human body pattern, a pattern matching process is performed by using patterns corresponding to different sites of the body.

Further, for example, in the description above, the method is explained by which the motion information generating circuitry 14 obtains the coordinates of each of the joints from the distance image information; however, possible embodiments are not limited to this example. For instance, another method is acceptable by which the motion information generating circuitry 14 obtains the coordinates of each of the joints by using the color image information together with the distance image information. In that situation, for example, the motion information generating circuitry 14 performs a pattern matching process by using a human body pattern expressed by using a coordinate system of the color images and the color image information, so as to obtain the coordinates of the human body surface from the color image information. The coordinate system of the color images includes no information about the "distance Z" that is used in the distance image coordinate system. For this reason, the motion information generating circuitry 14 obtains the information about the "distance Z" from the distance image information, for example, and obtains the coordinates of each of the joints in the global coordinate system by performing a calculating process while using the two types of information.

Further, the motion information generating circuitry 14 outputs, as appropriate, the color image information generated by the color image collecting circuitry 11, the distance image information generated by the distance image collecting circuitry 12, and the sound recognition result output by the sound recognizing circuitry 13 to the motion information processing apparatus 100, if necessary, so as to store any of these pieces of information into the motion information storage circuitry 1301 (explained later). Incidentally, it is possible to bring the pixel positions of the color image information into correspondence with the pixel positions of the distance image information, in advance, in accordance with the positions and the image-taking directions of the color image collecting circuitry 11 and the distance image collecting circuitry 12. Accordingly, it is also possible to bring the pixel positions of the color image information and the pixel positions of the distance image information into correspondence with the global coordinate system calculated by the motion information generating circuitry 14. Similarly, it is also possible to bring the image-taking time information of the color image information into correspondence with the image-taking time information of the distance image information, in advance. Further, if the joint 2a is found to be positioned near a direction in which a word was uttered of which the sound was recognized at a certain time, with reference to the sound recognition result and the distance image information, the motion information generating circuitry 14 is able to output the word as a word uttered by the person who includes the joint 2a. Further, the motion information generating circuitry 14 also outputs, as appropriate, the information indicating the positional relationships among the joints to the motion information processing apparatus 100, if necessary, so as to store the information into the motion information storage circuitry 1301 (explained later).

In the description above, the example is explained in which the motion information collecting circuitry 10 detects the motion of the single subject; however, possible embodiments are not limited to this example. The motion information collecting circuitry 10 may detect motions of a plurality of subjects, as long as the motions of the subjects are included in the detection range of the motion information collecting circuitry 10.

Further, the configuration of the motion information collecting circuitry 10 is not limited to the one described above. For example, when the motion information is generated by detecting the motions of a person by using any other motion capture method such as an optical method, a mechanical method, a magnetic method, or the like, the motion information collecting circuitry 10 does not necessarily have to include the distance image collecting circuitry 12. In that situation, the motion information collecting circuitry 10 includes, as a motion sensor, a marker to be attached to the human body for the purpose of detecting the motions of the person and a sensor configured to detect the marker. Further, the motion information collecting circuitry 10 generates the motion information by detecting the motions of the person with the use of the motion sensor. Further, by using the position of the marker included in images taken by the color image collecting circuitry 11, the motion information collecting circuitry 10 brings the pixel positions of the color image information into correspondence with the coordinates in the motion information and subsequently outputs the information, as appropriate, to the motion information processing apparatus 100, if necessary. Further, for example, when the motion information collecting circuitry 10 does not output the sound recognition result to the motion information processing apparatus 100, the motion information collecting circuitry 10 does not necessarily have to include the sound recognizing circuitry 13.

Further, in the embodiment described above, the motion information collecting circuitry 10 outputs the coordinates in the global coordinate system as the skeleton information; however, possible embodiments are not limited to this example. For instance, the motion information collecting circuitry 10 may output the coordinates in the distance image coordinate system before the conversion, so that the conversion from the distance image coordinate system into the global coordinate system is performed on the motion information processing apparatus 100 side as necessary. The detailed example of the motion information collecting circuitry 10 has thus been explained. Each of the motion information collecting circuitry 10a and 10b connected to the motion information processing apparatus 100 is configured as described above, for example.

Returning to the description of FIG. 1, the motion information processing apparatus 100 is configured to perform processes to aid the rehabilitation, by using the motion information output from the motion information collecting circuitry 10. More specifically, the motion information processing apparatus 100 displays the pieces of motion information that are of the subject undergoing rehabilitation and are acquired by the motion information collecting circuitry 10a and the motion information collecting circuitry 10b, so as to be kept in synchronization with each other.

As noted above, as functional training for rehabilitation, various types of training such as walking training and joint range-of-motion training are conventionally performed. Among the various types of training, for example, some training may require that the subject is observed from multiple directions or that the training is performed for a predetermined distance. For example, during walking training, a subject may walk a distance of approximately 10 meters, or the walking may be observed from the front or a side. For this reason, the motion information processing apparatus 100 according to the first embodiment is configured to make it possible to obtain detailed information about motions of a subject undergoing rehabilitation.

For example, the motion information processing apparatus 100 is an information processing apparatus configured with a computer, a workstation, or the like and includes, as illustrated in FIG. 1, an output circuitry 110, an input circuitry 120, a storage circuitry 130, and a controlling circuitry 140.

The output circuitry 110 is configured to output various types of information and the like related to the motions of the subject undergoing the rehabilitation. For example, the output circuitry 110 displays a Graphical User Interface (GUI) used by an operator who operates the motion information processing apparatus 100 to input various types of requests through the input circuitry 120 and displays image information indicating a walking state of the subject on the motion information processing apparatus 100. For example, the output circuitry 110 is configured by using a monitor, a speaker, a headphone, a headphone portion of a headset, and/or the like. Further, the output circuitry 110 may be configured by using a display device of such a type that is attached to the body of the user, e.g., an eyeglass-type display device or a head-mount display device.

The input circuitry 120 is configured to receive an input of various types of information related to the motions of the subject undergoing the rehabilitation. For example, the input circuitry 120 receives an input of various types of requests (e.g., a selecting request to select an image to be displayed, and a measuring request to have a measuring process performed by using the GUI) from the operator of the motion information processing apparatus 100 and transfers the received various types of requests to the motion information processing apparatus 100. For example, the input circuitry 120 may be configured by using a mouse, a keyboard, a touch command screen, a trackball, a microphone, a microphone portion of a headset, and/or the like. Further, the input circuitry 120 may be a sensor configured to obtain biological information such as a sphygmomanometer, a heart rate meter, a clinical thermometer, and/or the like.

The storage circuitry 130 is a storage device configured by using, for example, a semiconductor memory device such as a Random Access Memory (RAM) or a flash memory, a hard disk device, or an optical disk device. Further, the controlling circuitry 140 may be configured by using an integrated circuit such as an Application Specific Integrated Circuit (ASIC) or a Field Programmable Gate Array (FPGA) or may be realized by a Central Processing Unit (CPU) executing a predetermined computer program.

Figure 5:
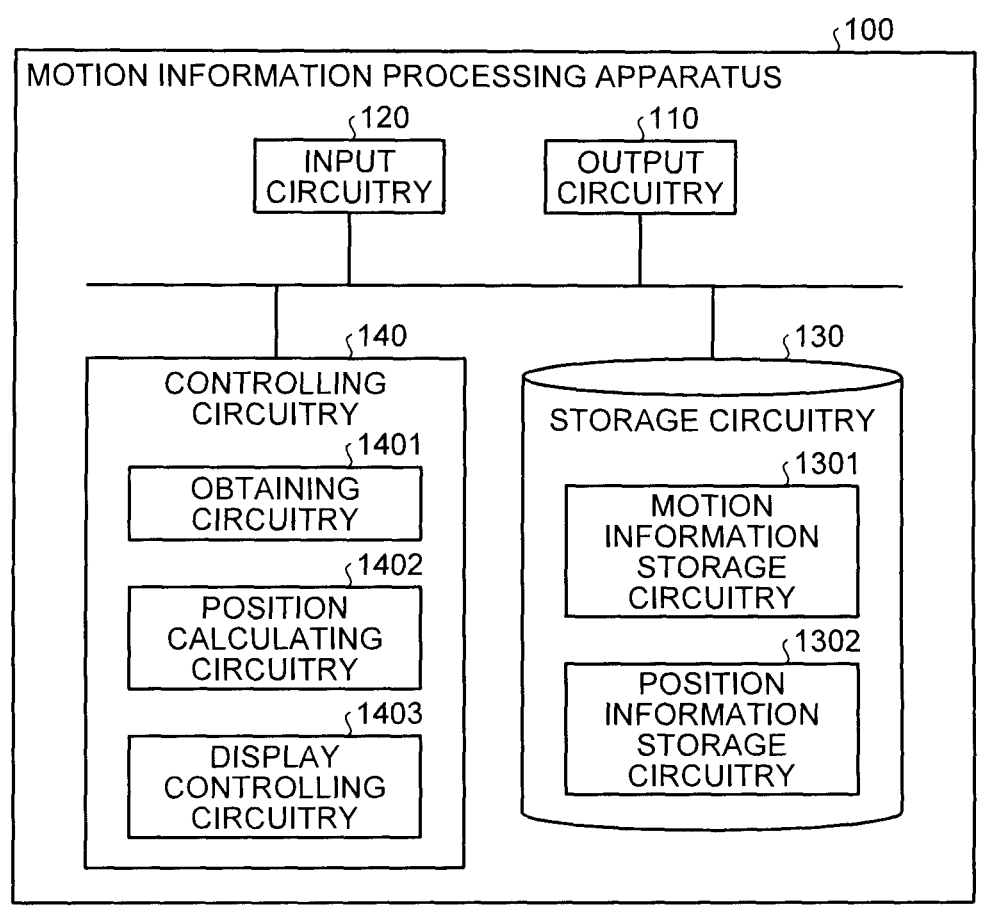
FIG. 5 is a diagram of an exemplary detailed configuration of the motion information processing apparatus according to the first embodiment.

A configuration of the motion information processing apparatus 100 according to the first embodiment has thus been explained. The motion information processing apparatus 100 according to the first embodiment configured as described above makes it possible to obtain the detailed information about the motions of the subject undergoing rehabilitation, by using the configuration explained below in detail. FIG. 5 is a diagram of an exemplary detailed configuration of the motion information processing apparatus 100 according to the first embodiment. First, details of the storage circuitry 130 included in the motion information processing apparatus 100 will be explained. As illustrated in FIG. 5, in the motion information processing apparatus 100, for example, the storage circuitry 130 includes the motion information storage circuitry 1301 and a position information storage circuitry 1302.

The motion information storage circuitry 1301 is configured to store therein various types of information acquired by the motion information collecting circuitry 10. More specifically, the motion information storage circuitry 1301 stores therein the pieces of motion information generated by the motion information generating circuitry 14 included in the motion information collecting circuitry 10a and 10b. Even more specifically, the motion information storage circuitry 1301 stores therein the skeleton information for each of the frames generated by the motion information generating circuitry 14 included in the motion information collecting circuitry 10. In this situation, the motion information storage circuitry 1301 is also able to store therein the color image information, the distance image information, and the sound recognition result output by the motion information generating circuitry 14 in such a manner that these pieces of information are further kept in correspondence with one another for each of the frames.

FIG. 6 is a table of an example of the motion information stored in the motion information storage circuitry 1301 according to the first embodiment. As illustrated in FIG. 6, the motion information storage circuitry 1301 stores therein motion information in which the name of each subject is kept in correspondence with a name number, dates of rehabilitation, sensors, and pieces of motion information. In this situation, the "name number" is an identifier used for uniquely identifying the subject and is assigned to each subject name. Each of the "dates of rehabilitation" denotes a date on which the subject underwent the rehabilitation training. The "sensors" denote the sensors that acquired the motion information of the subject undergoing the rehabilitation. Each of the pieces of "motion information" denotes the information acquired by the motion information collecting circuitry 10a or the motion information collecting circuitry 10b.

For example, as illustrated in FIG. 6, the motion information storage circuitry 1301 stores therein "Subject's Name: A; Name Number: 1; Date of Rehabilitation: 20120801_1; Sensor: 10a; Motion Information: Color image information, Distance image information, sound recognition result, Skeleton information, and . . . ". Further, for example, as illustrated in FIG. 6, the motion information storage circuitry 1301 stores therein "Subject's Name: A; Name Number: 1; Date of Rehabilitation: 20120801_1; Sensor: 10b; Motion Information: Color image information, Distance image information, sound recognition result, Skeleton information, and . . . ". These pieces of information indicate that, for the "first time" rehabilitation performed on "August 1st" in the "year 2012" by the person named "Subject's Name: A" of which the "Name Number" is "1", the motion information including the "color image information, distance image information, sound recognition result, skeleton information, and so on" acquired by the "sensor: 10a" and the motion information including the "color image information, distance image information, sound recognition result, skeleton information, and so on" acquired by the "sensor: 10b" are stored.

In this situation, in the motion information illustrated in FIG. 6, the "color image information", the "distance image information", the "sound recognition result", the "skeleton information", and so on for each of all the frames taken while the rehabilitation motions are being performed are stored for each of the sensors while being kept in correspondence with times in a time-series order. In other words, the motion information storage circuitry 1301 stores therein the "color image information", the "distance image information", the "sound recognition result", the "skeleton information", and so on that are acquired by each of the motion information collecting circuitry 10a and 10b during the rehabilitation motions of one time, while keeping these pieces of information in correspondence with the times at which these pieces of information are acquired. That is to say, the motion information storage circuitry 1301 stores therein the motion information acquired by each of the motion information collecting circuitry 10a and 10b, so as to be kept in correspondence with the times of the frames.

Further, as illustrated in FIG. 6, the motion information storage circuitry 1301 stores therein "Subject's Name: A; Name Number: 1; Date of Rehabilitation: 20120801_2; Sensor: 10a; Motion Information: Color image information, Distance image information, Sound recognition result, Skeleton information, and . . . " and "Subject's Name: A; Name Number: 1; Date of Rehabilitation: 20120801_2; Sensor: 10b; Motion Information: Color image information, Distance image information, Sound recognition result, Skeleton information, and . . . ". In other words, the motion information storage circuitry 1301 also similarly stores therein the motion information from the "second time" rehabilitation performed on "August 1st" in the "year 2012" by the person named "Subject's Name: A".

As illustrated in FIG. 6, also for other people, the motion information storage circuitry 1301 similarly stores therein motion information including "color image information", "distance image information", an "sound recognition result", "skeleton information", and so on. The motion information storage circuitry 1301 thus stores therein the motion information of the rehabilitation acquired for each of the subjects, so as to be kept in correspondence with the subject. The motion information illustrated in FIG. 6 is merely an example. In other words, the motion information storage circuitry 1301 is able to store therein any information other than the "color image information", "distance image information", "sound recognition result" and "skeleton information" illustrated in FIG. 6, so as to be further kept in correspondence therewith. Further, for example, if the motion information collecting circuitry 10 each do not include the sound recognizing circuitry 13, the motion information storage circuitry 1301 stores therein information that includes no sound recognition result.

The position information storage circuitry 1302 is configured to store therein an analysis result obtained by the controlling circuitry 140 (explained later). More specifically, the position information storage circuitry 1302 stores therein position information that is used for correcting positions among sensors and is calculated by the controlling circuitry 140 (explained later) while using the motion information stored in the motion information storage circuitry 1301. The position information will be explained later.

Next, details of the controlling circuitry 140 included in the motion information processing apparatus 100 will be explained. As illustrated in FIG. 5, in the motion information processing apparatus 100, for example, the controlling circuitry 140 includes an obtaining circuitry 1401, a position calculating circuitry 1402, and a display controlling circuitry 1403.

The obtaining circuitry 1401 is configured to obtain the pieces of motion information of a subject acquired from mutually-different positions with respect to the subject performing a predetermined motion (e.g., rehabilitation). More specifically, the obtaining circuitry 1401 obtains the motion information stored in the motion information storage circuitry 1301. For example, the obtaining circuitry 1401 obtains the pieces of motion information acquired by the motion information collecting circuitry 10a and the motion information collecting circuitry 10b. In one example, the obtaining circuitry 1401 obtains the pieces of color image information, the pieces of distance image information, the sound recognition results, and the pieces of skeleton information that are acquired by the motion information collecting circuitry 10a and the motion information collecting circuitry 10b and are stored in the motion information storage circuitry 1301 for each of the frames.

Figure 7A:
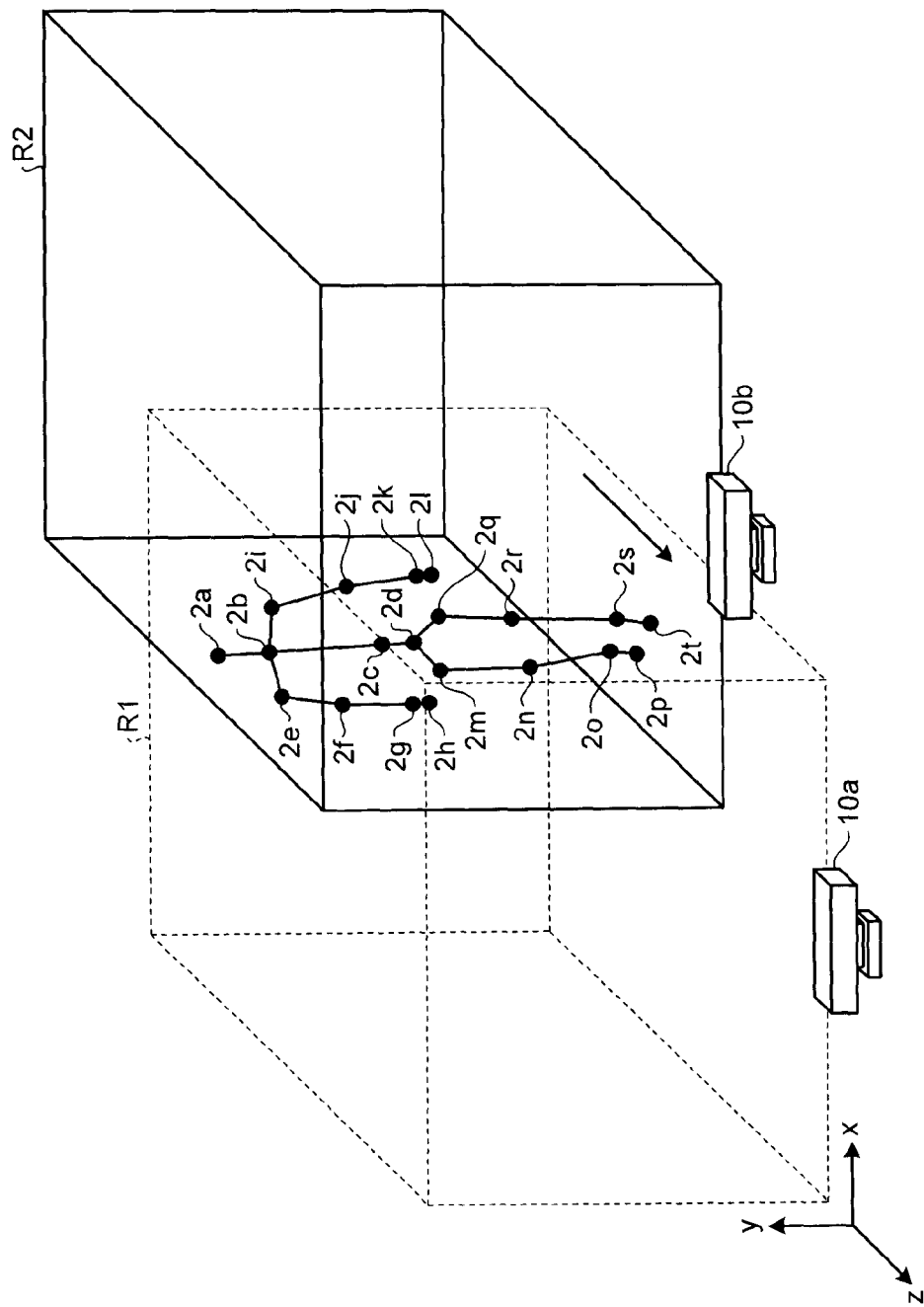
FIG. 7A is a schematic drawing for explaining an example of motion information obtained by an obtaining circuitry according to the first embodiment.

FIGS. 7A to 7D are schematic drawings for explaining examples of the motion information obtained by the obtaining circuitry 1401 according to the first embodiment. FIG. 7A illustrates an example in which the motion information collecting circuitry 10a and the motion information collecting circuitry 10b are positioned as shown in the drawing (the motion information collecting circuitry 10b is arranged in a position slid from the position of the motion information collecting circuitry 10a), so as to obtain the motion information of a situation where the subject is performing walking training along the z-axis direction. For example, as illustrated in FIG. 7A, the obtaining circuitry 1401 obtains, from the motion information storage circuitry 1301, the motion information acquired by the motion information collecting circuitry 10a and the motion information acquired by the motion information collecting circuitry 10b, while the subject is performing the walking training along the z-axis direction.

In other words, as illustrated in FIG. 7A, the obtaining circuitry 1401 obtains color image information, distance image information, skeleton information, and so on of the subject in a region R1 that is an image taking region of the motion information collecting circuitry 10a and also obtains color image information, distance image information, skeleton information, and so on of the subject in a region R2 that is an image taking region of the motion information collecting circuitry 10b. In this situation, for example, the obtaining circuitry 1401 obtains the pieces of motion information by using the subject's name, the name number, the date of rehabilitation, or the like as a key. In other words, the obtaining circuitry 1401 obtains pieces of color image information, pieces of distance image information, and pieces of skeleton information that correspond to all the frames related to a series of walking motions made during the walking training of the subject and are acquired by the motion information collecting circuitry 10. Alternatively, the obtaining circuitry 1401 may obtain, in a real-time manner, the pieces of motion information stored in the motion information storage circuitry 1301 in a real-time manner.

Figure 7B:
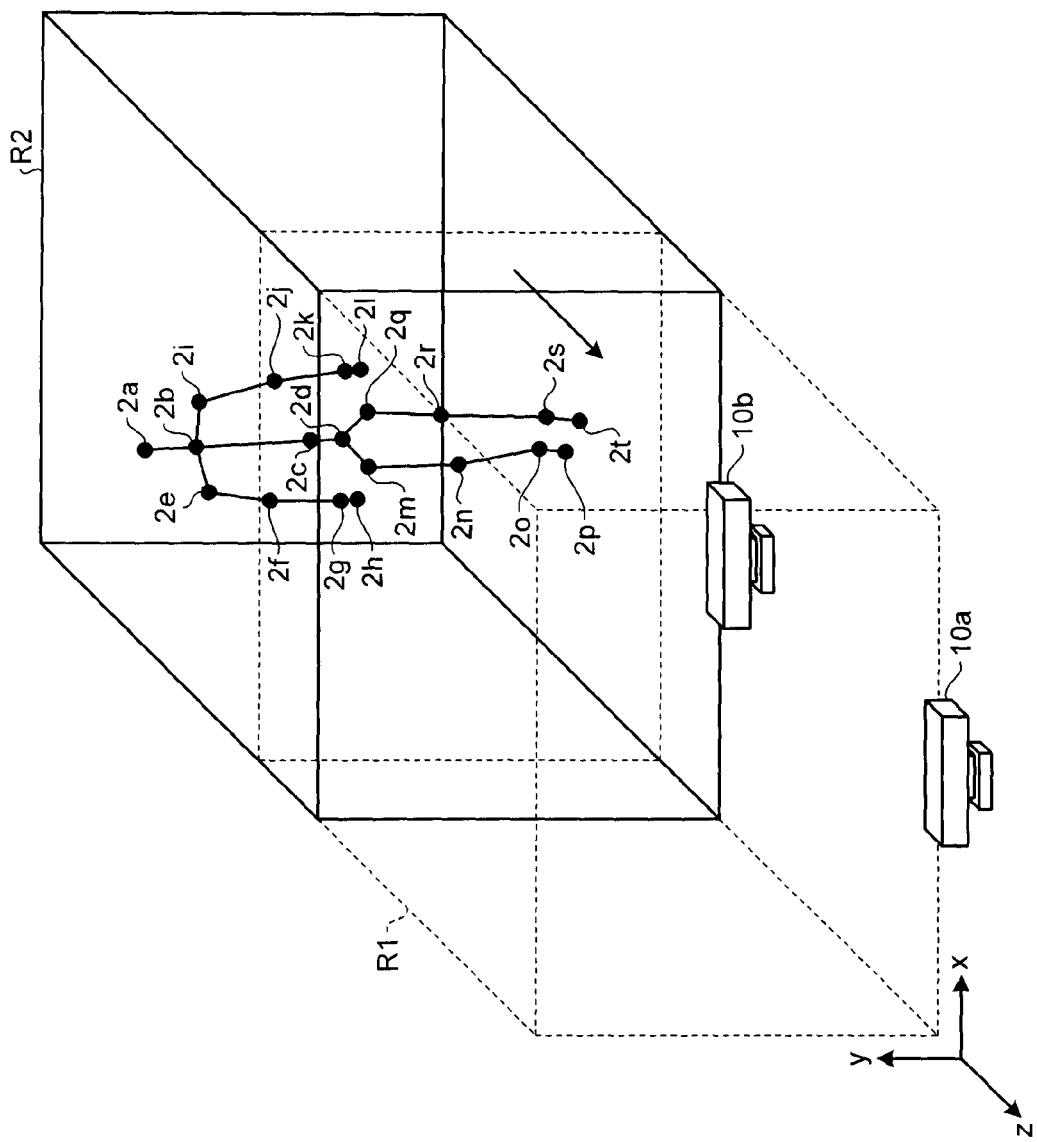
FIG. 7B is a schematic drawing for explaining another example of the motion information obtained by the obtaining circuitry according to the first embodiment.

The configuration described above is merely an example. The obtaining circuitry 1401 is able to obtain the pieces of motion information acquired by the motion information collecting circuitry 10a and the motion information collecting circuitry 10b that are disposed in other various positional arrangements. For example, while the motion information collecting circuitry 10a and the motion information collecting circuitry 10b are arranged along the z-axis direction as illustrated in FIG. 7B, the obtaining circuitry 1401 may obtain, from the motion information storage circuitry 1301, the motion information acquired by the motion information collecting circuitry 10a and the motion information acquired by the motion information collecting circuitry 10b, while the subject is performing the walking training along the z-axis direction.

Alternatively, for example, while the motion information collecting circuitry 10a and the motion information collecting circuitry 10b are arranged so as to be oriented diagonally along the z-axis direction as illustrated in FIG. 7C, the obtaining circuitry 1401 may obtain, from the motion information storage circuitry 1301, the motion information acquired by the motion information collecting circuitry 10a and the motion information acquired by the motion information collecting circuitry 10b, while the subject is performing the walking training at an angle relative to the z-axis direction. When the motion information collecting circuitry 10a and the motion information collecting circuitry 10b are arranged in this manner, it is possible to secure a walking route in such a manner that the walking of the subject is not hindered. Even in the situation where the motion information collecting circuitry 10a and the motion information collecting circuitry 10b are arranged as illustrated in FIG. 7C, it is possible to display images of the subject taken from the front, by applying a three-dimensional conversion to the data of the motion information. For example, the three-dimensional conversion is applied to the motion information by obtaining angle information of the orientations of the motion information collecting circuitry 10a and the motion information collecting circuitry 10b with respect to the advancing direction of the walk of the subject (the z-axis direction) and using the obtained angle information.

Alternatively, for example, while the motion information collecting circuitry 10a and the motion information collecting circuitry 10b are arranged so as to be oriented exactly sideways (in the z-axis direction) along the z-axis direction as illustrated in FIG. 7D, the obtaining circuitry 1401 may obtain, from the motion information storage circuitry 1301, the motion information acquired by the motion information collecting circuitry 10a and the motion information acquired by the motion information collecting circuitry 10b, while the subject is performing the walking training along the z-axis direction. With this arrangement, it is possible to keep obtaining the motion information related to the walking of the subject from the exactly sideway direction.

Returning to the description of FIG. 5, the position calculating circuitry 1402 is configured to calculate association information used for bringing the pieces of motion information obtained by the obtaining circuitry 1401 into association with one another. More specifically, the position calculating circuitry 1402 calculates synchronization information used for bringing the pieces of motion information obtained by the obtaining circuitry 1401 into synchronization with one another. Even more specifically, the position calculating circuitry 1402 calculates the synchronization information used for bringing the positions of the pieces of motion information acquired by the motion information collecting circuitry 10a and the motion information collecting circuitry 10b into synchronization (positional alignment) with each other. An example of the process performed by the position calculating circuitry 1402 will be explained below.

Figure 8A:
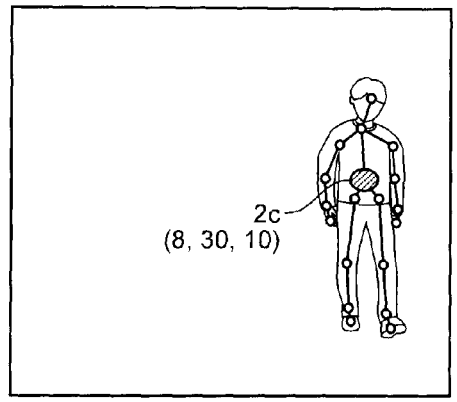
FIGS. 8A and 8B are drawings for explaining an example of a process performed by a position calculating circuitry according to the first embodiment.
Figure 8B:
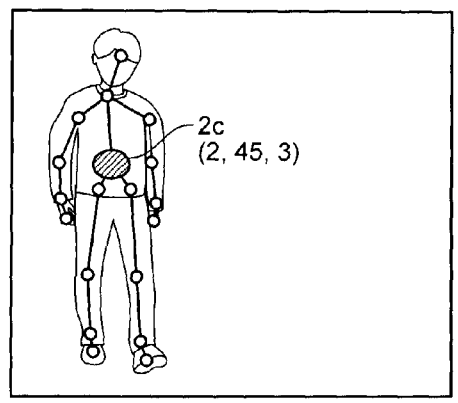

FIGS. 8A and 8B are drawings for explaining an example of the process performed by the position calculating circuitry 1402 according to the first embodiment. FIGS. 8A and 8B illustrate an example in which the pieces of motion information acquired by the motion information collecting circuitry 10a and the motion information collecting circuitry 10b during the walking training of the subject illustrated in FIG. 7A are brought into synchronization with each other. FIG. 8A schematically illustrates motion information of a certain frame acquired by the motion information collecting circuitry 10a. FIG. 8B schematically illustrates motion information of a frame acquired by the motion information collecting circuitry 10b at the same time as the frame shown in FIG. 8A.

For example, as illustrated in FIG. 8A, the position calculating circuitry 1402 first extracts coordinate information (8, 30, 10) of 2c corresponding to the lumbar joint in the certain frame acquired by the motion information collecting circuitry 10a. Further, as illustrated in FIG. 8B, the position calculating circuitry 1402 extracts coordinate information (2, 45, 3) of 2c corresponding to the lumbar joint in the frame acquired by the motion information collecting circuitry 10b at the same time as the frame shown in FIG. 8A.

To explain in other words with reference to FIG. 7A, for example, the position calculating circuitry 1402 extracts the coordinates (8, 30, 10) of 2c of the subject in the region R1 and the coordinates (2, 45, 3) of 2c of the subject in the region R2. After that, the position calculating circuitry 1402 calculates a relative relationship between the positions of the motion information collecting circuitry 10a and the motion information collecting circuitry 10b, on the basis of the two extracted sets of coordinates. For example, the position calculating circuitry 1402 calculates a relative relationship (2−8, 45−30, 3−10)=(−6, 15, −7) between the positions of the two motion information collecting circuitry 10a and 10b, from the two sets of coordinates (8, 30, 10) and (2, 45, 3) of 2c. After that, the position calculating circuitry 1402 stores information about the calculated relationship into the position information storage circuitry 1302 so as to be kept in correspondence with the motion information.

The configuration described above is merely an example. In other words, the positions extracted for the purpose of calculating the relative positions are not limited to the joint 2c corresponding to the lumbar. For example, it is acceptable to use other joints. Further, the elements extracted for the purpose of calculating the relative positions are not limited to joints. For example, it is acceptable to extract any arbitrary point included in each of the pieces of motion information. In this situation, the arbitrary point may be, for example, a predetermined guiding marker (e.g., parallel bars or a dumbbell used in exercise training, a wall, a doorknob, or a commonly-used item such as a light bulb (a light source)). In other words, the position calculating circuitry 1402 calculates the relative positions of the motion information collecting circuitry 10, by using a predetermined guiding marker included in each of the pieces of motion information acquired by the motion information collecting circuitry 10.

Returning to the description of FIG. 5, the display controlling circuitry 1403 is configured to cause the output circuitry 110 to output such output information in which the pieces of motion information are kept in association with one another, on the basis of the association information calculated by the position calculating circuitry 1402. More specifically, the display controlling circuitry 1403 causes the output circuitry 110 to output the output information in which the pieces of motion information are kept in synchronization with each other on the basis of the synchronization information calculated by the position calculating circuitry 1402. Even more specifically, the display controlling circuitry 1403 exercises control so as to cause the output circuitry 110 to display such display information in which the positions of the subject are aligned, on the basis of the synchronization information. Even more specifically, the display controlling circuitry 1403 causes the display information to be displayed in which the positions of the subject included in the pieces of motion information are aligned, by using the information about the relative positions stored in the position information storage circuitry 1302.

Figure 9:
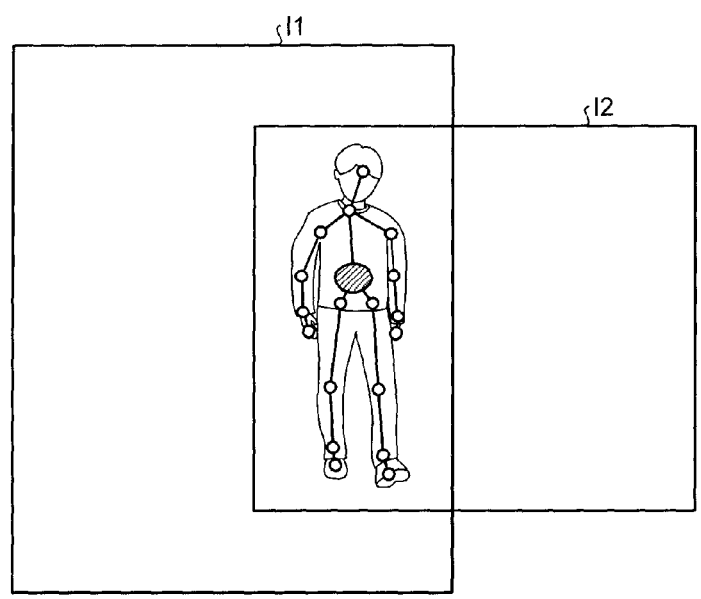
FIG. 9 is a drawing of an example of display information displayed by a display controlling circuitry according to the first embodiment.

FIG. 9 is a drawing of an example of the display information displayed by the display controlling circuitry 1403 according to the first embodiment. FIG. 9 illustrates an example in which color image information I1 acquired by the motion information collecting circuitry 10a and color image information I2 acquired by the motion information collecting circuitry 10b are displayed in such a manner that the positions thereof are aligned with each other. For example, the display controlling circuitry 1403 causes the output circuitry 110 to display a display image in which the color image information I1 and the color image information I2 are kept in synchronization (positional alignment) with each other by using the synchronization information calculated by the position calculating circuitry 1402.

For example, when the position calculating circuitry 1402 has calculated the relative relationship (−6, 15, −7) between the positions of the two motion information collecting circuitry 10, the display controlling circuitry 1403 causes the display image to be displayed in which the positions of the two pieces of color image information are aligned on mutually the same screen, by performing a position alignment process on the positions of the global coordinate systems of the motion information collecting circuitry 10, by using the calculated relative relationship (−6, 15, −7) and subsequently converting the global coordinate system into the distance image coordinate system. In other words, as illustrated in FIG. 9, the display controlling circuitry 1403 causes the output circuitry 110 to display the display image in which the color image information I1 is kept in synchronization with the color image information I2, by performing the position alignment process to align the position of the global coordinate system of the color image information I1 with the position of the global coordinate system of the color image information I2 while using the calculated relative relationship (−6, 15, −7) and subsequently converting the global coordinate system into the distance image coordinate system.

As a result, in the display information resulting from the position alignment process performed by the display controlling circuitry 1403, it is possible to display, as illustrated in FIG. 9, the manner in which the single subject is walking in a region obtained by putting together the color image information I1 and the color image information I2.

As explained above, the motion information processing apparatus 100 according to the first embodiment is able to display the pieces of motion information acquired by the plurality of motion information collecting circuitry 10 in such a manner that the positions thereof are aligned with one another. In other words, the motion information processing apparatus 100 is able to display the plurality of pieces of motion information acquired by the plurality of motion information collecting circuitry 10, so as to be put together into the one image. Accordingly, the motion information processing apparatus 100 is also able to display an image illustrated in FIGS. 10A and 10B.

Figure 10A:
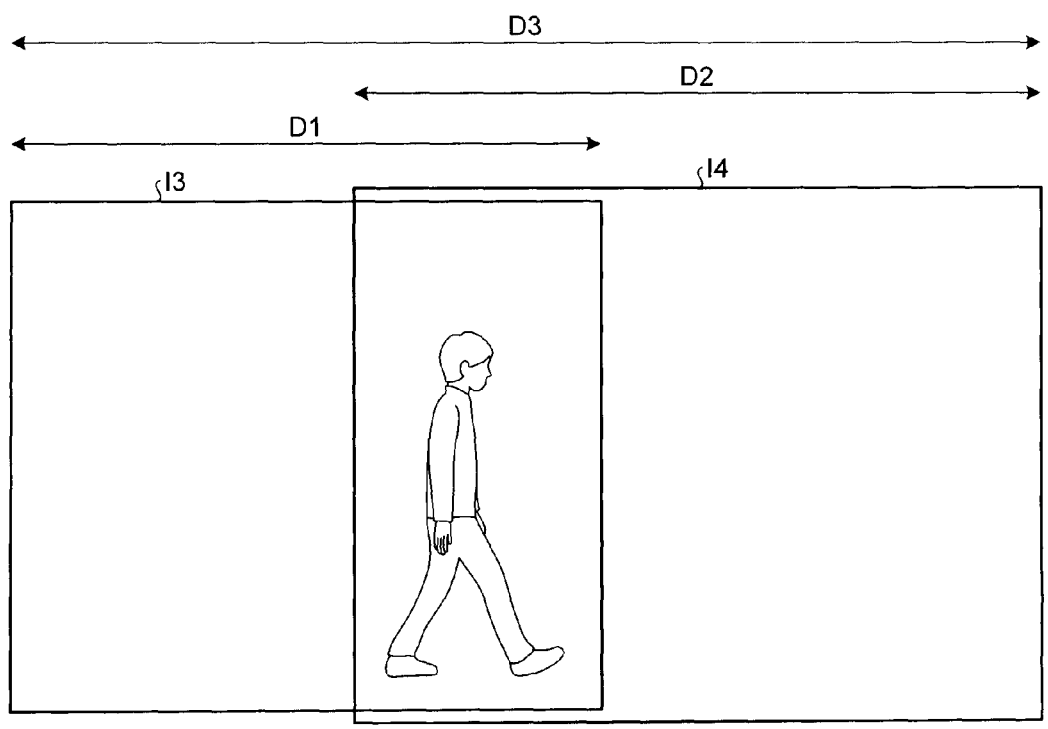
FIGS. 10A and B are drawings of other examples of the display information displayed by the display controlling circuitry according to the first embodiment.
Figure 10B:
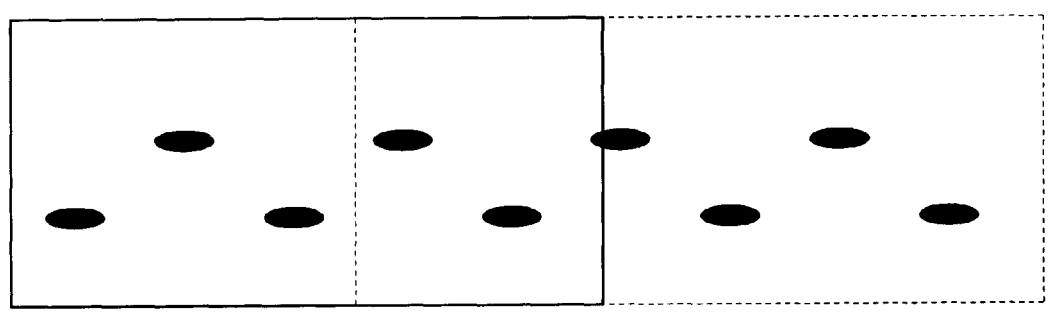

FIGS. 10A and 10B are drawings of other examples of the display information displayed by the display controlling circuitry 1403 according to the first embodiment. In FIGS. 10A and 10B, FIG. 10A illustrates an example of display information in which color image information I3 acquired by the motion information collecting circuitry 10*a* and color image information I4 acquired by the motion information collecting circuitry 10*b* are put together. The pieces of color image information in FIG. 10A are acquired by, for example, the plurality of motion information collecting circuitry 10 that are arranged as illustrated in FIG. 7D. Further, FIG. 10B illustrates another example of display information in which footprints are marked in the positions corresponding to information about landing points of the feet during the walking training of the subject rendered in the color image information illustrated in FIG. 10A. In other words, FIG. 10B illustrates a top view of the footprints of the subject illustrated in FIG. 10A.

For example, as illustrated in FIG. 7, the motion information collecting circuitry 10*a* and the motion information collecting circuitry 10*b* are arranged in a row on one side of the subject performing the walking training, so that the obtaining circuitry 1401 obtains the acquired pieces of motion information. Further, the position calculating circuitry 1402 calculates, as the synchronization information, information about relative positions of the motion information collecting circuitry 10*a* and the motion information collecting circuitry 10*b* on the basis of the obtained pieces of motion information. After that, the display controlling circuitry 1403 causes the output circuitry 110 to display the display information in which the color image information I3 and the color image information I4 are put together, as illustrated in FIG. 10A.

In other words, as illustrated in FIG. 10A, the display controlling circuitry 1403 causes the output circuitry 110 to display the display information indicating the manner in which the subject is performing the walking training, while using a width corresponding to a distance D3 resulting from putting together, through the position alignment process, a distance D1 in the transversal direction of the image taking region of the motion information collecting circuitry 10*a* and a distance D2 in the transversal direction of the image taking region of the motion information collecting circuitry 10*b*. Consequently, it is possible to obtain the information about the motion (e.g., the walking motion) of the subject in such a region that could not be acquired if a single motion information collecting circuitry 10 was used.

Further, as illustrated in FIG. 10B, the display controlling circuitry 1403 is also able to realize the display in which the analysis results obtained by analyzing the walking motion of the subject are put together. For example, as illustrated in FIG. 10B, the display controlling circuitry 1403 is able to realize the display in which the pieces of information about the landing points of the feet of the subject performing the walking training illustrated in FIG. 10A are put together.

In that situation, for example, the controlling circuitry 140 analyzes the landing points of the feet of the subject, on the basis of the motion information obtained by the obtaining circuitry 1401. In one example, the controlling circuitry 140 analyzes the positions of the landing points of the feet in the pieces of motion information obtained by the obtaining circuitry 1401. In other words, on the basis of the motion information (the coordinate information) acquired by the motion information collecting circuitry 10*a*, the controlling circuitry 140 calculates the coordinates of the positions of the landing points of the feet in the motion information. Similarly, on the basis of the motion information (the coordinate information) acquired by the motion information collecting circuitry 10*b*, the controlling circuitry 140 calculates the coordinates of the positions of the landing points of the feet in the motion information.

After that, the display controlling circuitry 1403 performs the position alignment process between the positions of the landing points of the feet calculated by the controlling circuitry 140, by using the synchronization information calculated by the position calculating circuitry 1402. Subsequently, the display controlling circuitry 1403 causes the output circuitry 110 to display the display information in which, as illustrated in FIG. 10B, the landing points of the feet are marked with the points of the footprints. With this arrangement, the display controlling circuitry 1403 is able to cause the information about the landing points of the feet to be displayed for the region of which the distance in the transversal direction is equal to D3.

The configuration described above is merely an example, and possible embodiments are not limited to this example. In other words, the information displayed as the display information is not limited to the ones illustrated in the drawings. For example, it is possible to apply the present disclosure to any type of information, as long as the information is displayed by using the coordinates of the skeleton information. In other words, the present disclosure is applicable even to a situation in which the position of a joint corresponding to a site of a body of a subject (e.g., the head) is indicated linear over the color image information.

For example, on the basis of the motion information obtained by the obtaining circuitry 1401, it is possible to display, as the display information, locus information indicating the positions of the landing points of the feet of the subject or superimposed image information obtained by superimposing information about the angle of a predetermined site of the body of the subject on the color image information. In this situation, the angle of the predetermined site is at least one of the following: a rotation angle indicating swaying of the subject in the back-and-forth directions with respect to the advancing direction; and a rotation angle indicating swaying of the subject in the up-and-down direction. In other words, the angle of the predetermined site represents the rotation angle around an axis in the vertical (upright) direction and the rotation angle around an axis in the advancing direction. In this situation, the angle may be, for example, the angle indicating the orientation of the shoulders or the orientation of the lumbar.

Further, on the basis of the motion information obtained by the obtaining circuitry 1401, it is possible to display, as the display information, locus information indicating a locus of the moving from one place to another (hereinafter, "spatial move") of the subject, in addition to the locus of the positions of the landing points of the feet. In this situation, the locus of the spatial move of the subject is a locus of a spatial move of a characteristic position of the subject. Further, the characteristic position is at least one of the following: the position of a predetermined site of the subject; a position calculated by using the positions of a plurality of sites; a plurality of center positions of the subject; and the position of a gravity point of the subject.

For example, in the space from which the motion information collecting circuitry 10 are able to acquire the motion information, the display controlling circuitry 1403 causes the output circuitry 110 to display locus information including at least one of the following: a locus of the landing points of the feet; a locus of a spatial move of the body; and the angle of a predetermined site of the body. The display controlling circuitry 1403 is able to cause display information to be displayed in which the locus information is viewed from above, viewed from a side, or as a bird's eye view. In one example, the display controlling circuitry 1403 causes the output circuitry 110 to display locus information indicating, on an x-y plane acquired during the walking training of the subject, footprints of the left and the right feet, a locus of the gravity point of the body, and line segments connecting together the joints corresponding to the left and the right shoulders.

In this situation, it is possible to display the information about the footprints, the information about the locus of the spatial move of the body, and the information about the line segments in a distinguishable manner. For example, by varying the color or the like of the footprints, the display controlling circuitry 1403 is able to distinguish the footprints of the right foot from the footprints of the left foot, to distinguish the number of steps, or to distinguish different states of the walk of the subject (e.g., whether the walk is stable or not).

Further, the display controlling circuitry 1403 is also able to cause the output circuitry 110 to display, as the display information, superimposed image information obtained by superimposing various types of information on the color image information obtained by the obtaining circuitry 1401. More specifically, the display controlling circuitry 1403 causes the superimposed image information obtained by superimposing information about the angle of a predetermined site of the body of the subject on the color image information to be displayed as the display information. For example, the display controlling circuitry 1403 causes the superimposed image information to be displayed as the display information, in which a straight line connecting arbitrary positions (e.g., joints or predetermined positions of a predetermined bone) of the subject together is superimposed on the color image information.

In this situation, besides the straight line, the display controlling circuitry 1403 is also able to display information in which a predetermined reference element (e.g., a line segment indicating the vertical direction or the horizontal direction) is superimposed at the same time. In other words, the display controlling circuitry 1403 causes superimposed image information to be displayed in which movements of a predetermined site of the subject with respect to a predetermined reference element are indicated. Further, the display controlling circuitry 1403 is also able to cause superimposed image information to be displayed in which a locus of the positions of a predetermined site of the subject obtained while the subject is performing a motion is superimposed on the color image information. In other words, the display controlling circuitry 1403 causes the superimposed image information to be displayed in which a curve indicating the locus of the predetermined site is superimposed on the color image information.

Further, the display controlling circuitry 1403 causes the output circuitry 110 to display, as the display information, information about the angle of a predetermined site of the subject (e.g., a chart indicating chronological changes in the angle of an elbow joint, a chart indicating chronological changes in the angle of the body axis of the subject with respect to the vertical direction). Further, the display controlling circuitry 1403 may cause other information to be displayed as the display information such as a chart indicating velocity information or a chart indicating acceleration information of a predetermined site of the subject.

Further, in the description above, the example is explained in which the plurality of pieces of motion information are brought into synchronization with one another, on the basis of the position of a predetermined site (e.g., the joint corresponding to the lumbar) or the position of an object such as parallel bars, included in each of the pieces of motion information; however, possible embodiments are not limited to this example. For instance, the viewer may make a designation. In that situation, the input circuitry 120 receives information about a reference element to be used for bringing the plurality of pieces of motion information into synchronization with one another.

Figure 11A:
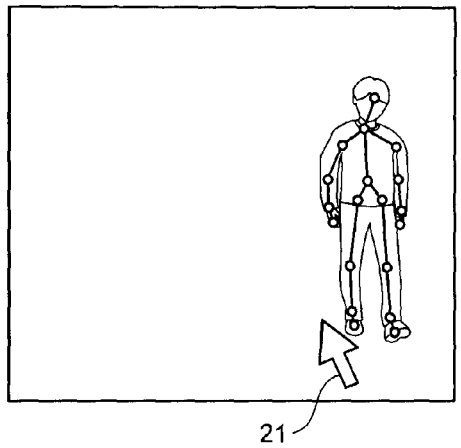
FIGS. 11A and B are drawings for explaining a modification example of a synchronization between pieces of motion information according to the first embodiment.
Figure 11B:
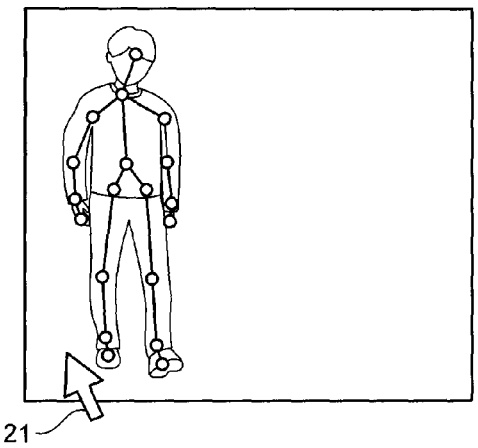

FIGS. 11A and 11B are drawings for explaining a modification example of the synchronization between the pieces of motion information according to the first embodiment. In FIGS. 11A and 11B, FIG. 11A illustrates color image information acquired by the motion information collecting circuitry 10a, whereas FIG. 11B illustrates color image information acquired by the motion information collecting circuitry 10b. For example, as illustrated in FIG. 11A, when a position near a foot of the subject is clicked while an arrow 21 is pointing thereto, the input circuitry 120 receives the position as information about a reference element to be used for the synchronization. Similarly, as illustrated in FIG. 11B, when a position near a foot of the subject is clicked while the arrow 21 is pointing thereto, the input circuitry 120 receives the position as information about a reference element corresponding to the information about the reference element that was received immediately prior.

In this situation, when the input circuitry 120 has received information about a reference element for each of the pieces of motion information, the position calculating circuitry 1402 calculates the synchronization information on the basis of the coordinate information of the information about each reference element. After that, the display controlling circuitry 1403 causes the output circuitry 110 to display such display information that results from a position alignment process performed by using the synchronization information calculated by the position calculating circuitry 1402.

In the description above, the example is explained in which the plurality of pieces of motion information are brought into synchronization with each other, on the basis of the relative positional relationship of the subject or the predetermined guiding marker; however, possible embodiments are not limited to this example. For instance, another arrangement is acceptable in which the pieces of motion information are brought into synchronization with each other by using absolute value information based on a fixed element included in each of the plurality of pieces of motion information. In that situation, for example, a position alignment process is performed on a fixed position marker included in each of the pieces of color image information acquired by the motion information collecting circuitry 10a and the motion information collecting circuitry 10b, on the basis of the absolute coordinates of the position markers. In other words, the pieces of motion information are brought into synchronization with each other, by performing the position alignment process on the motion information acquired by the motion information collecting circuitry 10*a* and the motion information acquired by the motion information collecting circuitry 10*b*, on the basis of the absolute coordinates of the fixed position marker included in each of the two pieces of motion information. To bring the pieces of motion information into synchronization with each other by using the absolute coordinates of the fixed position markers, a calibration process is performed on a regular basis, in relation to the coordinate conversion between the coordinates of the fixed position markers acquired by the motion information collecting circuitry 10*a* and the motion information collecting circuitry 10*b* and the absolute coordinates assigned in advance. Further, although the position markers are used for the synchronization of the motion information in the description above, it is also acceptable to bring the pieces of motion information into synchronization with each other by obtaining a positional relationship between the motion information collecting circuitry 10 by determining installment positions of the plurality of motion information collecting circuitry 10 in advance, so that the motion information collecting circuitry 10 are arranged in the determined installment positions.

In the description above, the example is explained in which the pieces of motion information are brought into synchronization with each other by using the information about the reference element designated by the operator; however, possible embodiments are not limited to this example. For instance, the motion information collecting circuitry 10*a* and the motion information collecting circuitry 10*b* may be arranged in positions that are determined in advance. In that situation, the positional relationship of a predetermined object included in the pieces of motion information acquired by the motion information collecting circuitry 10*a* and the motion information collecting circuitry 10*b* is constant at all times. Thus, it is acceptable to bring the pieces of motion information into synchronization with each other by using the constant positional relationship.

Figure 12:
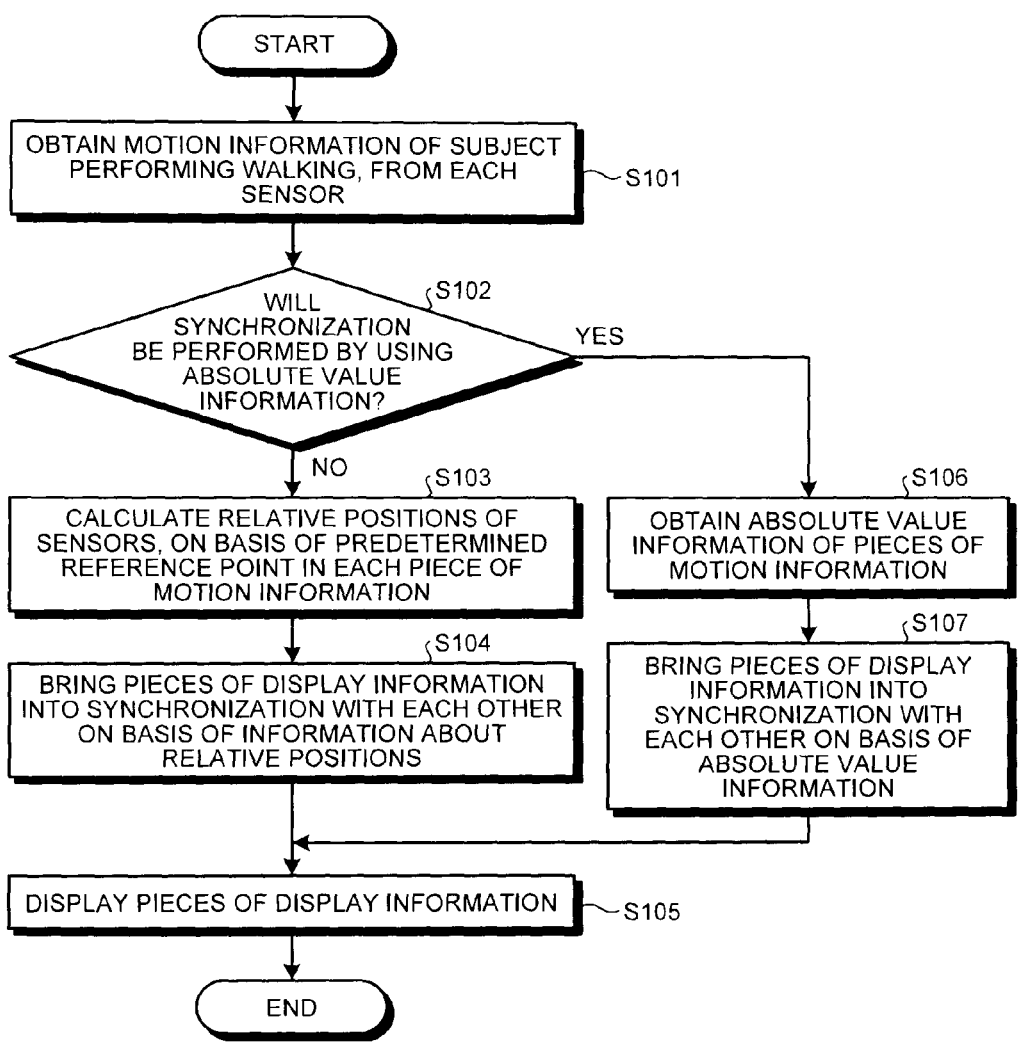
FIG. 12 is a flowchart of a procedure in a process performed by the motion information processing apparatus according to the first embodiment.

Next, a process performed by the motion information processing apparatus 100 according to the first embodiment will be explained, with reference to FIG. 12. FIG. 12 is a flowchart of a procedure in the process performed by the motion information processing apparatus 100 according to the first embodiment. FIG. 12 illustrates an example in which walking training is performed as rehabilitation.

As illustrated in FIG. 12, in the motion information processing apparatus 100 according to the first embodiment, when walking training is started, the obtaining circuitry 1401 obtains motion information of the subject performing the walking training from each of the sensors (step S101). In other words, the obtaining circuitry 1401 obtains the plurality of pieces of motion information acquired by the plurality of sensors, from the motion information storage circuitry 1301.

After that, the position calculating circuitry 1402 judges whether a synchronization process will be performed by using absolute value information (step S102). In one example, the position calculating circuitry 1402 determines that the synchronization process will be performed by using absolute value information, if the pieces of motion information acquired by the motion information collecting circuitry 10 include information about, for example, a fixed position marker that has information about the absolute coordinates. Alternatively, another arrangement is also acceptable in which the position calculating circuitry 1402 determines that the synchronization process will be performed by using absolute value information, if the operator has so designated in advance.

If it has been determined that the synchronization process will not be performed by using the absolute value information (step S102: No), the position calculating circuitry 1402 calculates relative positions of the sensors, on the basis of a predetermined reference point in each of the obtained pieces of motion information (step S103). After that, the display controlling circuitry 1403 brings pieces of display information into synchronization with each other on the basis of the information about the relative positions (step S104), and exercises control so as to cause the output circuitry 110 to display the pieces of display information brought into synchronization with each other (step S105).

On the contrary, if it has been determined at step S102 that the synchronization process will be performed by using the absolute value information (step S102: Yes), the position calculating circuitry 1402 obtains the absolute value information of each of the pieces of motion information (step S106). After that, the display controlling circuitry 1403 brings pieces of display information into synchronization with each other on the basis of the absolute value information (step S107) and causes the pieces of display information to be displayed (step S105).

As explained above, according to the first embodiment, the obtaining circuitry 1401 obtains the pieces of motion information of the subject acquired from the mutually-different positions with respect to the subject undergoing the rehabilitation. The position calculating circuitry 1402 calculates the synchronization information used for bringing the pieces of motion information obtained by the obtaining circuitry 1401 into synchronization with each other. On the basis of the synchronization information calculated by the position calculating circuitry 1402, the display controlling circuitry 1403 exercises control so as to cause the output circuitry 110 to output the output information in which the pieces of motion information are kept in synchronization with each other. Consequently, the motion information processing apparatus 100 according to the first embodiment is able to provide viewers with the single piece of display information in which the plurality of pieces of motion information are kept in synchronization with each other. Thus, the motion information processing apparatus 100 makes it possible to obtain the detailed information about the motions of the subject undergoing the rehabilitation. As a result, the motion information processing apparatus 100 according to the first embodiment enables medical doctors, physiotherapists, and the like to evaluate the rehabilitation with a higher level of precision.

Further, according to the first embodiment, the position calculating circuitry 1402 calculates the synchronization information, on the basis of the predetermined position included in each of the plurality of pieces of motion information obtained by the obtaining circuitry 1401. Consequently, the motion information processing apparatus 100 according to the first embodiment makes it possible to easily perform the position alignment process with a high level of precision.

Further, according to the first embodiment, the position calculating circuitry 1402 calculates the synchronization information by using the relative relationship or the absolute values of the predetermined position included in each of the plurality of pieces of motion information obtained by the obtaining circuitry 1401. Consequently, the motion information processing apparatus 100 according to the first embodiment makes it possible to bring the pieces of motion information into synchronization with each other, by using any of the various types of information included in the motion information.

Further, according to the first embodiment, the obtaining circuitry 1401 obtains the pieces of motion information of the subject acquired from the plurality of positions in one of the following: a direction that is parallel to the advancing direction of the subject; a direction that forms a predetermined angle with the advancing direction; and a direction that is orthogonal to the advancing direction. Consequently, the motion information processing apparatus 100 according to the first embodiment makes it possible to easily apply the present disclosure to any ordinary use case.

Further, according to the first embodiment, the display controlling circuitry 1403 exercises control so as to cause the output circuitry 110 to output the display information that includes one of the following generated on the basis of the motion information of the subject performing the walking motion: the locus information indicating the locus of the spatial move of the predetermined site of the subject; the velocity information at the predetermined site; and the angle information of the predetermined site of the subject. Consequently, with regard to the walking training of the subject, the motion information processing apparatus 100 according to the first embodiment makes it possible to provide not only the synchronization information, but also the detailed evaluation of the walking.

Second Embodiment

In the first embodiment described above, the example is explained in which the position alignment process is performed on the plurality of pieces of motion information by using the coordinates of the reference point (e.g., the joint corresponding to the lumbar or a designated object) in the predetermined frame included in each of the pieces of motion information. In a second embodiment, an example will be explained in which a position alignment process is performed on the basis of chronological changes in the position of a reference point included in each of the pieces of motion information. In the second embodiment, specifics of processes performed by the position calculating circuitry 1402 and the display controlling circuitry 1403 are different from those in the first embodiment. The second embodiment will be explained below while a focus is placed on the different processes.

The position calculating circuitry 1402 according to the second embodiment is configured to calculate synchronization information on the basis of chronological changes in the position of a reference point included in each of the plurality of pieces of motion information obtained by the obtaining circuitry 1401. More specifically, the position calculating circuitry 1402 calculates a positional relationship and orientations of the motion information collecting circuitry 10 on the basis of moves of the coordinates of the predetermined reference point (e.g., the joint corresponding to the lumbar) of the subject undergoing rehabilitation.

Figure 13A:
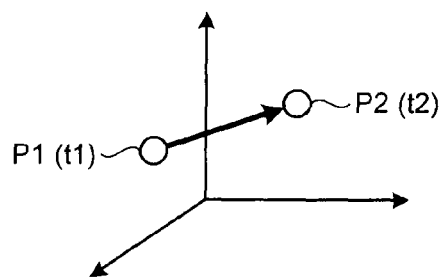
FIGS. 13A and 13B are drawings for explaining an example of a process performed by a position calculating circuitry according to a second embodiment.
Figure 13B:
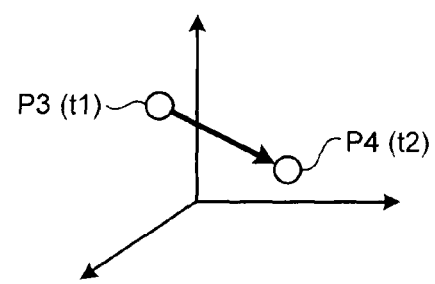

FIGS. 13A and 13B are drawings for explaining an example of a process performed by the position calculating circuitry 1402 according to the second embodiment. In FIGS. 13A and 13B, FIG. 13A illustrates a move of the coordinates of the reference point in the motion information acquired by the motion information collecting circuitry 10a, whereas FIG. 13B illustrates a move of the coordinates of the reference point in the motion information acquired by the motion information collecting circuitry 10b.

For example, as illustrated in FIG. 13A, the position calculating circuitry 1402 calculates a change in the coordinates from coordinates P1 of the reference point at a time "t1" to coordinates P2 of the reference point at a time "t2", in the motion information acquired by the motion information collecting circuitry 10a. Similarly, as illustrated in FIG. 13B, the position calculating circuitry 1402 calculates a change in the coordinates from coordinates P3 of the reference point at the time "t1" to coordinates P4 of the reference point at the time "t2", in the motion information acquired by the motion information collecting circuitry 10b.

In this situation, in the real space, the arrows illustrated in FIGS. 13A and 13B are assumed to move in mutually the same direction by mutually the same distance. Accordingly, it is possible to calculate the positional relationship with which the motion information collecting circuitry 10a and the motion information collecting circuitry 10b are arranged, on the basis of the orientations of the arrows. In other words, the position calculating circuitry 1402 calculates the positional relationship between the motion information collecting circuitry 10a and the motion information collecting circuitry 10b on the basis of the moves of the coordinates of the reference point in the pieces of motion information. After that, the position calculating circuitry 1402 stores the calculated information about the positional relationship into the position information storage circuitry 1302 so as to be kept in correspondence with the motion information.

Figure 14:
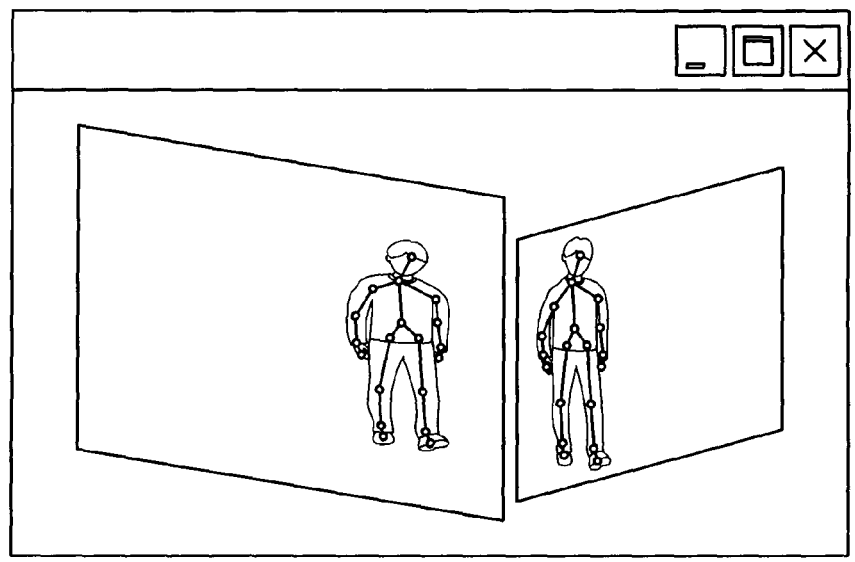
FIG. 14 is a drawing of an example of display information displayed by a display controlling circuitry according to the second embodiment.

The display controlling circuitry 1403 according to the second embodiment is configured to exercise control so as to cause display information to be output in which two-dimensional images rendered by the mutually-different pieces of motion information are arranged in positions corresponding to the positional relationship calculated by the position calculating circuitry 1402, within a virtual space on a display screen of the output circuitry 110. FIG. 14 is a drawing of an example of the display information displayed by the display controlling circuitry 1403 according to the second embodiment.

For example, as illustrated in FIG. 14, the display controlling circuitry 1403 causes the display information to be displayed in which the two-dimensional images are arranged in a virtual three-dimensional space in a display window. In this situation, as illustrated in FIG. 14, the display controlling circuitry 1403 causes the display information to be displayed in which the pieces of two-dimensional color image information are arranged in the positions corresponding to the positional relationship calculated by the position calculating circuitry 1402, by using the left-side image (the color image information acquired by the motion information collecting circuitry 10a) and the right-side image (the color image information acquired by the motion information collecting circuitry 10b). In other words, the display controlling circuitry 1403 arranges the pieces of two-dimensional color image information in such positions that reflect the positional relationship with which the motion information collecting circuitry 10a and the motion information collecting circuitry 10b are arranged.

The display information described above is merely an example. It is possible to cause various types of display information to be displayed, by using the positional relationship calculated by the position calculating circuitry 1402. For example, the display controlling circuitry 1403 is able to cause display information to be displayed in which positions of the subject are aligned on the basis of the calculated positional relationship. Further, the display controlling circuitry 1403 is also able to cause display information to be displayed in which pieces of two-dimensional color image information are arranged, not only in the positions corresponding to the positional relationship calculated by the position calculating circuitry 1402, but also in positions corresponding to a positional relationship that is set in advance.

As described above, according to the second embodiment, the position calculating circuitry 1402 calculates, as the synchronization information, the positional relationship between the positions from which the plurality of pieces of motion information are acquired, by comparing the moves of the predetermined position with each other, the predetermined position being included in each of the plurality of pieces of motion information obtained by the obtaining circuitry 1401. Consequently, the motion information processing apparatus 100 according to the second embodiment is able to calculate the synchronization information corresponding to the movements of the subject and thus makes it possible to perform the position alignment process with a higher level of precision.

Further, according to the second embodiment, the display controlling circuitry 1403 exercises control so as to cause the display information to be output in which the images rendered by the mutually-different pieces of motion information are arranged in the positions corresponding to the positional relationship calculated by the position calculating circuitry 1402, on the display screen of the output circuitry 110. Consequently, the motion information processing apparatus 100 according to the second embodiment makes it possible to cause such display information to be displayed that reflects the positional relationship between the motion information collecting circuitry 10.

Third Embodiment

In the first and the second embodiments described above, the example is explained in which the positions and the times of the pieces of motion information are brought into synchronization with each other. In a third embodiment, an example will be explained in which, when the plurality of pieces of motion information acquired by the plurality of motion information collecting circuitry 10 are displayed, the pieces of motion information are displayed in such a manner that the times thereof are kept in synchronization with each other. In the third embodiment, specifics of processes performed by the display controlling circuitry 1403 are different from those in the first and the second embodiments. Thus, the third embodiment will be explained below while a focus is placed on the different processes.

Figure 15:
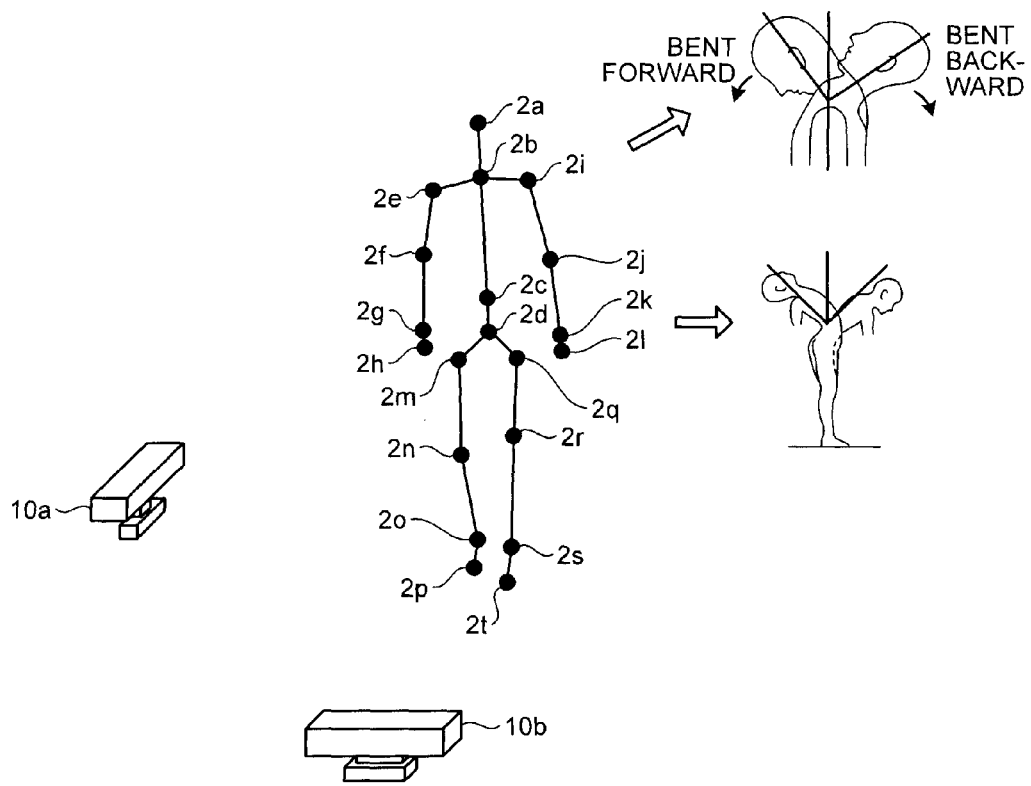
FIG. 15 is a drawing for explaining an example of display information displayed by a display controlling circuitry according to a third embodiment.

The display controlling circuitry 1403 according to the third embodiment is configured to exercise control so as to cause the output circuitry 110 to display the plurality of pieces of motion information obtained by the obtaining circuitry 1401, in a time series while the times thereof are kept in synchronization with each other. FIG. 15 is a drawing for explaining an example of display information displayed by the display controlling circuitry 1403 according to the third embodiment.

For example, as illustrated in FIG. 15, the display controlling circuitry 1403 displays motion information acquired by the motion information collecting circuitry 10b arranged in front of the subject and motion information acquired by the motion information collecting circuitry 10a arranged on a side of the subject, in such a manner that the times thereof are kept in synchronization with each other. In this situation, for example, as illustrated in FIG. 15, the subject is performing exercise to bend the neck forward and backward, exercise to bend the lumbar forward and backward, or the like.

Figure 16:
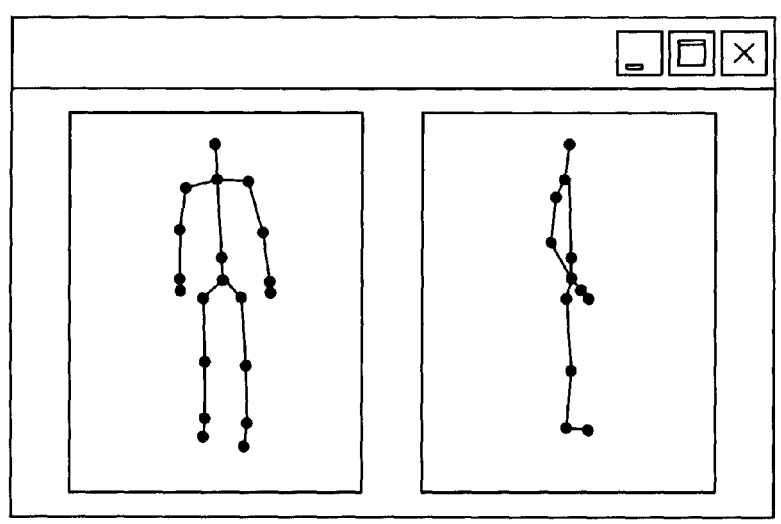
FIG. 16 is a drawing of an exemplary display of the display information displayed by the display controlling circuitry according to the third embodiment.

FIG. 16 is a drawing of an exemplary display of the display information displayed by the display controlling circuitry 1403 according to the third embodiment. For example, as illustrated in FIG. 16, the display controlling circuitry 1403 causes the output circuitry 110 to display such display information in which color image information from the front of the subject (the color image information acquired by the motion information collecting circuitry 10b) is arranged on the left side of a display window and in which color image information from the side of the subject (the color image information acquired by the motion information collecting circuitry 10a) is arranged on the right side of the display window. In this situation, the display controlling circuitry 1403 causes the pieces of color image information corresponding to the pieces of motion information to be displayed in the regions while being kept in synchronization with each other according to the times of the frames. As a result, the motion information processing apparatus 100 according to the third embodiment is able to provide viewers with the pieces of color image information obtained as the subject is being viewed from the plurality of angles in such a manner that the times thereof are kept in synchronization with each other. Thus, the viewers are able to obtain detailed information about the motions of the subject undergoing the rehabilitation.

Fourth Embodiment

The first to the third embodiments have thus been explained. The present disclosure, however, may be carried out in other various embodiments besides the first to the third embodiments described above.

In the first to the third embodiments described above, the examples are explained in which the number of motion information collecting circuitry 10 is two; however, possible embodiments are not limited to these examples. For instance, three or more motion information collecting circuitry 10 may be used. In that situation, the obtaining circuitry 1401 obtains pieces of motion information acquired by the motion information collecting circuitry 10. After that, the position calculating circuitry 1402 calculates the synchronization information for the synchronization among the pieces of motion information. Subsequently, the display controlling circuitry 1403 causes the pieces of motion information to be displayed while being kept in synchronization with one another on the basis of the calculated synchronization information.

In the third embodiment described above, the example is explained in which the plurality of pieces of motion information are displayed in the plurality of regions in such a manner that the times thereof are kept in synchronization with each other; however, possible embodiments are not limited to this example. For instance, another arrangement is acceptable in which, while the times thereof are kept in synchronization with each other, display information is also varied in accordance with movements of the subject.

Figure 17A:
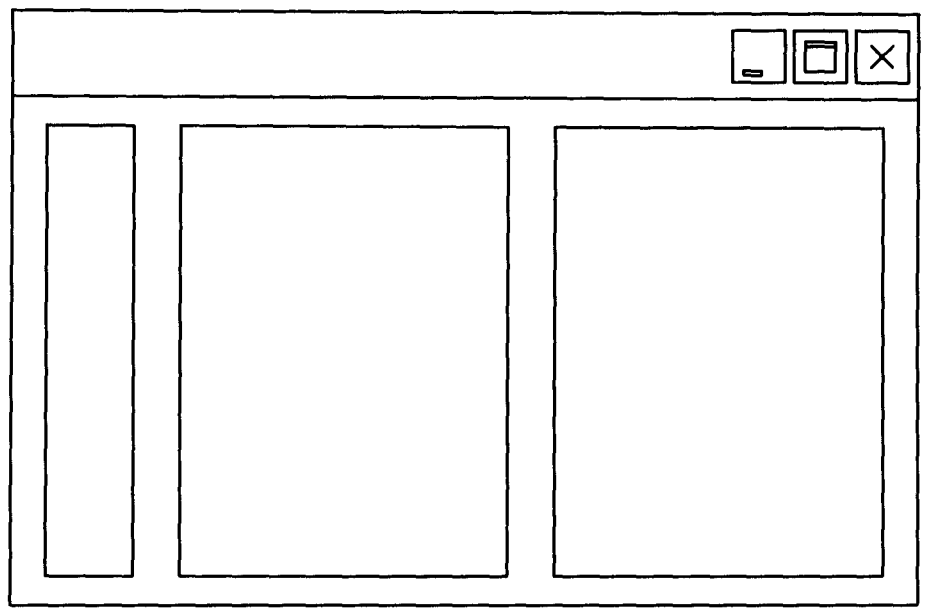
FIG. 17A is a drawing for explaining an example of display information controlled by a display controlling circuitry according to a fourth embodiment.
Figure 17B:
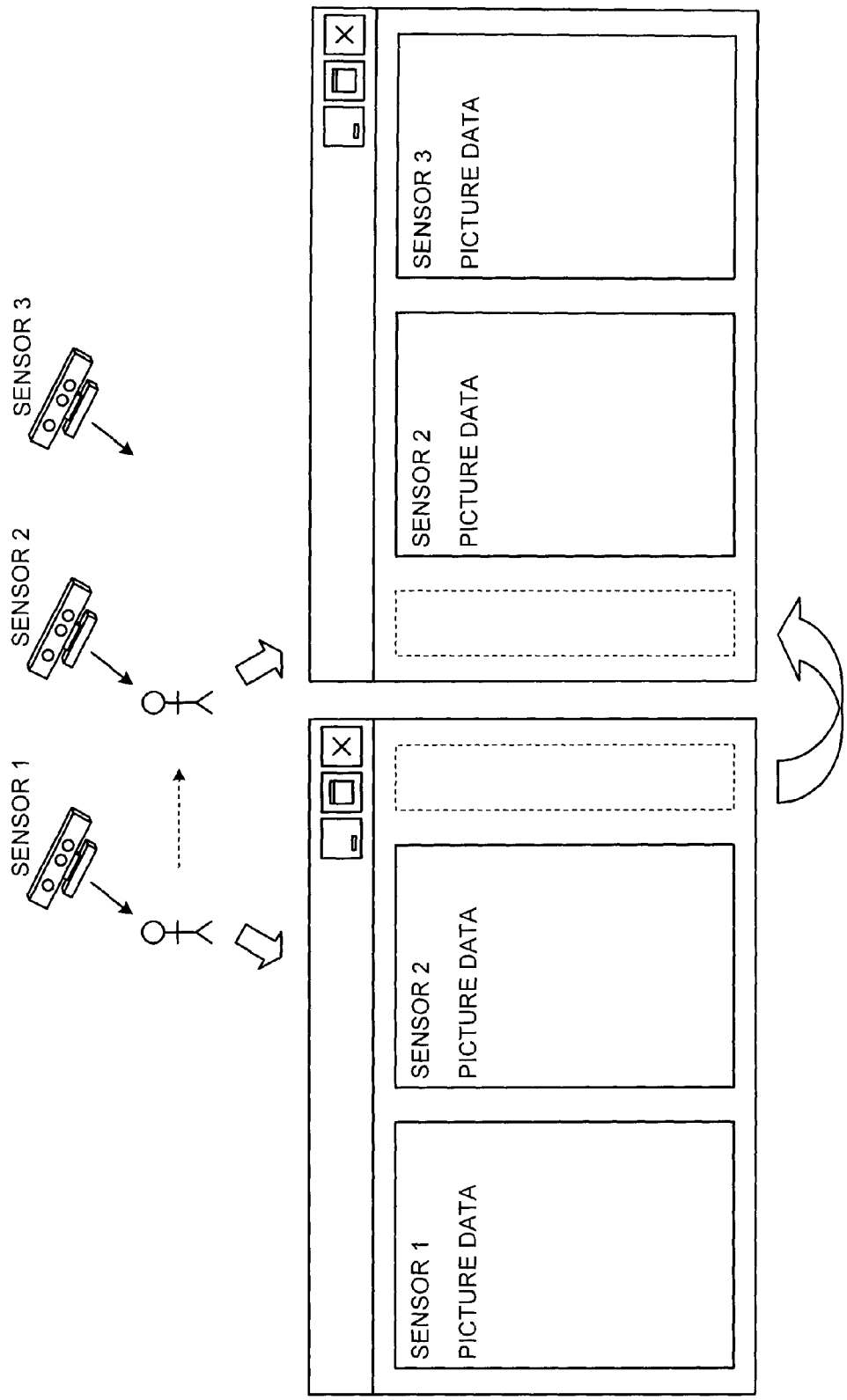
FIG. 17B is a drawing for explaining another example of the display information controlled by the display controlling circuitry according to the fourth embodiment.

The display controlling circuitry 1403 according to a fourth embodiment is configured to vary display information that is used when displaying a plurality of pieces of motion information, in accordance with movements of the subject included in the pieces of motion information. FIGS. 17A and 17B are drawings for explaining an example of the display information controlled by the display controlling circuitry 1403 according to the fourth embodiment. In this situation, FIGS. 17A and 17B illustrate the example in which pieces of motion information are acquired by arranging three motion information collecting circuitry 10 on a side of a subject performing walking training. Further, FIGS. 17A and 17B illustrate the example in which pieces of color image information corresponding to the acquired pieces of motion information are displayed.

For example, as illustrated in FIG. 17A, the display controlling circuitry 1403 causes display information to be displayed, the display information being provided with display regions used for displaying the pieces of color image information acquired by the motion information collecting circuitry 10 in a display window. For example, as illustrated in FIG. 17A, the display controlling circuitry 1403 causes the display information to be displayed in which three display regions each corresponding to a different one of the three motion information collecting circuitry 10 are arranged in a row in the transversal direction according to the positional arrangement of the motion information collecting circuitry 10. In this situation, for example, as illustrated in FIG. 17B, to display a walk of the subject walking from the left side to the right side of the drawing, the display controlling circuitry 1403 varies the display regions in the display window in accordance with the spatial move of the subject.

In one example, as illustrated in FIG. 17B, while the subject is passing the vicinity of a sensor 1, the display controlling circuitry 1403 exercises control so that a display region for displaying the color image information acquired by the sensor 1, which is currently positioned closest to the subject, and a display region for displaying the color image information acquired by a sensor 2, which will subsequently be approached by the subject, are displayed in a larger size. After that, while the subject is passing the vicinity of the sensor 2, the display controlling circuitry 1403 exercises control so that, as illustrated in FIG. 17B, the display region for displaying the color image information acquired by the sensor 2, which is currently positioned closest to the subject, and a display region for displaying the color image information acquired by a sensor 3, which will subsequently be approached by the subject, are displayed in a larger size. In this manner, the display controlling circuitry 1403 realizes the display so as to emphasize the color image information in the region in which the image of the subject is rendered in a large size, in accordance with the spatial move of the subject. As for the emphasized display, it is also possible to exercise control in such a manner that a single region is displayed in the entire display window. In other words, the display controlling circuitry 1403 may extract a piece of motion information in which the image of the subject is currently rendered in the largest size and may cause the display region displaying the extracted piece of motion information to be displayed in an enlarged manner in the entire display window.

Further, as other examples of the emphasized display, the display controlling circuitry 1403 is also able to arrange a region to be emphasized to be positioned at the center of the display window or to display the frame of a region to be emphasized in color. Further, the display controlling circuitry 1403 is also able to realize a display that enables the viewer to understand whether the motion information collecting circuitry 10 has been arranged. For example, as illustrated in FIG. 17B, the display controlling circuitry 1403 is able to enable the viewer to understand the positional arrangement state of the motion information collecting circuitry 10, by causing a small display region to be displayed on the side where another motion information collecting circuitry 10 is positioned (i.e., the right end of the display window on the left side or the left end of the display window on the right side).

The display information illustrated in FIGS. 17A and 17B is merely an example. For instance, the positional arrangement of the display regions is not limited to the one in the transversal direction, and the display regions may be displayed while being arranged in a longitudinal direction or a diagonal direction. In that situation, the display regions may be arranged so as to reflect the actual positional arrangement state of the motion information collecting circuitry 10.

Figure 18A:
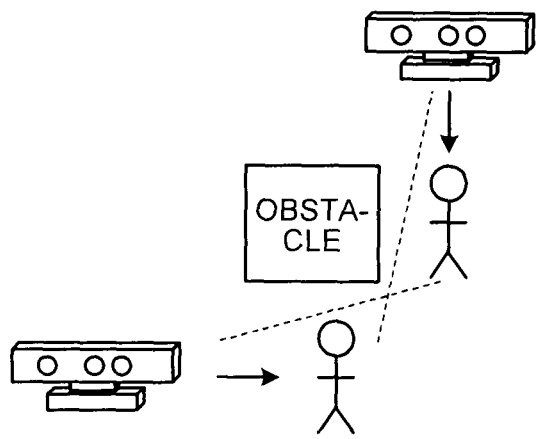
FIG. 18A is a drawing of an exemplary positional arrangement of motion information collecting circuitry according to the fourth embodiment.
Figure 18B:
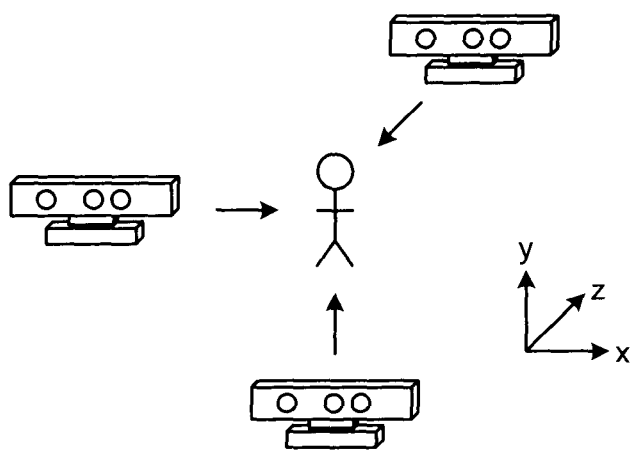
FIG. 18B is a drawing of another exemplary positional arrangement of the motion information collecting circuitry according to the fourth embodiment.

Further, the positional arrangements of the motion information collecting circuitry 10 described in the first to the third embodiments above are merely examples. It is possible to apply the present disclosure to any of various use cases, depending on the status of the subject. FIGS. 18A and 18B are drawings of other exemplary positional arrangements of the motion information collecting circuitry 10 according to the fourth embodiment. For example, as illustrated in FIG. 18A, the motion information collecting circuitry 10 may be arranged so as to comprehensively cover the motion information of the walking training of the subject in a motion space in which an obstacle is present. In other words, the motion information collecting circuitry 10 are able to thoroughly acquire the motion information of the subject undergoing the rehabilitation in the motion space where the obstacle may create a blind spot. That is to say, it is possible to eliminate the blind spot for the subject undergoing the rehabilitation.

Further, as illustrated in FIG. 18B, for example, the motion information collecting circuitry 10 may be arranged so as to acquire the motion information of the subject from the depth direction (the longitudinal direction), the horizontal direction (the transversal direction), and the vertical direction (the up-and-down direction). In other words, the motion information collecting circuitry 10 may be arranged so as to acquire the motion information of the subject from every direction. With this arrangement, it is possible to meet various demands of the viewer.

Further, in the first to the third embodiments described above, the examples are explained in which the number of motion information collecting circuitry 10 is two or three. However, possible embodiments are not limited to these examples. For instance, four or more motion information collecting circuitry may be arranged.

In the first embodiment described above, the example is explained in which the motion information processing apparatus 100 obtains the motion information of the subject undergoing the rehabilitation and displays the display information; however, possible embodiments are not limited to this example. For instance, the processes may be performed by a service providing apparatus connected to a network.

FIG. 19 is a diagram for explaining an example in which an aspect of the present disclosure is applied to a service providing apparatus according to the fourth embodiment. As illustrated in FIG. 19, a service providing apparatus 200 is provided in a service center and is connected to, for example, terminal apparatuses 300 that are provided in a medical institution, a home, and an office, via a network 5. To each of the terminal apparatuses 300 provided at the medical institution, the home, and the office, at least one motion information collecting circuitry 10a and at least one motion information collecting circuitry 10b are connected. Further, each of the terminal apparatuses 300 has a client function used for utilizing services provided by the service providing apparatus 200. It should be noted that, although FIG. 19 illustrates only the two motion information collecting circuitry 10, in actuality, any arbitrary number of motion information collecting circuitry 10 (depending on various use cases) may be connected to each of the terminal apparatuses 300.

The service providing apparatus 200 is configured to provide, as the services, each of the terminal apparatuses 300 with the same processes as those of the motion information processing apparatus 100. In other words, the service providing apparatus 200 includes functional circuitry that are equivalent to the obtaining circuitry 1401, the position calculating circuitry 1402, and the display controlling circuitry 1403. Further, the functional circuitry equivalent to the obtaining circuitry 1401 is configured to obtain pieces of motion information of a subject acquired from mutually-different positions with respect to the subject undergoing rehabilitation. Further, the functional circuitry equivalent to the position calculating circuitry 1402 is configured to calculate the synchronization information used for bringing the pieces of motion information obtained by the functional circuitry equivalent to the obtaining circuitry 1401 into synchronization with each other. Further, the functional circuitry equivalent to the display controlling circuitry 1403 is configured to exercise control so as to cause a monitor of each of the terminal apparatuses 300 to output the output information in which the pieces of motion information are kept in synchronization with each other, on the basis of the synchronization information calculated by the functional circuitry equivalent to the position calculating circuitry 1402. The network 5 may be wired or wireless and may be configured with an arbitrary type of communication network such as the Internet, a Wide Area Network (WAN), or the like.

Further, the configuration of the motion information processing apparatus 100 according to the first embodiment described above is merely an example, and it is possible to integrate together or separate any of the functional circuitry, as appropriate. For example, it is possible to integrate the motion information storage circuitry 1301 and the position information storage circuitry 1302 together. It is also possible to separate the obtaining circuitry 1401 into a plurality of obtaining circuitry each of which is configured to obtain a different one of the plurality of pieces of motion information.

Further, the functions of the obtaining circuitry 1401, the position calculating circuitry 1402, and the display controlling circuitry 1403 described in the first to the third embodiments may be realized by software. For example, the functions of the obtaining circuitry 1401, the position calculating circuitry 1402, and the display controlling circuitry 1403 may be realized by causing a computer to execute a medical information processing computer program (hereinafter, "medical information processing program") that defines the procedure of the processes described as being performed by the obtaining circuitry 1401, the position calculating circuitry 1402, and the display controlling circuitry 1403 in the embodiments above. For example, the medical information processing program is stored in a hard disk, a semiconductor memory device, or the like so as to be read and executed by a processor such as a CPU, a Micro Processing Unit (MPU), or the like. Further, the medical information processing program may be distributed as being recorded on a computer-readable recording medium such as a Compact Disk Read-Only Memory (CD-ROM), a Magnetic Optical (MO) disk, a Digital Versatile Disk (DVD), or the like.

As explained above, the motion information processing apparatus 100 according to the first to the fourth embodiments provides the subject undergoing the rehabilitation with the effective aids, by obtaining the detailed information about the motions of the subject undergoing the rehabilitation. Next, as fifth to eighth embodiments, a motion information processing apparatus that provides a subject undergoing rehabilitation with effective aids, by obtaining precise information of the subject undergoing the rehabilitation will be explained.

Fifth Embodiment

Figure 20:
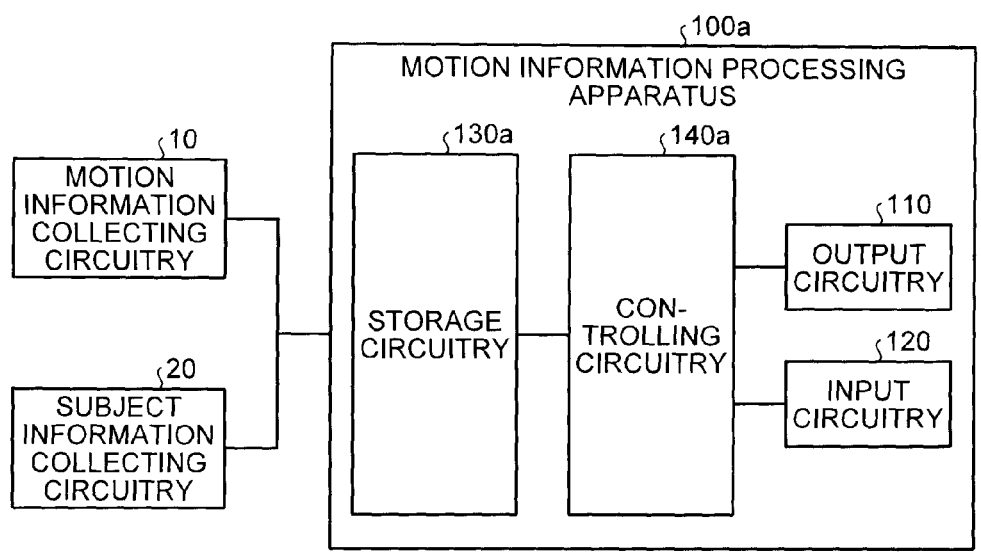
FIG. 20 is a diagram of an exemplary configuration of a motion information processing apparatus according to a fifth embodiment.

FIG. 20 is a diagram of an exemplary configuration of a motion information processing apparatus 100a according to the fifth embodiment. Similar to the motion information processing apparatus 100 according to the first to the fourth embodiments, the motion information processing apparatus 100a according to the fifth embodiment is, for example, an apparatus configured to aid rehabilitation performed in a medical institution, a home, an office, or the like.

As illustrated in FIG. 20, in the fifth embodiment, the motion information processing apparatus 100a is connected to a motion information collecting circuitry 10 and a subject information collecting circuitry 20. Although FIG. 20 illustrates the single motion information collecting circuitry 10 and the single subject information collecting circuitry 20, possible embodiments are not limited to this example. For instance, two or more motion information collecting circuitry 10 and two or more subject information collecting circuitry 20 may be connected to the motion information processing apparatus 100a. In this situation, the motion information collecting circuitry 10 illustrated in FIG. 20 is the same as the motion information collecting circuitry 10 illustrated in FIG. 2. In other words, the motion information collecting circuitry 10 illustrated in FIG. 20 is configured to acquire the information about the motions of a subject and to send the acquired various types of information to the motion information processing apparatus 100a, so as to store the acquired information into a storage circuitry 130a (explained later; e.g., a motion information storage circuitry 1303). Because these processes are the same as those described above, detailed explanation thereof will be omitted.

Figure 21:
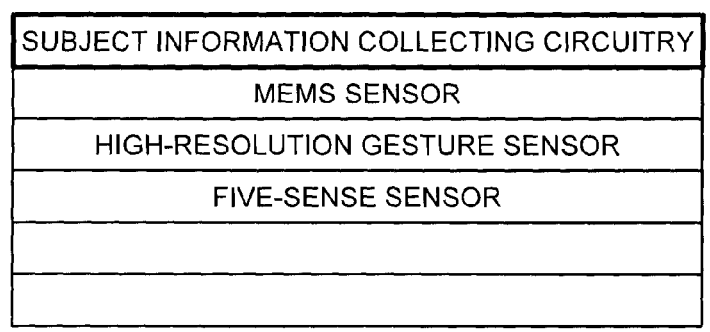
FIG. 21 is a table of examples of sensors that are applicable as a subject information collecting circuitry according to the fifth embodiment.

The subject information collecting circuitry 20 is configured to acquire information about the subject undergoing rehabilitation. More specifically, the subject information collecting circuitry 20 acquires biological information of the subject, detailed motion information, and the like. For example, the subject information collecting circuitry 20 is configured by using any of various types of sensors. FIG. 21 is a table of examples of sensors that are applicable as the subject information collecting circuitry 20 according to the fifth embodiment. As illustrated in FIG. 21, examples of the subject information collecting circuitry 20 include a Micro Electro Mechanical Systems (MEMS) sensor, a high-resolution gesture sensor, and a five-sense sensor.

In this situation, as for the MEMS sensor that can serve as the subject information collecting circuitry 20, examples thereof include sensors configured to acquire biological information such as a body temperature, a pulse rate, a blood pressure, perspirations, an electroencephalogram, an exercise amount (three-axis accelerations), and the like, as well as pressure sensors, vibration sensors, position sensors, velocity sensors, and angle sensors. As for the high-resolution gesture sensor, examples thereof include Leap (registered trademark) sensors and motion sensors that employ a marker and a tracking device. The Leap sensor is a precise motion capture system that has a resolution level of $1/100$ mm or smaller. As for the five-sense sensor, examples thereof include sensors configured to detect tactile sensation, sound, amounts of heat, and the like. The sensors listed above are merely examples. It is possible to arbitrarily select the sensor used as the subject information collecting circuitry 20, in accordance with the application use of the motion information processing apparatus 100a. For example, besides the sensors listed above, it is acceptable to use any other sensor, as long as the sensor is capable of acquiring biological information such as an electric conductivity level of a human body, a skin temperature, a blood oxygenation level, a foot pressure level, eye movements, a mastication strength level, or the like. Further, the sensor may be an infrared sensor, an ultrasound sensor, a shock sensor, a rotation sensor, an inclination sensor, or the like.

Further, the subject information collecting circuitry 20 outputs the acquired subject information (e.g., the various types of information of the subject acquired by any of the sensors) to the motion information processing apparatus 100a, so as to store the subject information into a subject information storage circuitry (explained later). In this situation, the timing with which the subject information is acquired by the subject information collecting circuitry 20 can arbitrarily be set by the operator. In other words, the subject information collecting circuitry 20 is configured to acquire the subject information once in every time period that is set in advance. In one example, the subject information collecting circuitry 20 is configured to acquire the subject information with the same timing (at the same times) as the frames in which the motion information is acquired by the motion information collecting circuitry 10.

Returning to the description of FIG. 1, the motion information processing apparatus 100a is configured to perform processes to aid rehabilitation, by using the motion information output from the motion information collecting circuitry 10 and the subject information acquired by the subject information collecting circuitry 20. More specifically, the motion information processing apparatus 100a generates and displays display information in which the motion information of the subject acquired by the motion information collecting circuitry 10 and the subject information acquired by the subject information collecting circuitry 20 are kept in synchronization with each other.

As noted above, as functional training for rehabilitation, various types of training such as walking training and joint range-of-motion training are conventionally performed. Subjects of rehabilitation vary, and it is considered important for some subjects that, for example, rehabilitation is performed at a speed and with a load that fit each subject. For this reason, the motion information processing apparatus 100a according to the fifth embodiment is configured to make it possible to obtain precise information of a subject undergoing rehabilitation, for the purpose of evaluating a detailed state of the subject undergoing the rehabilitation.

For example, the motion information processing apparatus 100a is an information processing apparatus configured with a computer, a workstation, or the like and includes, as illustrated in FIG. 20, the output circuitry 110, the input circuitry 120, the storage circuitry 130a, and a controlling circuitry 140a.

The output circuitry 110 is configured to output various types of information and the like related to the motions of the subject undergoing the rehabilitation. For example, the output circuitry 110 displays a Graphical User Interface (GUI) used by an operator who operates the motion information processing apparatus 100a to input various types of requests through the input circuitry 120 and displays image information indicating a walking state of the subject on the motion information processing apparatus 100a. For example, the output circuitry 110 is configured by using a monitor, a speaker, a headphone, a headphone portion of a headset, and/or the like. Further, the output circuitry 110 may be configured by using a display device of such a type that is attached to the body of the user, e.g., an eyeglass-type display device or a head-mount display device.

The input circuitry 120 is configured to receive an input of various types of information related to the motions of the subject undergoing the rehabilitation. For example, the input circuitry 120 receives an input of various types of requests (e.g., a selecting request to select an image to be displayed, and a measuring request to have a measuring process performed by using the GUI) from the operator of the motion information processing apparatus 100a and transfers the received various types of requests to the motion information processing apparatus 100a. For example, the input circuitry 120 may be configured by using a mouse, a keyboard, a touch command screen, a trackball, a microphone, a microphone portion of a headset, and/or the like.

The storage circuitry 130a is a storage device configured by using, for example, a semiconductor memory device such as a Random Access Memory (RAM) or a flash memory, a hard disk device, or an optical disk device. Further, the controlling circuitry 140a may be configured by using an integrated circuit such as an Application Specific Integrated Circuit (ASIC) or a Field Programmable Gate Array (FPGA) or may be realized by a Central Processing Unit (CPU) executing a predetermined computer program.

Figure 22:
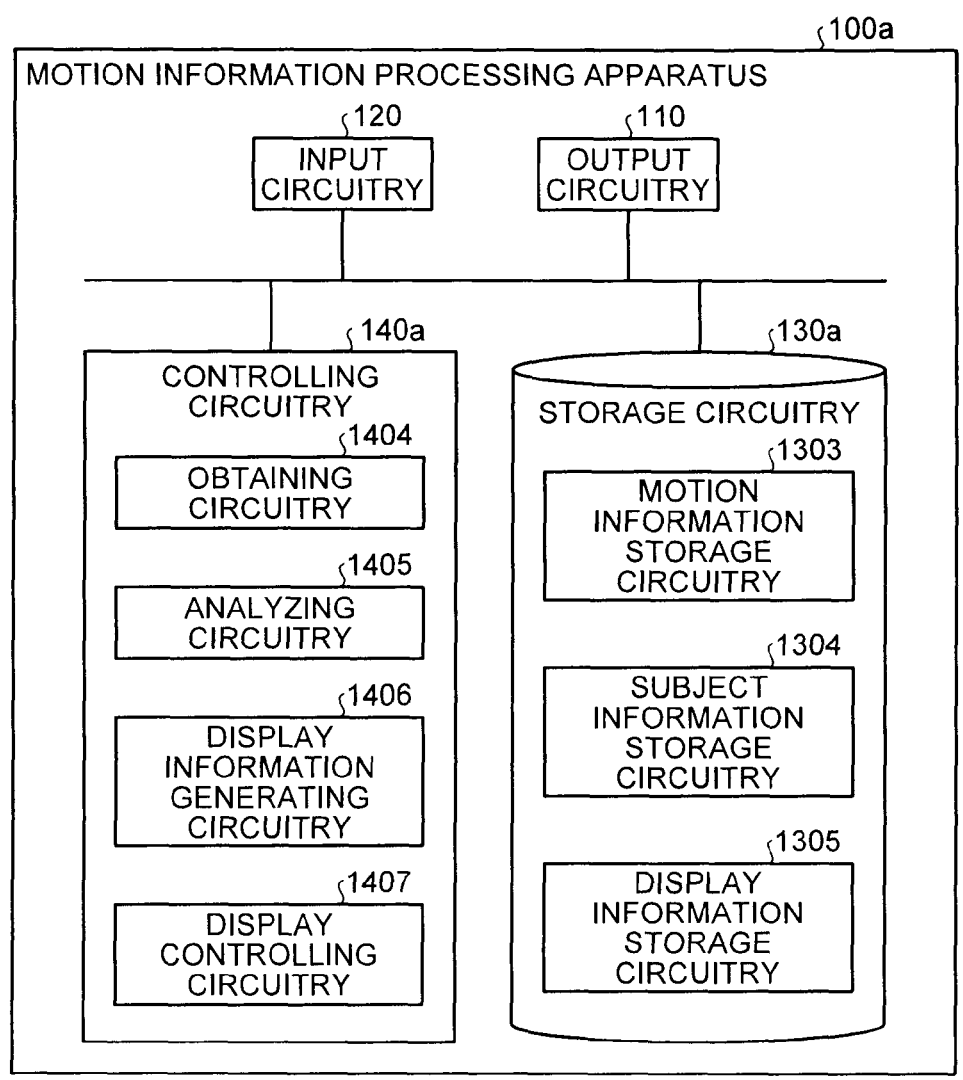
FIG. 22 is a diagram of an exemplary detailed configuration of the motion information processing apparatus according to the fifth embodiment.

A configuration of the motion information processing apparatus 100a according to the fifth embodiment has thus been explained. The motion information processing apparatus 100a according to the fifth embodiment configured as described above makes it possible to obtain the precise information of the subject undergoing the rehabilitation, by using the configuration explained below in detail. FIG. 22 is a diagram of an exemplary detailed configuration of the motion information processing apparatus 100a according to the fifth embodiment. First, details of the storage circuitry 130a included in the motion information processing apparatus 100a will be explained. As illustrated in FIG. 22, for example, in the motion information processing apparatus 100a, the storage circuitry 130a includes the motion information storage circuitry 1303, a subject information storage circuitry 1304, and a display information storage circuitry 1305.

The motion information storage circuitry 1303 is configured to store therein various types of information acquired by the motion information collecting circuitry 10. More specifically, the motion information storage circuitry 1303 stores therein pieces of motion information generated by the motion information generating circuitry 14 included in the motion information collecting circuitry 10. Even more specifically, the motion information storage circuitry 1303 stores therein the skeleton information for each of the frames generated by the motion information generating circuitry 14 included in the motion information collecting circuitry 10. In this situation, the motion information storage circuitry 1303 is also able to store therein the color image information, the distance image information, and the sound recognition result output by the motion information generating circuitry 14 in such a manner that these pieces of information are further kept in correspondence with one another for each of the frames.

FIG. 23 is a table of an example of the motion information stored in the motion information storage circuitry 1303 according to the fifth embodiment. As illustrated in FIG. 23, the motion information storage circuitry 1303 stores therein motion information in which the name of each subject is kept in correspondence with a name number, dates of rehabilitation, and pieces of motion information. In this situation, the "name number" is an identifier used for uniquely identifying the subject and is assigned to each subject name. Each of the "dates of rehabilitation" denotes a date on which the subject underwent walking training. Each of the pieces of "motion information" denotes the information acquired by the motion information collecting circuitry 10.

For example, as illustrated in FIG. 23, the motion information storage circuitry 1303 stores therein "Subject's Name: A; Name Number: 1; Date of Rehabilitation: 20120801_1; Motion Information: Color image information, Distance image information, Sound recognition result, Skeleton information, and . . . ". The piece of information indicates that, as motion information for the "first time" rehabilitation performed on "August 1st" in the "year 2012" by the person named "Subject's Name: A" of which the "Name Number" is "1", "color image information", "distance image information", an "sound recognition result", and "skeleton information" are stored.

In this situation, in the motion information illustrated in FIG. 23, the "color image information", the "distance image information", the "sound recognition result", and the "skeleton information" for each of all the frames taken while the rehabilitation is being performed are stored while being kept in correspondence with times in a time-series order.

Further, as illustrated in FIG. 23, the motion information storage circuitry 1303 stores therein "Subject's Name: A; Name Number: 1; Date of Rehabilitation: 20120801_2; Motion Information: Color image information, Distance image information, Sound recognition result, Skeleton information, and . . . ". In other words, the motion information storage circuitry 1303 similarly stores therein motion information of the "second time" walking training performed on "August 1st" in the "year 2012" by the person named "Subject's Name: A".

Further, as illustrated in FIG. 23, also for another person identified with "Subject's Name: B; Name Number: 2", the motion information storage circuitry 1303 stores therein motion information including "color image information", "distance image information", an "sound recognition result", and "skeleton information". The motion information storage circuitry 1303 thus stores therein the motion information of the rehabilitation acquired for each of the subjects, so as to be kept in correspondence with the subject. The motion information illustrated in FIG. 23 is merely an example. In other words, the motion information storage circuitry 1303 is able to store therein any information other than the "color image information", "distance image information", "sound recognition result" and "skeleton information" illustrated in FIG. 23, so as to be further kept in correspondence therewith. Further, for example, if the motion information collecting circuitry 10 does not include the sound recognizing circuitry 13, the motion information storage circuitry 1303 stores therein information that includes no sound recognition result.

Returning to the description of FIG. 22, the subject information storage circuitry 1304 is configured to store therein various types of information acquired by the subject information collecting circuitry 20. More specifically, the subject information storage circuitry 1304 stores therein pieces of subject information acquired by the subject information collecting circuitry 20 at different times while the subject is undergoing the rehabilitation. For example, the subject information storage circuitry 1304 stores therein the pieces of subject information acquired with the same timing (at the same times) as the frames acquired by the motion information collecting circuitry 10.

FIG. 24 is a table of an example of the subject information stored in the subject information storage circuitry 1304 according to the fifth embodiment. For example, as illustrated in FIG. 24, the subject information storage circuitry 1304 stores therein subject information in which the name of each subject is kept in correspondence with a name number, dates of rehabilitation, sensors, and pieces of subject information. In this situation, the "name number" is an identifier used for uniquely identifying the subject and is assigned to each subject name. Each of the "dates of rehabilitation" denotes a date on which the subject underwent the rehabilitation. The "sensors" denote the sensors that acquired the information of the subject undergoing the rehabilitation. Each of the pieces of "subject information" denotes the information acquired by the subject information collecting circuitry 20.

For example, as illustrated in FIG. 24, the subject information storage circuitry 1304 stores therein "Subject's Name: A; Name Number: 1; Date of Rehabilitation: 20120801_1; Sensor: Pressure sensor; Subject Information: Pressure information". Further, as illustrated in FIG. 24, the subject information storage circuitry 1304 stores therein "Subject's Name: A; Name Number: 1; Date of Rehabilitation: 20120801_1; Sensor: High-resolution gesture sensor; Subject Information: Motion information". These pieces of information indicate that, for the "first time" rehabilitation performed on "August 1st" in the "year 2012" by the person named "Subject's Name: A" of which the "Name Number" is "1", the subject information "Pressure information" acquired by the "Sensor: Pressure sensor" and the subject information "Motion information" acquired by the "Sensor: High-resolution gesture sensor" are stored.

In this situation, the pieces of subject information illustrated in FIG. 24 are stored at predetermined times (time intervals) while the rehabilitation is being performed, for each of the sensors. For example, the subject information storage circuitry 1304 stores therein, for each of the sensors, the pieces of subject information corresponding to each of all the frames taken of the subject by the motion information collecting circuitry 10, so as to be kept in correspondence with the times in a time-series order.

Further, as illustrated in FIG. 24, the subject information storage circuitry 1304 stores therein "Subject's Name: A; Name Number: 1; Date of Rehabilitation: 20120801_2; Sensor: Sphygmomanometer; Subject Information: Blood pressure" and "Subject's Name: A; Name Number: 1; Date of Rehabilitation: 20120801_2; Sensor: Heart rate meter; Subject Information: Heart rate". In other words, the subject information storage circuitry 1304 similarly stores therein the subject information for the "second time" rehabilitation performed on "August 1st" in the "year 2012" by the person named "Subject's Name: A".

As illustrated in FIG. 24, also for other people, the subject information storage circuitry 1304 similarly stores therein subject information for each of the sensors. In this manner, the subject information storage circuitry 1304 stores therein the subject information during the rehabilitation that was acquired for each of the subjects, so as to be kept in correspondence with the subject. The subject information illustrated in FIG. 24 is merely an example. In other words, the subject information storage circuitry 1304 is able to store therein subject information obtained by other various sensors, in addition to the subject information obtained by the sensors and for the subjects illustrated in FIG. 24. Further, although FIG. 24 illustrates the example in which the subject information is stored by using the two sensors as the subject information collecting circuitry 20 during the one-time rehabilitation, the subject information can be stored in the same manner even if the number of sensors is one or three or more.

Returning to the description of FIG. 22, the display information storage circuitry 1305 is configured to store therein display information generated by the controlling circuitry 140a (explained later). More specifically, the display information storage circuitry 1305 stores therein the display information in which the motion information and the subject information are kept in synchronization with each other by the controlling circuitry 140a (explained later). The display information will be explained later.

Next, details of the controlling circuitry 140a included in the motion information processing apparatus 100a will be explained. As illustrated in FIG. 22, in the motion information processing apparatus 100a, the controlling circuitry 140a includes, for example, an obtaining circuitry 1404, an analyzing circuitry 1405, a display information generating circuitry 1406, and a display controlling circuitry 1407.

The obtaining circuitry 1404 is configured to obtain the motion information of the subject undergoing the rehabilitation and the subject information indicating a state of the body of the subject. More specifically, the obtaining circuitry 1404 obtains the motion information stored in the motion information storage circuitry 1303 and the subject information stored in the subject information storage circuitry 1304. In one example, the obtaining circuitry 1404 obtains the color image information, the distance image information, the sound recognition result, and the skeleton information that are acquired by the motion information collecting circuitry 10 and are stored in the motion information storage circuitry 1303 for each of the frames, as well as the pressure information that is acquired by the subject information collecting circuitry 20 and is stored in the subject information storage circuitry 1304 while being kept in correspondence with the acquisition time.

Figure 25:
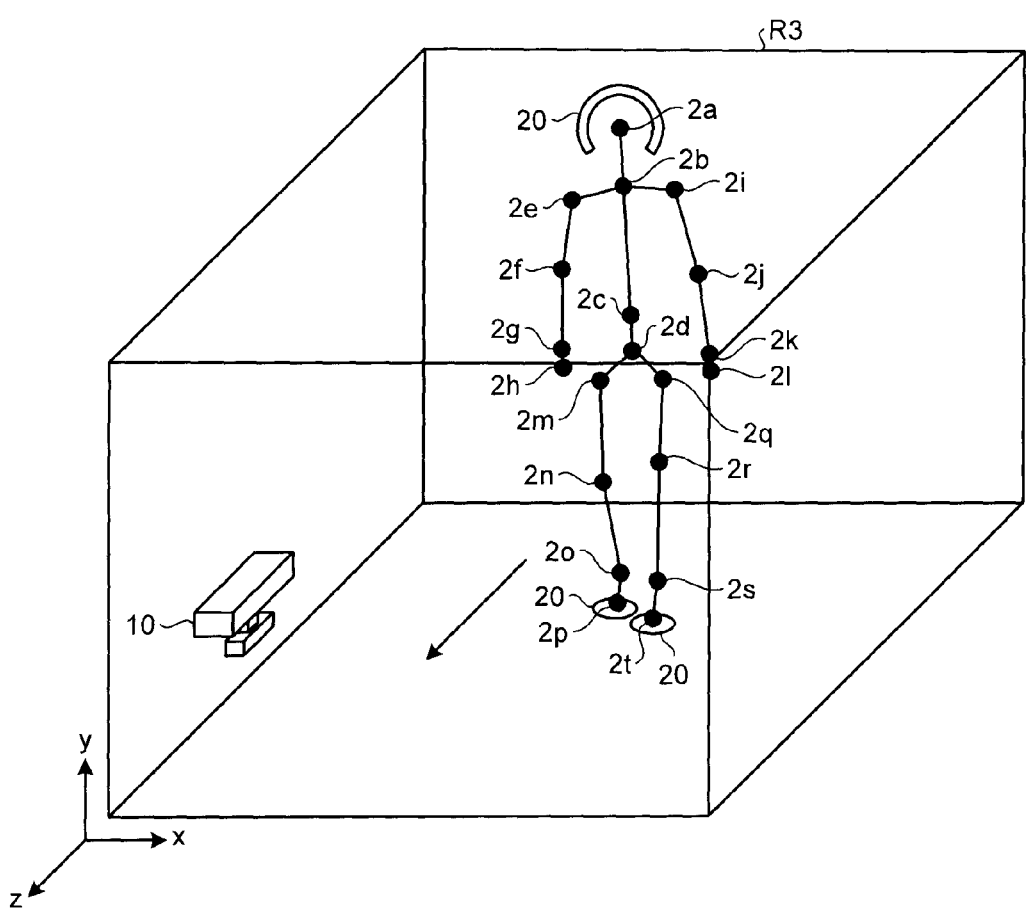
FIG. 25 is a schematic drawing for explaining an example of motion information obtained by an obtaining circuitry according to the fifth embodiment.

FIG. 25 is a schematic drawing for explaining an example of the motion information obtained by the obtaining circuitry 1404 according to the fifth embodiment. FIG. 25 illustrates the example in which the motion information collecting circuitry 10 is positioned as shown in the drawing, so as to obtain the motion information of a situation where the subject is performing walking training along the z-axis direction. Further, FIG. 25 illustrates the example in which the subject performs the walking training while wearing a pressure sensor (shown near the feet of the subject) and an electroencephalograph (shown on the head of the subject) that serve as the subject information collecting circuitry 20.

For example, as illustrated in FIG. 25, the obtaining circuitry 1404 obtains, from the motion information storage circuitry 1303, the motion information acquired by the motion information collecting circuitry 10 while the subject is performing the walking training along the z-axis direction. Further, for example, as illustrated in FIG. 25, the obtaining circuitry 1404 obtains, from the subject information storage circuitry 1304, electroencephalogram information acquired by the electroencephalograph serving as the subject information collecting circuitry 20 and the pressure information acquired by the pressure sensor serving as the subject information collecting circuitry 20, while the subject is performing the walking training.

In other words, as illustrated in FIG. 25, the obtaining circuitry 1404 obtains the color image information, the distance image information, the skeleton information, and the like of the subject in a region R3, which is an image taking region of the motion information collecting circuitry 10, and also obtains the electroencephalogram information and the pressure information of the feet of the subject during the walking training. In this situation, for example, the obtaining circuitry 1404 obtains the pieces of motion information by using the subject's name, the name number, the date of rehabilitation, or the like, as a key. In other words, the obtaining circuitry 1404 obtains pieces of color image information, pieces of distance image information, and pieces of skeleton information that correspond to all the frames related to a series of walking motions made during the walking training of the subject and are acquired by the motion information collecting circuitry 10 and also obtains the subject information acquired by the subject information collecting circuitry 20 with predetermined timing. Alternatively, the obtaining circuitry 1404 may obtain, in a real-time manner, the pieces of motion information stored in the motion information storage circuitry 1303 and the subject information stored in the subject information storage circuitry 1304 in a real-time manner.

Returning to the description of FIG. 22, the analyzing circuitry 1405 is configured to perform various analyzing processes by using the motion information of the subject performing the rehabilitation motions acquired by the obtaining circuitry 1404. More specifically, the analyzing circuitry 1405 analyzes the state of the motions on the basis of chronological changes in the position of a predetermined site of the subject in the motion information obtained by the obtaining circuitry 1404. For example, on the basis of chronological changes in the position of a tarsus, an ankle, a knee, or the like of the subject performing the walking training, the analyzing circuitry 1405 analyzes a walking state such as the positions of the landing points of the feet of the subject, the number of steps, a step length, a step width, a cadence value (the number of steps in a unit time period), or a stride distance (the distance between where one foot landed and where the same foot landed again).

Further, for example, the analyzing circuitry 1405 analyzes an inclination of the subject undergoing the rehabilitation, the velocity, the acceleration, the moving distance, and/or the like of a predetermined site of the subject, by using the motion information such as the color image information, the distance image information, the sound recognition result, the skeleton information, or the like obtained by the obtaining circuitry 1404.

The display information generating circuitry 1406 is configured to generate the display information in which the motion information and the subject information obtained by the obtaining circuitry 1404 are kept in synchronization with each other. More specifically, the display information generating circuitry 1406 generates, as the display information, the subject information of the subject corresponding to when the subject is performing a predetermined motion related to the rehabilitation. Even more specifically, while the subject is performing different types of rehabilitation such as walking training, joint range-of-motion training, and the like, the display information generating circuitry 1406 generates, on the basis of an analysis result obtained by the analyzing circuitry 1405, the display information indicating the subject information corresponding to when the subject is performing a predetermine motion during each of the different types of rehabilitation.

Figure 26:
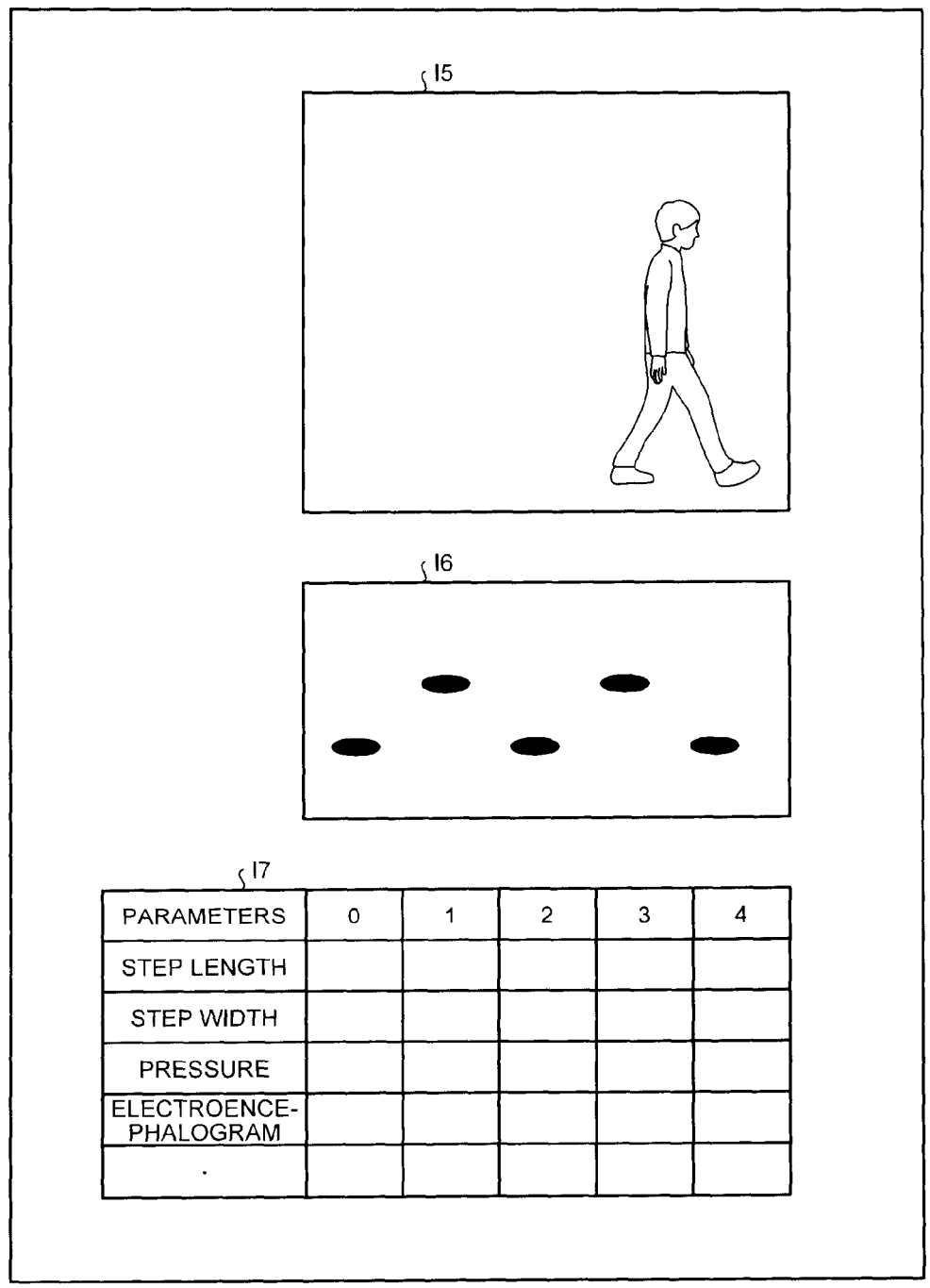
FIG. 26 is a drawing of an example of display information generated by a display information generating circuitry according to the fifth embodiment.

FIG. 26 is a drawing of an example of the display information generated by the display information generating circuitry 1406 according to the fifth embodiment. FIG. 26 illustrates an example in which the subject performs walking training as rehabilitation. Further, in FIG. 26, I5 illustrates color image information of motion information acquired by the motion information collecting circuitry 10. Also, in FIG. 26, I6 illustrates a drawing of feet landing points generated on the basis of an analysis result obtained by the analyzing circuitry 1405. In addition, in FIG. 26, I7 illustrates a table including the analysis result obtained by the analyzing circuitry 1405 and subject information acquired by the subject information collecting circuitry 20.

For example, as illustrated in FIG. 26, the display information generating circuitry 1406 generates the display information in which the color image information indicating a walking manner of the subject, a drawing indicating the positions of the feet landing points of the subject rendered in the color image information, and a table showing the analysis result and the subject information are displayed on a single screen. In other words, the display information generating circuitry 1406 arranges the color image information included in the motion information obtained by the obtaining circuitry 1404 to be positioned as illustrated in FIG. 26. Further, the display information generating circuitry 1406 arranges the drawing indicating the positions of the feet landing points of the subject resulting from the analysis performed by the analyzing circuitry 1405 to be positioned underneath the arranged color image information.

Next, the drawing I6 illustrated in FIG. 26 will be explained. As noted above, the drawing I6 in FIG. 26 is a drawing indicating the positions of the feet landing points of the subject resulting from the analysis performed by the analyzing circuitry 1405. On the basis of the coordinates of the feet resulting from the analysis by the analyzing circuitry 1405, the display information generating circuitry 1406 generates the drawing I6. An example of the analysis performed on the positions of the feet landing points can be explained as follows: For example, the analyzing circuitry 1405 judges whether each of the feet is in contact with the ground, on the basis of the value of the height (the y coordinate) of the tarsus, the ankle, or the knee in the skeleton information (the coordinate information) of the motion information obtained by the obtaining circuitry 1404. After that, the analyzing circuitry 1405 outputs, to the display information generating circuitry 1406, the coordinates of the position in which the foot was determined to be in contact with the ground, as the position of a landing point of the foot.

The method for analyzing the positions of the feet landing points described above is merely an example. In other words, the analyzing circuitry 1405 is able to analyze the positions of the feet landing points of the subject by using any of other various methods that uses the skeleton information of the subject included in the motion information. For example, the analyzing circuitry 1405 is also able to determine that one of the feet is in contact with the ground when a joint (e.g., a tarsus, an ankle, or a knee) of the subject is not making a spatial move in the advancing direction of the walk.

Further, the information about the positions of the feet landing points may be acquired, not only from the skeleton information included in the motion information of the subject acquired by the motion information collecting circuitry 10, but also by the subject information collecting circuitry 20. For example, the subject performing the walking training may wear a MEMS position information sensor as the subject information collecting circuitry 20, so that the obtaining circuitry 1404 obtains high-precision information about the positions of the feet landing points of the subject from the subject information collecting circuitry 20. By using the obtained information, it is possible to realize the display of the drawing I6 illustrated in FIG. 26 by using the information with the higher precision.

After that, the display information generating circuitry 1406 generates the drawing I6 illustrated in FIG. 26, by receiving the information about the positions of the feet landing points output by the analyzing circuitry 1405 or the high-precision information about the positions of the feet landing points of the subject obtained by the obtaining circuitry 1404. For example, as illustrated in I6 in FIG. 26, the display information generating circuitry 1406 generates the drawing with a view of the feet landing points from the above. In that situation, the display information generating circuitry 1406 extracts the x coordinates and the z coordinates of the positions of the feet landing points received from the analyzing circuitry 1405 and generates the drawing in which footprints are arranged in the extracted positions on an x-z plane. After that, as illustrated in FIG. 26, the display information generating circuitry 1406 arranges the drawing I6 to be positioned underneath the color image information, after adjusting the size of the x-z plane in such a manner that the positions of the footprints arranged on the x-z plane fit the positions in which the feet of the subject landed that are rendered in the color image information I5.

Further, as illustrated in FIG. 26, the display information generating circuitry 1406 arranges the analysis information and the subject information at each of the positions of the feet landing points to be displayed in the table. For example, as illustrated in FIG. 26, the display information generating circuitry 1406 arranges the table I7 in which parameters are kept in correspondence with each of the steps to be positioned underneath the drawing I6. In this situation, the display information generating circuitry 1406 arranges the table I7 to be positioned underneath the drawing I6, after adjusting the size of the table I7 in such a manner that the positions of the steps in the table I7 fit the positions of the footprints indicated in the drawing I6.

For example, as illustrated in FIG. 26, the display information generating circuitry 1406 generates the display information indicating a "step length", a "step width", "pressure", and "electroencephalogram" for each of the steps. In this situation, for example, as for the "step lengths" and the "step widths", the display information generating circuitry 1406 receives analysis results obtained by the analyzing circuitry 1405. Further, as for the "pressure" and the "electroencephalogram", the display information generating circuitry 1406 obtains values indicating the times at which the feet were determined to be in contact with the ground from the subject information obtained by the obtaining circuitry 1404 and displays the obtained values in the table. In other words, the display information generating circuitry 1406 generates the display information in which the table showing the parameters (the analysis results and the subject information) at the points in time when the feet of the subject performing the walking training landed is arranged so as to fit the positions of the footprints.

In the description above, the example is explained in which the information about the "step lengths" and the "step widths" is analyzed from the motion information; however, this configuration is merely an example. It is also acceptable to analyze the information about the "step lengths" and the "step widths" from the subject information. For example, the subject performing the walking training may wear a MEMS position information sensor as the subject information collecting circuitry 20, so that the obtaining circuitry 1404 obtains high-precision information about the positions of the feet landing points of the subject from the subject information collecting circuitry 20. After that, the analyzing circuitry 1405 analyzes the "step lengths" and the "step widths" of the subject by using the high-precision information about the positions of the feet landing points obtained by the obtaining circuitry 1404. By using the information, it is possible to realize the display of the table I7 illustrated in FIG. 26 by using the information with the higher precision.

The configuration described above is merely an example. In other words, the rehabilitation performed by the subject is not limited to walking training. The subject may perform any of other various types of rehabilitation. Further, in the description above, the points in time when the feet landed are explained as the predetermined motion during the walking training; however possible embodiments are not limited to this example. For instance, subject information may be displayed with regard to points in time when the feet of the subject are raised to the highest positions during walking training. Further, in the description above, the "step lengths", the "step widths", the "pressure", and the "electroencephalogram" are used as the examples of the parameters; however, possible embodiments are not limited to these examples. For instance, it is also acceptable to use blood pressure values and/or heart rates.

Returning to the description of FIG. 22, the display controlling circuitry 1407 is configured to cause the output circuitry 110 to display the display information generated by the display information generating circuitry 1406. For example, the display controlling circuitry 1407 causes the output circuitry 110 to display the display information illustrated in FIG. 26.

As explained above, the motion information processing apparatus 100a according to the fifth embodiment displays the display information in which the subject information is kept in synchronization with the motion information acquired by the motion information collecting circuitry 10. With this arrangement, the motion information processing apparatus 100a is able to provide the subject information indicating the state of the body of the subject during the predetermined motions and thus makes it possible to obtain the precise information of the subject undergoing the rehabilitation.

Figure 27:
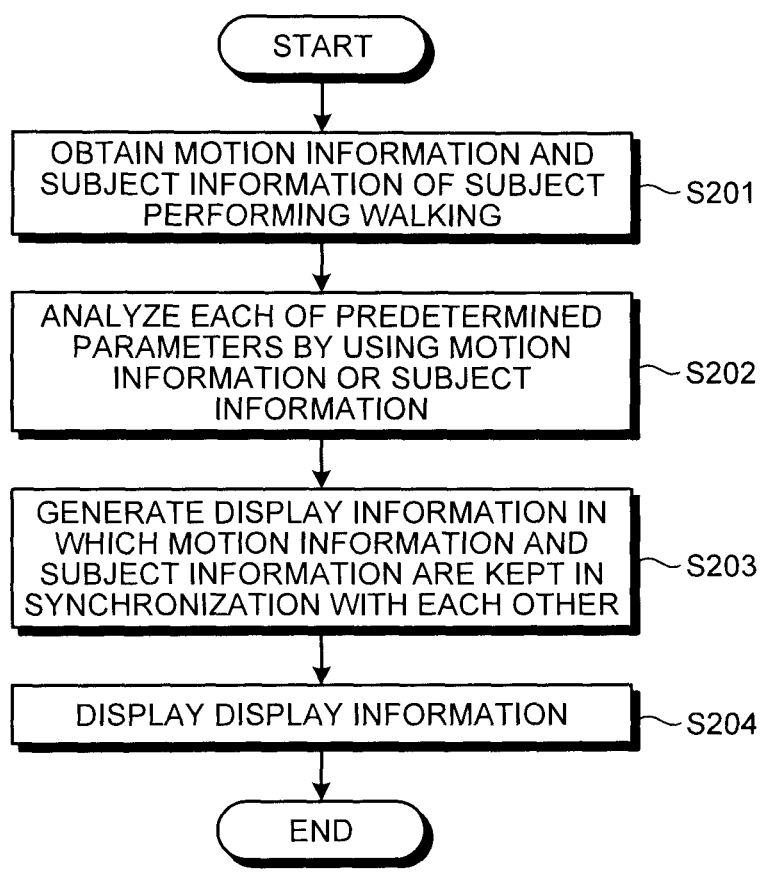
FIG. 27 is a flowchart of a procedure in a process performed by a motion information processing apparatus according to the fifth embodiment.

Next, a process performed by the motion information processing apparatus 100a according to the fifth embodiment will be explained, with reference to FIG. 27. FIG. 27 is a flowchart of a procedure in the process performed by the motion information processing apparatus 100a according to the fifth embodiment. FIG. 27 illustrates an example in which walking training is performed as rehabilitation.

As illustrated in FIG. 27, in the motion information processing apparatus 100a according to the fifth embodiment, when walking training is started, the obtaining circuitry 1404 obtains motion information and subject information of the subject performing the walking training (step S201). In other words, the obtaining circuitry 1404 obtains the motion information from the motion information storage circuitry 1303 and further obtains the subject information at the times corresponding to the obtained motion information, from the subject information storage circuitry 1304.

After that, the analyzing circuitry 1405 analyzes each of the predetermined parameters by using the obtained motion information or the obtained subject information (step S202). For example, for parameters that require high-precision information, the analyzing circuitry 1405 performs the analysis by using the subject information. For other parameters, the analyzing circuitry 1405 performs the analysis by using the motion information.

After that, the display information generating circuitry 1406 generates display information in which the motion information, the subject information, and the analysis results are kept in association (synchronization) with one another (step S203). For example, the display controlling circuitry 1407 generates the display information in which the image information included in the motion information, the information about the predetermined parameters included in the subject information, and the analysis results resulting from the analysis by the analyzing circuitry 1405 are kept in association with one another. After that, the display controlling circuitry 1407 exercises control so as to cause the output circuitry 110 to display the generated display information (step S204).

As explained above, according to the fifth embodiment, the obtaining circuitry 1404 obtains the motion information of the subject undergoing the rehabilitation and the subject information indicating the state of the body of the subject. After that, the display information generating circuitry 1406 generates the display information in which the motion information and the subject information obtained by the obtaining circuitry 1404 are kept in synchronization with each other. After that, the display controlling circuitry 1407 exercises control so as to cause the output circuitry 110 to display the display information generated by the display information generating circuitry 1406. Consequently, the motion information processing apparatus 100a according to the fifth embodiment is able to display the subject information that is kept in synchronization with the motions of the subject undergoing the rehabilitation and thus makes it possible to obtain the precise information of the subject undergoing the rehabilitation.

Further, according to the fifth embodiment, the display information generating circuitry 1406 generates, as the display information, the subject information of the subject corresponding to when the subject is performing the predetermined motion related to the rehabilitation. Consequently, the motion information processing apparatus 100a according to the fifth embodiment makes it possible to provide the subject information corresponding to the motions unique to the rehabilitation.

Further, according to the fifth embodiment, the obtaining circuitry 1404 obtains the biological information as the subject information. Further, the display information generating circuitry 1406 generates, as the display information, the biological information of the subject corresponding to when the subject is performing the predetermined motion related to the rehabilitation. Consequently, the motion information processing apparatus 100a according to the fifth embodiment is able to provide vital information of the subject during the rehabilitation and thus makes it possible to obtain the precise information of the subject.

Further, according to the fifth embodiment, the analyzing circuitry 1405 analyzes the motions of the subject, by using the motion information obtained by the obtaining circuitry 1404. The display information generating circuitry 1406 generates, as the display information, the subject information at the points in time when the subject is performing the predetermined motion included in the motions of the subject analyzed by the analyzing circuitry 1405. Consequently, the motion information processing apparatus 100a according to the fifth embodiment is able to determine the timing of the predetermined motion on the basis of the motion information and thus makes it possible to provide the more precise information.

Sixth Embodiment

In the fifth embodiment described above, the example is explained in which the various types of analyses are performed by using the skeleton information acquired by the motion information collecting circuitry 10 or the subject information acquired by the subject information collecting circuitry 20. In a sixth embodiment, an example will be explained in which the motion information is corrected by using the information acquired as the subject information, so that various types of analyses are performed by using the corrected motion information. In the sixth embodiment, processes performed by the analyzing circuitry 1405 are different. The sixth embodiment will be explained below while a focus is placed on the different processes.

The analyzing circuitry 1405 according to the sixth embodiment is configured to correct the motion information by using high-precision motion information and to perform various types of analyses by using the corrected motion information. More specifically, when the subject information obtained by the obtaining circuitry 1404 is high-precision motion information, the analyzing circuitry 1405 corrects the motion information acquired by the motion information collecting circuitry 10 by using the high-precision motion information and performs an analysis on the motions of the subject by using the corrected motion information.

Figure 28A:
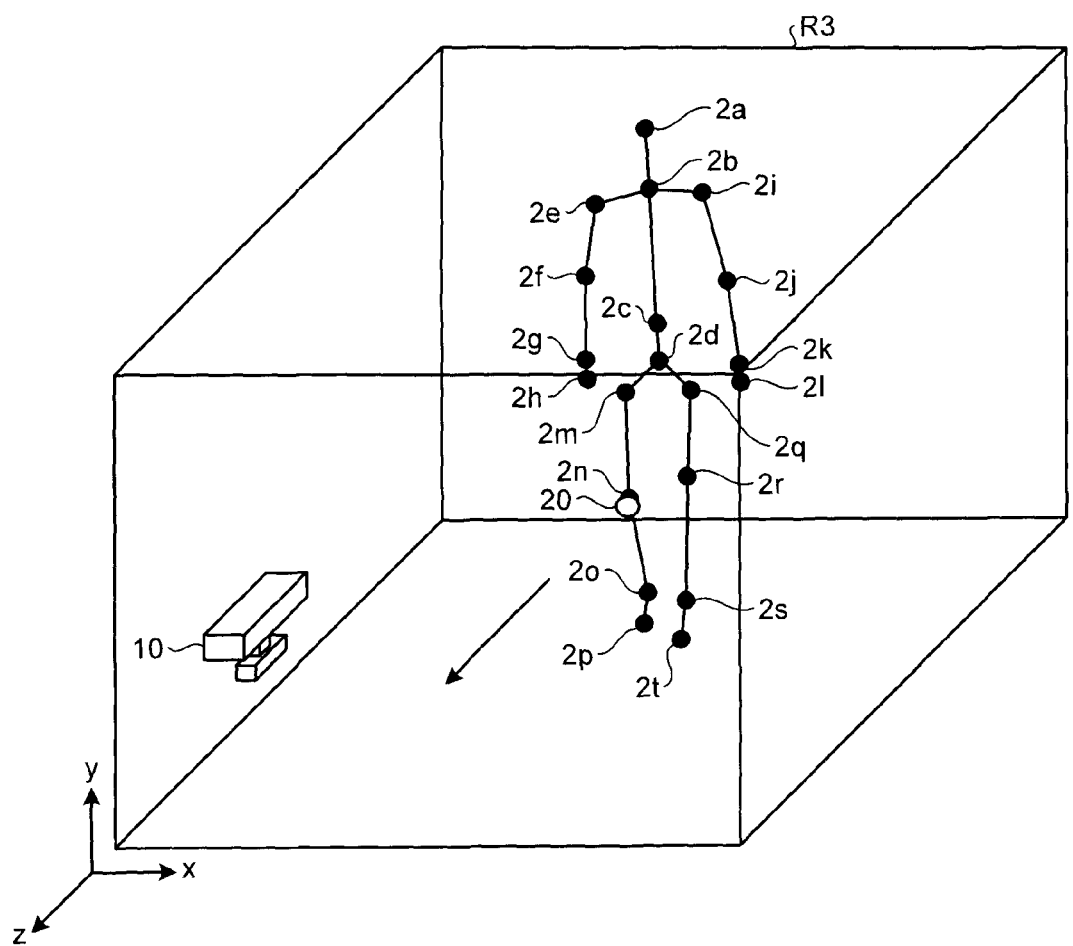
FIG. 28A is a drawing for explaining an example of a motion information acquiring process according to a sixth embodiment.
Figure 28B:
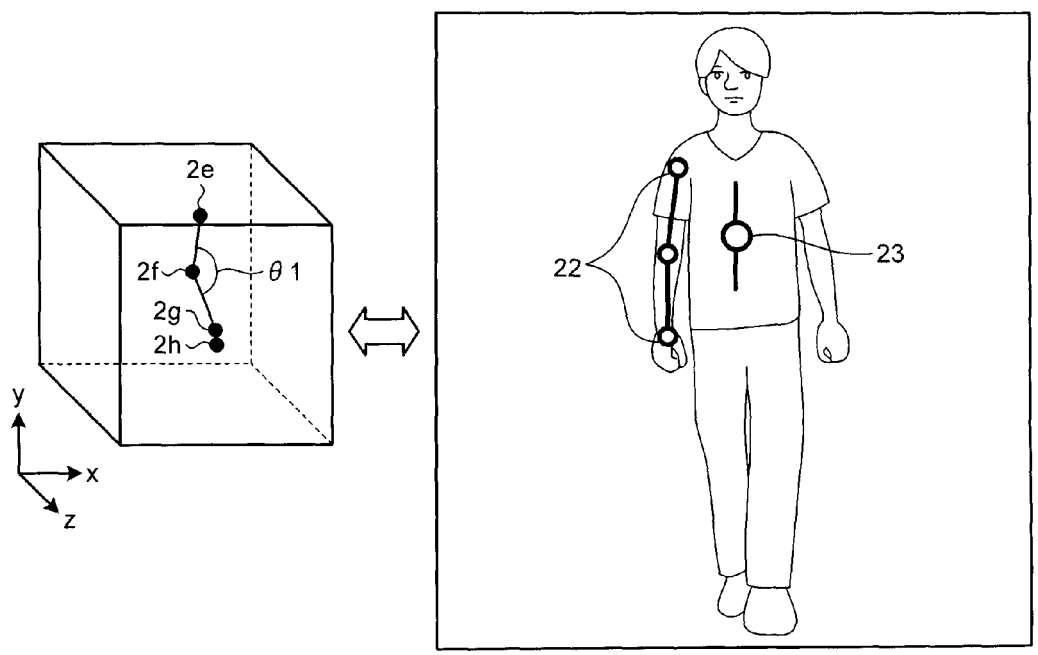
FIG. 28B is a drawing for explaining another example of the motion information acquiring process according to the sixth embodiment.

In that situation, for example, a marker and a tracking device are used as the subject information collecting circuitry 20, so as to acquire the high-precision motion information. FIGS. 28A and 28B are drawings for explaining examples of the motion information acquiring process according to the sixth embodiment. FIG. 28A illustrates an example in which the position of a predetermined site of the subject is corrected. FIG. 28B illustrates an example in which the angle and the velocity of a predetermined site of the subject are corrected. For example, to acquire the high-precision motion information with respect to positions, the subject wears the marker serving as the subject information collecting circuitry 20 on the right knee, as illustrated in FIG. 28A, so that the motion information of the knee of the subject is obtained as a result of the tracking device (not shown) tracking the position of the marker.

The analyzing circuitry 1405 corrects the coordinates of the other joints of the subject on the basis of the coordinates of the joint "2n" corresponding to the right knee acquired by the motion information collecting circuitry 10 and the coordinates of the right knee acquired by the subject information collecting circuitry 20. In other words, the analyzing circuitry 1405 calculates the coordinates of the positions at the coordinates of the other joints in the coordinate space acquired by the subject information collecting circuitry 20, on the basis of the coordinates of the joint "2n" corresponding to the right knee acquired by the motion information collecting circuitry 10 and the coordinates of the right knee acquired by the subject information collecting circuitry 20.

In one example, when the coordinates of the joint "2n" corresponding to the right knee acquired by the motion information collecting circuitry 10 are (10, 10, 10), whereas the coordinates of the right knee acquired by the subject information collecting circuitry 20 are (11.5, 10.8, 11.2), the analyzing circuitry 1405 corrects the coordinates of the joint "2n" from (10, 10, 10) to (11.5, 10.8, 11.2). After that, the analyzing circuitry 1405 corrects the coordinates of each of the other joints "2a" to "2t" acquired by the motion information collecting circuitry 10, by using a conversion coefficient calculated from the coordinates (10, 10, 10) of the joint "2n" corresponding to the right knee and the coordinates (11.5, 10.8, 11.2) of the right knee acquired by the subject information collecting circuitry 20. In other words, the analyzing circuitry 1405 corrects the coordinates by multiplying the coordinates of each of the other joints "2a" to "2t" by the conversion coefficient.

After that, the analyzing circuitry 1405 performs the various types of analyses by using the coordinates of the different sites of the subject (the coordinates in the coordinate space acquired by the subject information collecting circuitry 20) calculated from the correction described above. Consequently, the motion information processing apparatus 100a is able to perform the analyses by using the more accurate coordinates and thus makes it possible to provide the more precise display information by using the results of the analyses.

In the embodiment described above, the example is explained in which the high-precision motion information is acquired by using the marker and the tracking device serving as the subject information collecting circuitry 20; however, possible embodiments are not limited to this example. For instance, another arrangement is acceptable in which a plurality of motion information collecting circuitry 10 are provided, so that one of the plurality of motion information collecting circuitry 10 is realized with the marker and the tracking device.

Further, it is also possible to correct the angle and the velocity of a predetermined site of the subject in a similar manner. For example, to acquire the high-precision motion information with regard to angles or velocities, as illustrated in the drawing on the right side of FIG. 28B, the subject wears a joint angle sensor 22 or a velocity sensor 23 serving as the subject information collecting circuitry and performs walking training in a motion acquisition range of the motion information collecting circuitry 10. Accordingly, the analyzing circuitry 1405 analyzes the angle or the velocity by using the motion information. It is further possible to acquire high-precision angle information or velocity information from the subject information collecting circuitry (the joint angle sensor 22 or the velocity sensor 23).

In that situation, for example, when the operator wishes to obtain high-precision angle information, as illustrated on the left side of FIG. 28B, the analyzing circuitry 1405 first calculates, for each of the frames, an angle "θ1" formed by the bone connecting the joint "2e" corresponding to the right shoulder to the joint "2f" corresponding to the right elbow and the bone connecting the joint "2f" corresponding to the right elbow to the joint "2g" corresponding to the right wrist. In other words, the analyzing circuitry 1405 analyzes the angle of the right elbow of the subject during the walking motion. After that, the analyzing circuitry 1405 corrects the angle of the right elbow calculated for each of the frames, by using the angle of the right elbow obtained by the joint angle sensor 22 during the walking motion. In other words, the analyzing circuitry 1405 corrects the angle of the right elbow in any predetermined frame, so as to be equal to the angle of the right elbow obtained by the joint angle sensor 22 at the time corresponding to the frame.

In one example, when the angle "θ1" calculated by the analyzing circuitry 1405 is "170°", whereas the angle of the right elbow acquired by the joint angle sensor 22 is "176°", the analyzing circuitry 1405 corrects the angle "θ1" from "170°" to "176°". After that, the analyzing circuitry 1405 corrects the angles thereafter of the right elbow acquired by the motion information collecting circuitry 10 and the angle of each of the other joints, by using a conversion coefficient calculated from the angle "θ1" equal to "170°" and the angle "176°" of the right elbow acquired by the joint angle sensor 22. In other words, the analyzing circuitry 1405 corrects the angles by multiplying each of the angles of the right elbow thereafter and the angle of each of the other joints by the conversion coefficient.

As another example, when the operator wishes to obtain high-precision velocity information, as illustrated on the right side of FIG. 28B, the analyzing circuitry 1405 first calculates, for each of the frames, velocity information of a gravity point of the body of the subject to which the velocity sensor 23 is attached. After that, the analyzing circuitry 1405 corrects the velocity of the gravity point of the body calculated for each of the frames, by using the velocity information obtained by the velocity sensor 23 during the walking motion. In other words, the analyzing circuitry 1405 corrects the velocity of the gravity point of the body in any predetermined frame, so as to be equal to the velocity information obtained by the velocity sensor 23 at the time corresponding to the frame.

In one example, when the velocity of the gravity point of the body calculated by the analyzing circuitry 1405 is "0.5 m/sec", whereas the velocity acquired by the velocity sensor 23 is "0.58 m/sec", the analyzing circuitry 1405 corrects the velocity of the gravity point of the body from "0.5 m/sec" to "0.58 m/sec". After that, the analyzing circuitry 1405 corrects the velocities thereafter of the gravity point of the body acquired by the motion information collecting circuitry 10 and the velocity of each of the other sites, by using a conversion coefficient calculated from the velocity "0.5 m/sec" of the gravity point of the body and the velocity "0.58 m/sec" acquired by the velocity sensor 23. In other words, the analyzing circuitry 1405 corrects the velocities, by multiplying each of the velocities of the gravity point of the body thereafter and the velocity of each of the other sites by the conversion coefficient.

As explained above, according to the sixth embodiment, the obtaining circuitry 1404 obtains the high-resolution motion information that has a higher resolution than the motion information. Further, the analyzing circuitry 1405 analyzes the motions of the subject, after correcting the motion information by using the high-resolution motion information obtained by the obtaining circuitry 1404. Consequently, the motion information processing apparatus 100a according to the sixth embodiment makes it possible to analyze the motions of the subject by using the more accurate information.

Seventh Embodiment

The fifth and the sixth embodiments have thus been explained. The present disclosure, however, may be carried out in other various embodiments besides the fifth and the sixth embodiments described above.

In the fifth embodiment described above, the example is explained in which the display information is generated in which the color image information, the drawing indicating the positions of the feet landing points, and the table are arranged; however, possible embodiments are not limited to this example. It is also acceptable to generate display information in which one or more arbitrary drawings are arranged. For example, it is acceptable to generate display information in which the time of the color image information included in the motion information acquired by the motion information collecting circuitry 10 and the time of the color image information included in the motion information acquired by the subject information collecting circuitry 20 are kept in synchronization with each other.

Figure 29A:
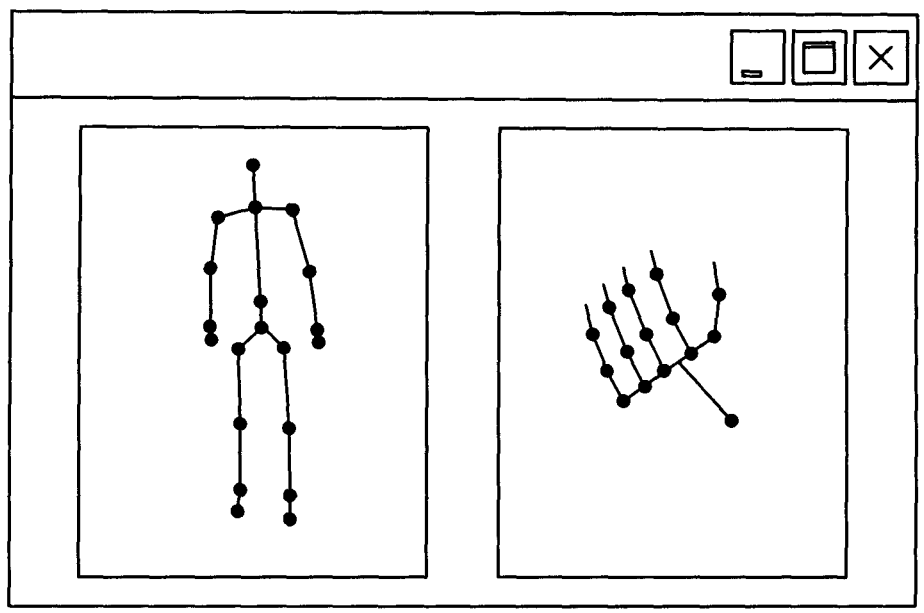
FIG. 29A is a drawing of an example of display information generated by a display information generating circuitry according to a seventh embodiment.
Figure 29B:
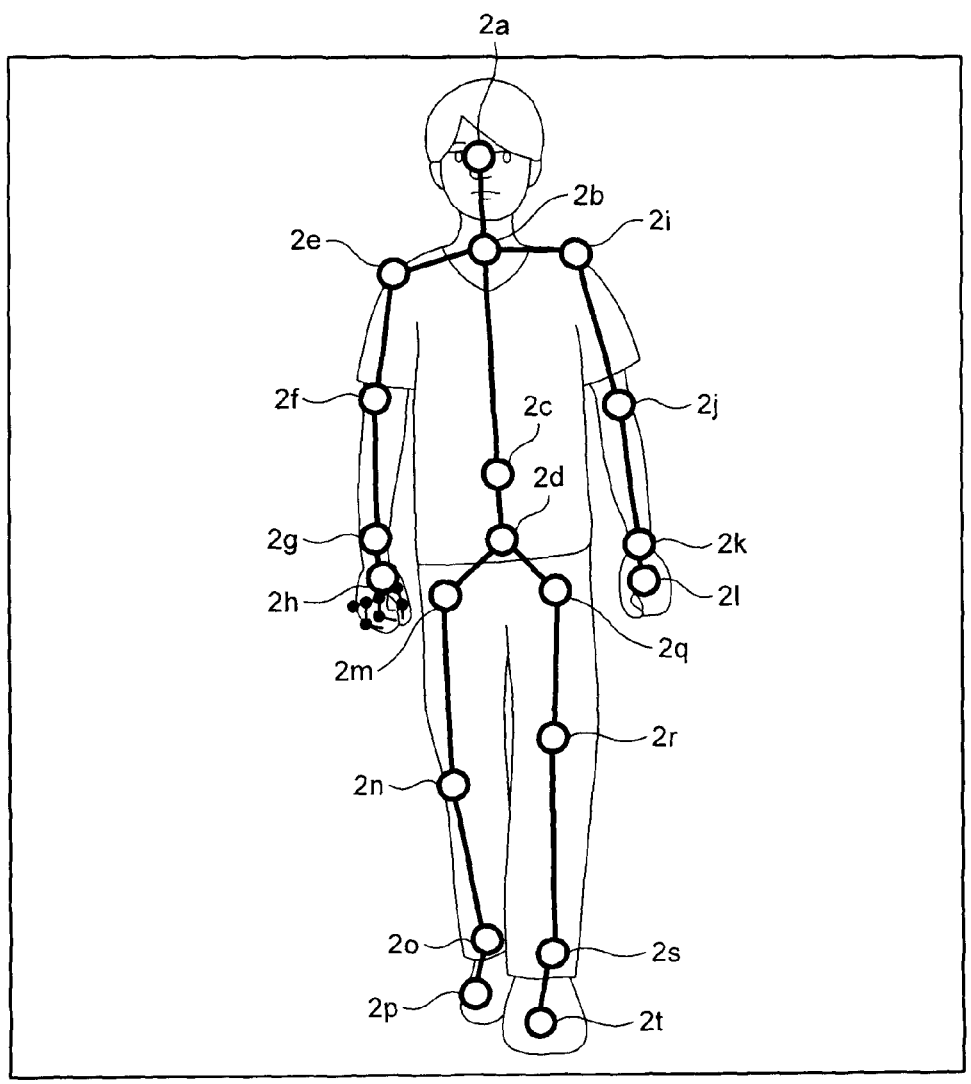
FIG. 29B is a drawing of another example of the display information generated by the display information generating circuitry according to the seventh embodiment.

FIGS. 29A and 29B are drawings of examples of the display information generated by the display information generating circuitry 1406 according to the seventh embodiment. For example, as illustrated in FIG. 29A, the display information generating circuitry 1406 generates display information in which color image information acquired by the motion information collecting circuitry 10 is arranged in the left region of the display window, while color image information acquired by the subject information collecting circuitry 20 is arranged in the right region of the display window.

In this situation, for example, a high-resolution motion capture system such as a Leap sensor is used as the subject information collecting circuitry 20. Accordingly, as illustrated in FIG. 29A, for example, the display information generating circuitry 1406 generates the display information in which detailed color image information of a hand of the subject is arranged in the right region of the display window. In this situation, the display information generating circuitry 1406 arranges the time of the color image information in the left region of the display window to be kept in synchronization with the time of the color image information in the right region.

Further, for example, as illustrated in FIG. 29B, the display information generating circuitry 1406 generates display information in which skeleton information acquired by the motion information collecting circuitry 10 and high-resolution skeleton information of the right hand of the subject acquired by the subject information collecting circuitry 20 are superimposed on mutually the same color image information.

Further, in the fifth and the sixth embodiments described above, the example is explained in which the display information is displayed by the output circuitry 110; however, possible embodiments are not limited to this example. For instance, another arrangement is acceptable in which guidance is provided or an alert is issued for the subject undergoing rehabilitation, on the basis of vital information in the subject information.

In that situation, for example, the storage circuitry 130a stores therein a predetermined threshold value for blood pressure or heart rates. Further, the controlling circuitry 140a monitors the blood pressure or the heart rate acquired by the subject information collecting circuitry 20 and, if the value has exceeded the predetermined threshold value, the controlling circuitry 140a exercises control so as to output an alert message such as "Please slow down the pace" or "Please reduce the load" for the subject undergoing the rehabilitation. For example, the controlling circuitry 140a outputs the message by using sound or a picture via the output circuitry 110.

As explained above, the motion information processing apparatus 100a according to the present disclosure is able to realize the various types of analyses and displays by using the motion information and the subject information. Consequently, for example, it is possible to use the motion information processing apparatus 100a for speech therapy or music therapy by employing a sound sensor as the subject information collecting circuitry 20 and to use the motion information processing apparatus 100a for a patient having a mental disorder by employing an electroencephalograph or a five-sense sensor as the subject information collecting circuitry 20.

Further, for example, when a small-sized sensor or a wearable sensor that can be used in daily life is available, by using such a sensor as the subject information collecting circuitry 20, the motion information processing apparatus 100a according to the present disclosure is able to handle daily life information and information during training in a collaborative manner. For example, the motion information processing apparatus 100a according to the present disclosure is able to check an improvement status in daily life and to evaluate effects after the training. Further, by using a sensor for displaying purposes as the subject information collecting circuitry 20, the motion information processing apparatus 100a according to the present disclosure is also able to provide a rehabilitation training status, a recovery status, and a maintenance/improvement status in an easy-to-understand and real-time manner. In other words, it is considered that, in most cases, subjects are too occupied to look at images during rehabilitation. For this reason, it is desirable to use an eyeglass-type display device (the sensor for displaying purposes) to provide a subject with a real-time display. Alternatively, instead of using images, the motion information processing apparatus 100a according to the present disclosure is also able to conduct information directly to the body of the subject by using a MEMS or the like. Further, to realize the real-time display by using an eyeglass-type display device, the motion information processing apparatus 100a according to the present disclosure is also able to provide navigation. It is possible to arbitrarily set how navigation is to be provided (in such a manner that the subject can easily copy the motion) and timing (how many seconds in prior, a motion to be performed should be displayed).

In the fifth and the sixth embodiments described above, the example is explained in which the motion information processing apparatus 100a obtains the motion information and the subject information of the subject undergoing the rehabilitation and displays the display information; however, possible embodiments are not limited to this example. For instance, the processes may be performed by a service providing apparatus connected to a network.

Figure 30:
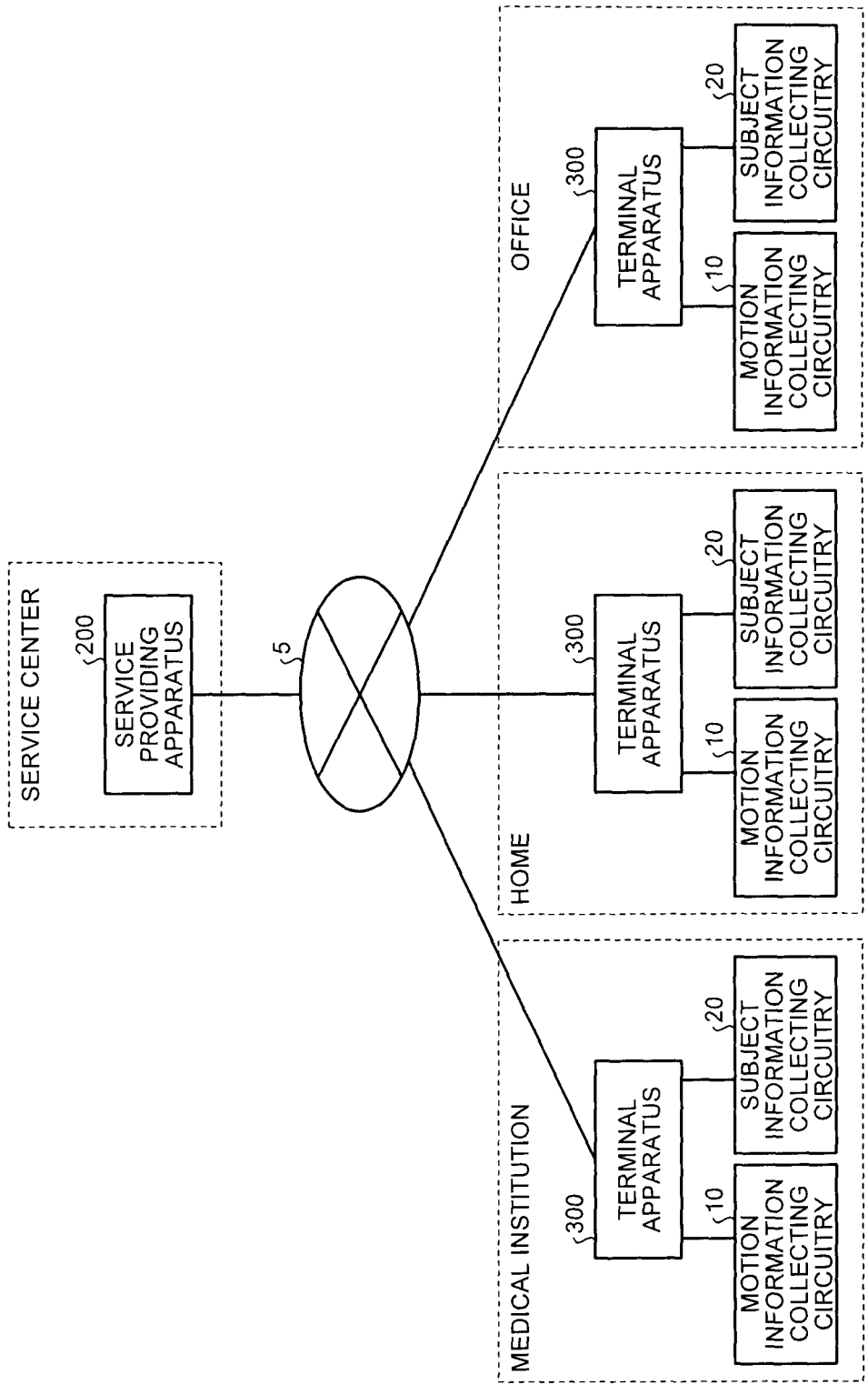
FIG. 30 is a diagram for explaining an example in which an aspect of the present disclosure is applied to a service providing apparatus according to the seventh embodiment.

FIG. 30 is a diagram for explaining an example in which an aspect of the present disclosure is applied to a service providing apparatus according to the seventh embodiment. As illustrated in FIG. 30, the service providing apparatus 200 is provided in a service center and is connected to, for example, the terminal apparatuses 300 that are provided in a medical institution, a home, and an office, via the network 5. To each of the terminal apparatuses 300 provided at the medical institution, the home, and the office, at least one motion information collecting circuitry 10 and at least one subject information collecting circuitry 20 are connected. Further, each of the terminal apparatuses 300 has a client function used for utilizing services provided by the service providing apparatus 200. It should be noted that, although FIG. 30 illustrates only one motion information collecting circuitry 10 and one subject information collecting circuitry 20 for each of the terminal apparatuses 300, any arbitrary number of circuitry may be connected thereto.

The service providing apparatus 200 is configured to provide, as the services, each of the terminal apparatuses 300 with the same processes as those of the motion information processing apparatus 100a. In other words, the service providing apparatus 200 includes functional circuitry that are equivalent to the obtaining circuitry 1404, the display information generating circuitry 1406, and the display controlling circuitry 1407. Further, the functional circuitry equivalent to the obtaining circuitry 1404 is configured to obtain the motion information of a subject undergoing rehabilitation and the subject information indicating a state of the body of the subject. Further, the functional circuitry equivalent to the display information generating circuitry 1406 is configured to generate the display information in which the subject information obtained by the functional circuitry equivalent to the obtaining circuitry 1404 is kept in synchronization. Further, the functional circuitry equivalent to the display controlling circuitry 1407 is configured to exercise control so as to cause a monitor of each of the terminal apparatuses 300 to display the display information generated by the functional circuitry equivalent to the display information generating circuitry 1406. The network 5 may be wired or wireless and may be configured with an arbitrary type of communication network such as the Internet, a Wide Area Network (WAN), or the like.

Further, the configuration of the motion information processing apparatus 100a according to the fifth embodiment described above is merely an example, and it is possible to integrate together or separate any of the functional circuitry, as appropriate. For example, it is possible to integrate the motion information storage circuitry 1303 and the subject information storage circuitry 1304 together. It is also possible to separate the obtaining circuitry 1404 into a motion information obtaining circuitry configured to obtain the motion information and a subject information obtaining circuitry configured to obtain the subject information.

Further, the functions of the obtaining circuitry 1404, the display information generating circuitry 1406, and the display controlling circuitry 1407 described in the fifth to the seventh embodiments may be realized by software. For example, the functions of the obtaining circuitry 1404, the display information generating circuitry 1406, and the display controlling circuitry 1407 may be realized by causing a computer to execute a medical information processing program that defines the procedure of the processes described as being performed by the obtaining circuitry 1404, the display information generating circuitry 1406, and the display controlling circuitry 1407 in the embodiments above. For example, the medical information processing program is stored in a hard disk, a semiconductor memory device, or the like so as to be read and executed by a processor such as a CPU, an MPU, or the like. Further, the medical information processing program may be distributed as being recorded on a computer-readable recording medium such as a Compact Disk Read-Only Memory (CD-ROM), a Magnetic Optical (MO) disk, a Digital Versatile Disk (DVD), or the like.

As explained above, the motion information processing apparatus 100a according to the fifth to the seventh embodiments provides the subject undergoing the rehabilitation with the effective aids, by obtaining the precise information of the subject undergoing the rehabilitation. Next, as eighth to tenth embodiments, a motion information processing apparatus configured to provide a subject undergoing rehabilitation with an effective aid, by providing the subject performing a motion to move from one place to another (hereinafter, "spatial move motion") with a stable aid will be explained.

Eighth Embodiment

Figure 31:
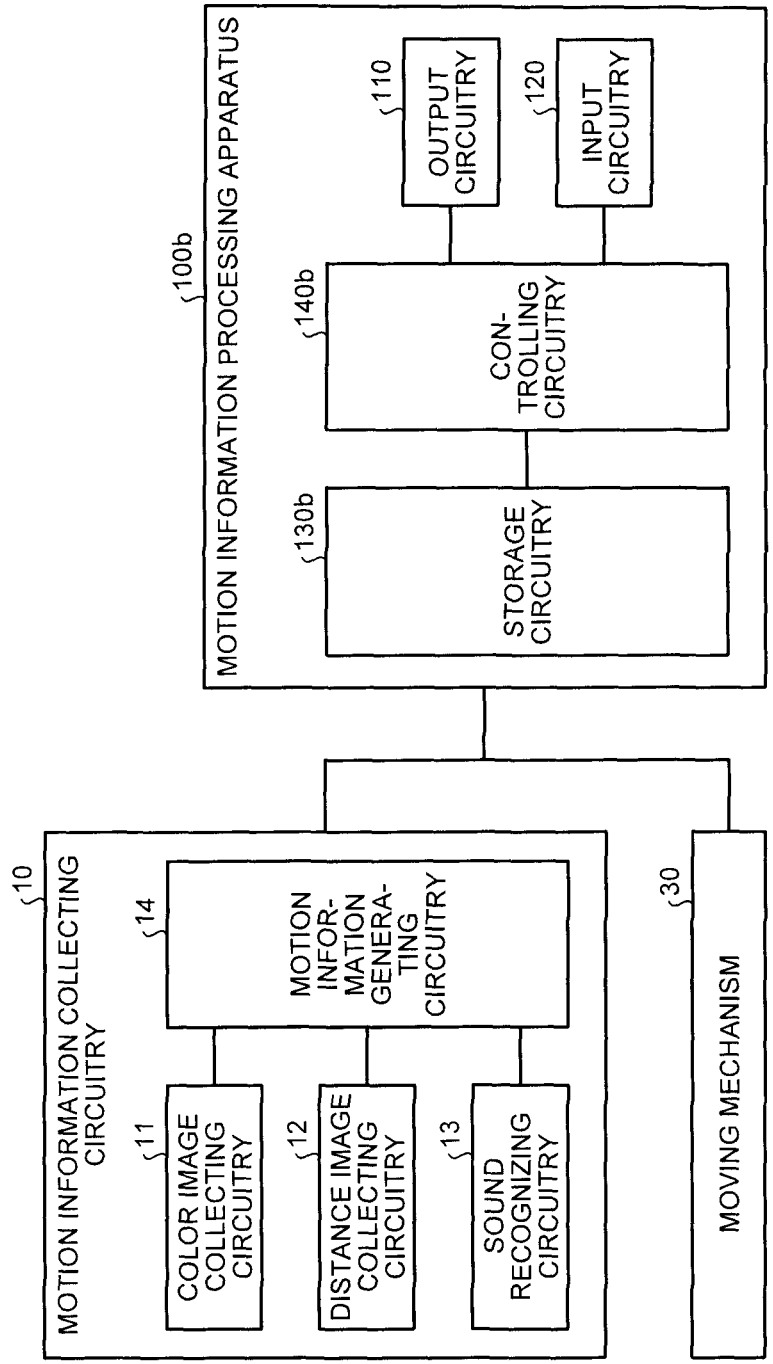
FIG. 31 is a diagram of an exemplary configuration of a motion information processing apparatus according to an eighth embodiment.

FIG. 31 is a diagram of an exemplary configuration of a motion information processing apparatus 100b according to the eighth embodiment. Similar to the motion information processing apparatus 100 according to the first to the fourth embodiments, the motion information processing apparatus 100b according to the eighth embodiment is, for example, an apparatus configured to aid rehabilitation performed in a medical institution, a home, an office, or the like.

As illustrated in FIG. 31, in the eighth embodiment, the motion information processing apparatus 100b is connected to the motion information collecting circuitry 10 and a moving mechanism 30. In this situation, the motion information collecting circuitry 10 illustrated in FIG. 31 is the same as the motion information collecting circuitry 10 illustrated in FIG. 2. In other words, the motion information collecting circuitry 10 illustrated in FIG. 31 is configured to acquire the information about motions of a subject and to send the acquired various types of information to the motion information processing apparatus 100*b*, so as to store the acquired information into a storage circuitry 130*b* (explained later; e.g., a motion information storage circuitry 1306). Because these processes are the same as those described above, detailed explanation thereof will be omitted.

The moving mechanism 30 is a mechanism configured to, even when a subject performs a spatial move motion, acquire the motion information of the subject in a stable manner. More specifically, the moving mechanism 30 causes the motion information collecting circuitry 10 that acquires the motion information to move, in such a manner that the motion information of the subject is acquired from a predetermined position with respect to the subject performing the spatial move motion. For example, the moving mechanism 30 according to the Eighth embodiment is a cart on which the motion information collecting circuitry 10 is placed. In that situation, the cart serving as the moving mechanism 30 includes a motor and travels so as to keep the distance from the subject constant. In other words, the moving mechanism 30 changes the position of the motion information collecting circuitry 10 in such a manner that the subject performing the spatial move motion is positioned inside a recognition range of the motion information collecting circuitry 10 at all times. Details of the moving mechanism 30 will be explained later.

The motion information processing apparatus 100*b* is configured to perform processes to aid rehabilitation, by using the motion information output from the motion information collecting circuitry 10. More specifically, the motion information processing apparatus 100*b* provides the subject undergoing the rehabilitation involving a spatial move motion with a stable aid.

As noted above, as functional training for rehabilitation, various types of training such as walking training and joint range-of-motion training are conventionally performed. Among the various types of training is training that involves a spatial move, such as walking training. In one example, during walking training, a subject may walk a distance of approximately 10 meters. However, because the recognition range in which the motion information collecting circuitry 10 recognizes the subject is not so large, when the subject has made a spatial move, the subject may be out of the recognition range of the motion information collecting circuitry 10. To cope with this situation, the motion information processing apparatus 100*b* according to the eighth embodiment is configured to make it possible to provide the subject performing the spatial move motion with a stable aid.

For example, the motion information processing apparatus 100*b* is an information processing apparatus configured with a computer, a workstation, or the like and includes, as illustrated in FIG. 31, the output circuitry 110, the input circuitry 120, the storage circuitry 130*b*, and a controlling circuitry 140*b*.

The output circuitry 110 is configured to output various types of information and the like related to the motions of the subject undergoing the rehabilitation. For example, the output circuitry 110 displays a Graphical User Interface (GUI) used by an operator who operates the motion information processing apparatus 100*b* to input various types of requests through the input circuitry 120 and displays information used by the motion information processing apparatus 100*b* to evaluate a walking state of the subject (information with which it is possible to evaluate effects of the rehabilitation). In one example, the output circuitry 110 displays, as the information used for evaluating the walking state, an image of the subject, coordinate information of different sites of the subject, information obtained by combining an image with coordinate information, or improvement degree information obtained by comparing information with information from the past. The configurations described above are merely examples. It is acceptable to output any type of information, as long as the information can be used for evaluating the walking state. For example, the output circuitry 110 is configured by using a monitor, a speaker, a headphone, a headphone portion of a headset, and/or the like. Further, the output circuitry 110 may be configured by using a display device of such a type that is attached to the body of the user, e.g., an eyeglass-type display device or a head-mount display device.

The input circuitry 120 is configured to receive an input of various types of information related to the motions of the subject undergoing the rehabilitation. For example, the input circuitry 120 receives an input of various types of requests (e.g., a selecting request to select an image to be displayed, and a measuring request to have a measuring process performed by using the GUI) from the operator of the motion information processing apparatus 100*b* and transfers the received various types of requests to the motion information processing apparatus 100*b*. For example, the input circuitry 120 may be configured by using a mouse, a keyboard, a touch command screen, a trackball, a microphone, a microphone portion of a headset, and/or the like. Further, the input circuitry 120 may be a sensor configured to obtain biological information such as a sphygmomanometer, a heart rate meter, a clinical thermometer, and/or the like.

The storage circuitry 130*b* is a storage device configured by using, for example, a semiconductor memory device such as a Random Access Memory (RAM) or a flash memory, a hard disk device, or an optical disk device. Further, the controlling circuitry 140*b* may be configured by using an integrated circuit such as an Application Specific Integrated Circuit (ASIC) or a Field Programmable Gate Array (FPGA) or may be realized by a Central Processing Unit (CPU) executing a predetermined computer program.

Figure 32:
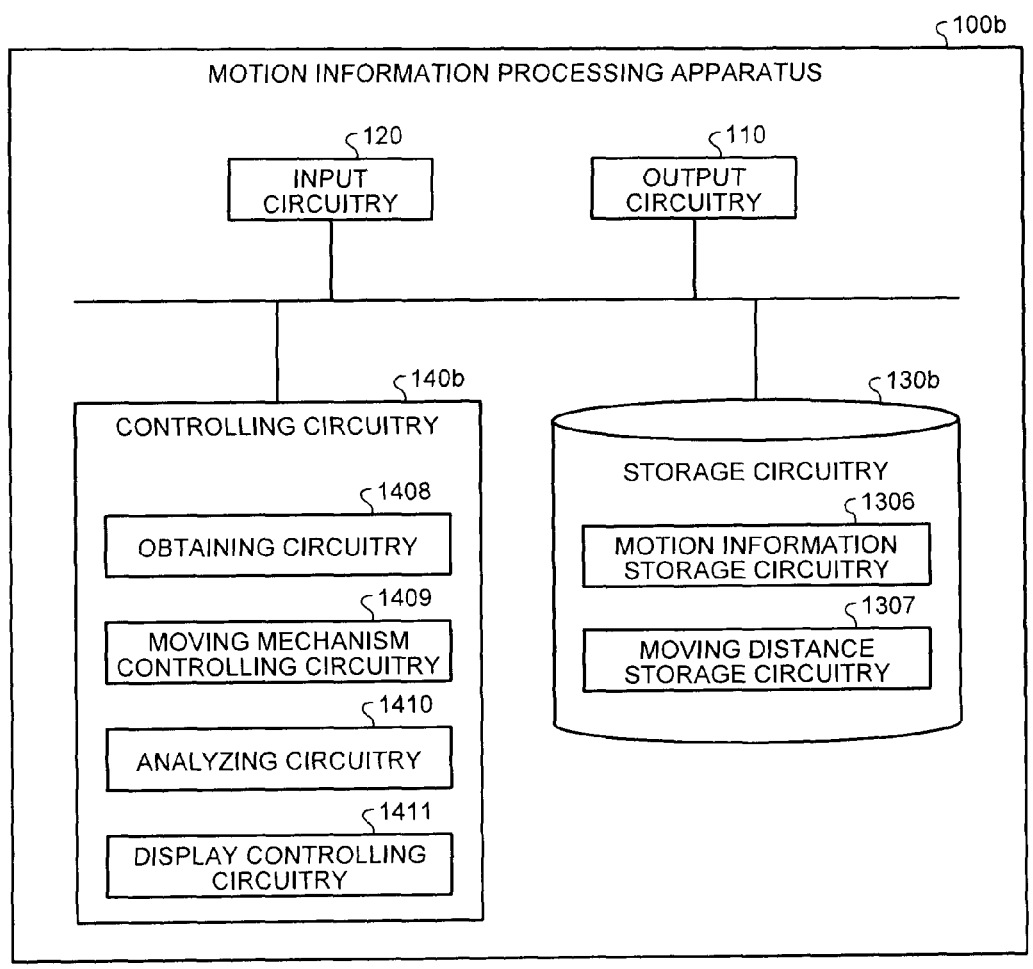
FIG. 32 is a diagram of an exemplary detailed configuration of the motion information processing apparatus according to the eighth embodiment.

A configuration of the motion information processing apparatus 100*b* according to the eighth embodiment has thus been explained. The motion information processing apparatus 100*b* according to the eighth embodiment configured as described above makes it possible to provide a subject performing a spatial move motion with a stable aid, by using the configuration explained below in detail. FIG. 32 is a diagram of an exemplary detailed configuration of the motion information processing apparatus 100*b* according to the eighth embodiment. First, details of the storage circuitry 130*b* included in the motion information processing apparatus 100*b* will be explained. As illustrated in FIG. 32, in the motion information processing apparatus 100*b*, for example, the storage circuitry 130*b* includes the motion information storage circuitry 1306 and a moving distance storage circuitry 1307.

The motion information storage circuitry 1306 is configured to store therein various types of information acquired by the motion information collecting circuitry 10. More specifically, the motion information storage circuitry 1306 stores therein the motion information generated by the motion information generating circuitry 14 included in the motion information collecting circuitry 10. Even more specifically, the motion information storage circuitry 1306 stores therein the skeleton information for each of the frames generated by the motion information generating circuitry 14 included in the motion information collecting circuitry 10. In this situation, the motion information storage circuitry 1306 is also able to store therein the color image information, the distance image information, and the sound recognition result output by the motion information generating circuitry 14 in such a manner that these pieces of information are further kept in correspondence with one another for each of the frames.

For example, the motion information storage circuitry 1306 according to the eighth embodiment stores therein the motion information illustrated in FIG. 23 described above. In other words, as illustrated in FIG. 23, the motion information storage circuitry 1306 stores therein the motion information in which the name of each subject is kept in correspondence with a name number, dates of rehabilitation, and pieces of motion information. In this situation, the "name number" is an identifier used for uniquely identifying the subject and is assigned to each subject name. Each of the "dates of rehabilitation" denotes a date on which the subject underwent the rehabilitation training. Each of the pieces of "motion information" denotes the information acquired by the motion information collecting circuitry 10.

For example, as illustrated in FIG. 23, the motion information storage circuitry 1306 stores therein "Subject's Name: A; Name Number: 1; Date of Rehabilitation: 20120801_1; Motion Information: Color image information, Distance image information, Sound recognition result, Skeleton information, and . . . ". The piece of information indicates that, for the "first time" rehabilitation performed on "August 1st" in the "year 2012" by the person named "Subject's Name: A" of which the "Name Number" is "1", the motion information including the "color image information, distance image information, sound recognition result, skeleton information, and so on" is stored.

In this situation, in the motion information illustrated in FIG. 23, the "color image information", the "distance image information", the "sound recognition result", the "skeleton information", and the like for each of all the frames taken while the rehabilitation motions are being performed are stored while being kept in correspondence with times in a time-series order. In other words, the motion information storage circuitry 1306 stores therein the "color image information", the "distance image information", the "sound recognition result", the "skeleton information", and the like acquired by the motion information collecting circuitry 10 during the rehabilitation motions corresponding to one time, while keeping these pieces of information in correspondence with the times at which these pieces of information are acquired. That is to say, the motion information storage circuitry 1306 stores therein the motion information acquired by the motion information collecting circuitry 10, so as to be kept in correspondence with the times of the frames.

Further, as illustrated in FIG. 23, the motion information storage circuitry 1306 stores therein "Subject's Name: A; Name Number: 1; Date of Rehabilitation: 20120801_2; Motion Information: Color image information, Distance image information, Sound recognition result, Skeleton information, and . . . ". In other words, the motion information storage circuitry 1306 similarly stores therein motion information of the "second time" rehabilitation performed on "August 1st" in the "year 2012" by the person named "Subject's Name: A".

As illustrated in FIG. 23, also for other people, the motion information storage circuitry 1306 similarly stores therein motion information including "color image information", "distance image information", an "sound recognition result", "skeleton information", and so on. The motion information storage circuitry 1306 thus stores therein the motion information of the rehabilitation acquired for each of the subjects, so as to be kept in correspondence with the subject. The motion information illustrated in FIG. 23 is merely an example. In other words, the motion information storage circuitry 1306 is able to store therein any information other than the "color image information", "distance image information", "sound recognition result" and "skeleton information" illustrated in FIG. 23, so as to be further kept in correspondence therewith. Further, for example, if the motion information collecting circuitry 10 does not include the sound recognizing circuitry 13, the motion information storage circuitry 1306 stores therein information that includes no sound recognition result.

The moving distance storage circuitry 1307 is configured to store therein an analysis result obtained by the controlling circuitry 140b (explained later). More specifically, the moving distance storage circuitry 1307 stores therein a moving distance of a sensor calculated by the controlling circuitry 140b (explained later) by using the motion information stored in the motion information storage circuitry 1306. The moving distance will be explained later.

Next, details of the controlling circuitry 140b included in the motion information processing apparatus 100b will be explained. As illustrated in FIG. 32, in the motion information processing apparatus 100b, the controlling circuitry 140b includes, for example, an obtaining circuitry 1408, a moving mechanism controlling circuitry 1409, an analyzing circuitry 1410, and a display controlling circuitry 1411.

The obtaining circuitry 1408 is configured to obtain the motion information of the subject acquired from a predetermined position with respect to the subject performing a spatial move motion (e.g., walking training). More specifically, the obtaining circuitry 1408 obtains, from the motion information storage circuitry 1306, the motion information of the subject acquired by the motion information collecting circuitry 10 of which the position is changed by the moving mechanism 30 in such a manner that the subject performing the spatial move motion is kept inside the recognition range of the motion information collecting circuitry 10 configured to acquire the motion information of the subject. In one example, the obtaining circuitry 1408 obtains the color image information, the distance image information, the sound recognition result, and the skeleton information that are acquired by the motion information collecting circuitry 10 of which the position is changed by the moving mechanism 30 in accordance with the spatial move motion of the subject and that are stored in the motion information storage circuitry 1306 for each of the frames.

Figure 33:
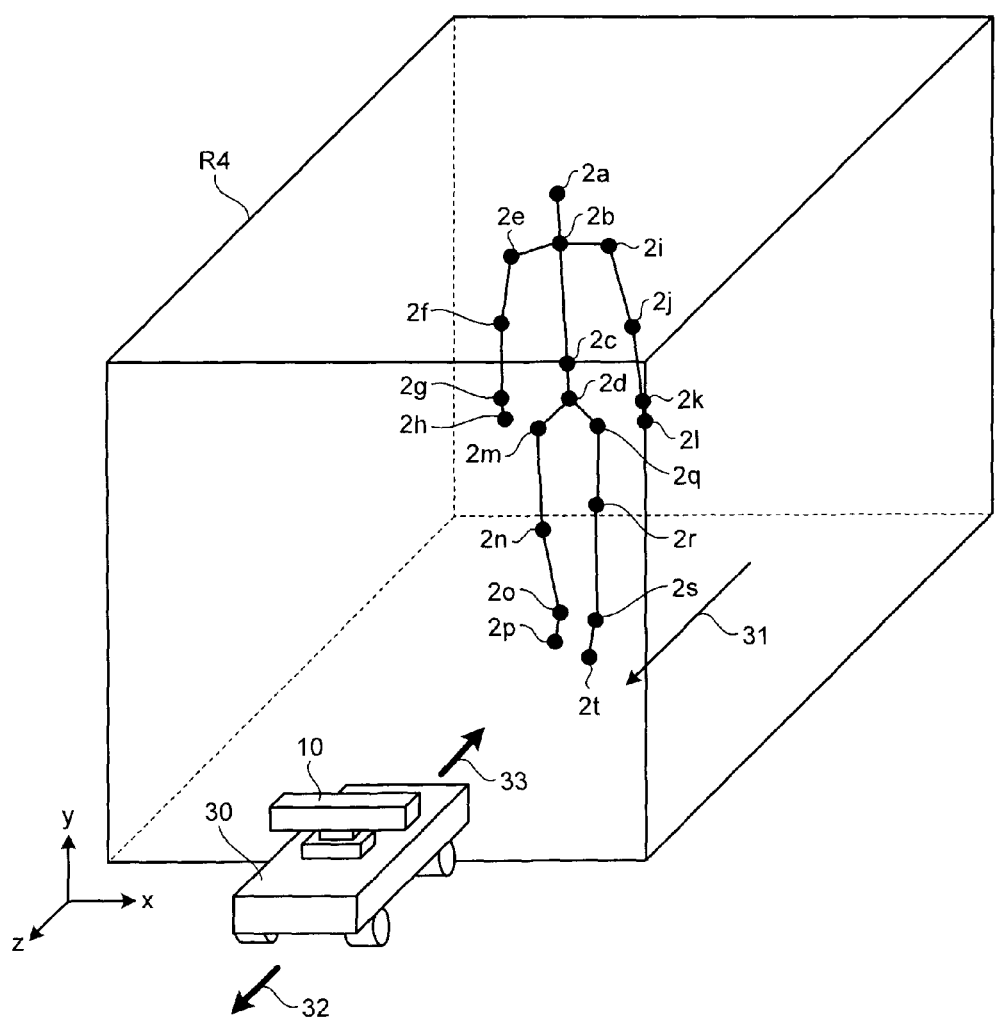
FIG. 33 is a schematic drawing for explaining an example of motion information obtained by an obtaining circuitry according to the eighth embodiment.

FIG. 33 is a schematic drawing for explaining an example of the motion information obtained by the obtaining circuitry 1408 according to the eighth embodiment. FIG. 33 illustrates an example in which the motion information collecting circuitry 10 is placed on the moving mechanism 30, so as to obtain the motion information of the subject performing walking training along the z-axis direction. In this situation, the moving mechanism 30 moves in the direction of an arrow 32 or an arrow 33 illustrated in FIG. 33, on the basis of the positional relationship with the subject, under control of the moving mechanism controlling circuitry 1409 (explained later). The control exercised by the moving mechanism controlling circuitry 1409 will be explained in detail later. For example, as illustrated in FIG. 33, the obtaining circuitry 1408 obtains, from the motion information storage circuitry 1306, the motion information of the subject acquired while the moving mechanism 30 is moved in such a manner that the subject is kept inside a region R4, which is the recognition range of the motion information collecting circuitry 10, while the subject is performing the walking training in the direction of an arrow 31 along the z-axis direction.

In other words, as illustrated in FIG. 33, the moving mechanism 30 is moved in such a manner that the subject performing the spatial move motion is kept inside the region R4, which is the recognition range of the motion information collecting circuitry 10, so that the obtaining circuitry 1408 obtains the color image information, the distance image information, the skeleton information, and the like of the subject in the region R4 having been moved. In this situation, for example, the obtaining circuitry 1408 obtains the pieces of motion information by using the subject's name, the name number, the date of rehabilitation, or the like, as a key. In other words, the obtaining circuitry 1408 obtains pieces of color image information, pieces of distance image information, and pieces of skeleton information that correspond to all the frames related to a series of walking motions made during the walking training of the subject and are acquired by the motion information collecting circuitry 10. Alternatively, the obtaining circuitry 1408 may obtain, in a real-time manner, the pieces of motion information stored in the motion information storage circuitry 1306 in a real-time manner.

Returning to the description of FIG. 32, the moving mechanism controlling circuitry 1409 is configured to move the moving mechanism 30 on the basis of the motion information of the subject obtained by the obtaining circuitry 1408. More specifically, the moving mechanism controlling circuitry 1409 moves the moving mechanism 30 in such a manner that the subject performing the spatial move motion is kept inside the recognition range of the motion information collecting circuitry 10 placed on the moving mechanism 30. For example, to further explain the configuration with reference to FIG. 33, while the subject performing the walking training is walking in the z-axis direction, the moving mechanism controlling circuitry 1409 calculates the distance between the motion information collecting circuitry 10 and the subject on the basis of the motion information of the subject and moves the moving mechanism 30 in the direction of the arrow 32 or the arrow 33 by driving the motor in accordance with the calculated distance.

In this situation, for example, the moving mechanism controlling circuitry 1409 controls the moving mechanism 30 so that the distance between the motion information collecting circuitry 10 and the subject is kept at "3 meters [m]". In one example, the moving mechanism controlling circuitry 1409 calculates the distance between the motion information collecting circuitry 10 and the subject from the z-axis coordinate value of a predetermined site (e.g., the joint 2*c* corresponding to the lumbar) of the subject, on the basis of the motion information of the subject obtained by the obtaining circuitry 1408. If the calculated distance is shorter than "3 m", the moving mechanism controlling circuitry 1409 moves the moving mechanism 30 in the direction of the arrow 32 illustrated in FIG. 33. On the contrary, if the calculated distance is longer than "3 m", the moving mechanism controlling circuitry 1409 moves the moving mechanism 30 in the direction of the arrow 33 illustrated in FIG. 33.

As explained above, because the moving mechanism controlling circuitry 1409 controls the moving mechanism 30 in such a manner that the distance between the motion information collecting circuitry 10 and the subject is kept constant, it is possible to exercise control so that the subject is kept inside the recognition range of the motion information collecting circuitry 10. In this situation, the threshold value for the distance between the motion information collecting circuitry 10 and the subject may arbitrarily be determined. In the example described above (the example illustrated in FIG. 33), the situation is explained in which the subject performs the walking training along the z-axis direction; however, possible embodiments are not limited to this example. The walking training may be performed in any arbitrary direction. For example, the subject may perform the walking training along the x-axis direction or a direction at a 45° angle from the z-axis direction. In that situation, the moving mechanism controlling circuitry 1409 exercises control so that the moving mechanism 30 moves along the x-axis or exercises control so that the moving mechanism 30 moves along the direction at the 45° angle from the z-axis direction. In other words, the moving mechanism 30 is configured so as to be able to move, not only in the directions of the arrow 32 and the arrow 33 illustrated in FIG. 33, but also in any direction at 360°. The moving mechanism controlling circuitry 1409 thus controls the moving mechanism 30 so as to keep the distance between the motion information collecting circuitry 10 and the subject constant.

Returning to the description of FIG. 32, the analyzing circuitry 1410 is configured to analyze the spatial move motion of the subject on the basis of the motion information obtained by the obtaining circuitry 1408. More specifically, the analyzing circuitry 1410 analyzes the spatial move motion of the subject, on the basis of the motion information that is of the subject performing the spatial move motion and is obtained by the obtaining circuitry 1408 and a change amount in the position of the motion information collecting circuitry 10. Even more specifically, the analyzing circuitry 1410 calculates a position relative to the motion information collecting circuitry 10 by using the chronological motion information obtained by the obtaining circuitry 1408 and analyzes the spatial move motion of the subject on the basis of the calculated relative position and the change amount in the position of the motion information collecting circuitry 10. In this situation, the change amount in the position of the motion information collecting circuitry 10 is calculated from an acceleration of the motion information collecting circuitry 10, from the rotation speed of a wheel or a motor provided for the moving mechanism 30, or by a wireless device provided for the moving mechanism 30.

Figure 34C:
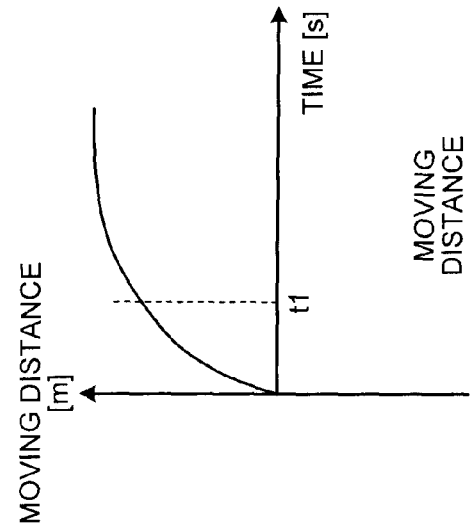
FIGS. 34A to 34C are drawings for explaining an example of a process of calculating a moving distance of a motion information collecting circuitry performed by an analyzing circuitry according to the eighth embodiment.
Figure 34B:
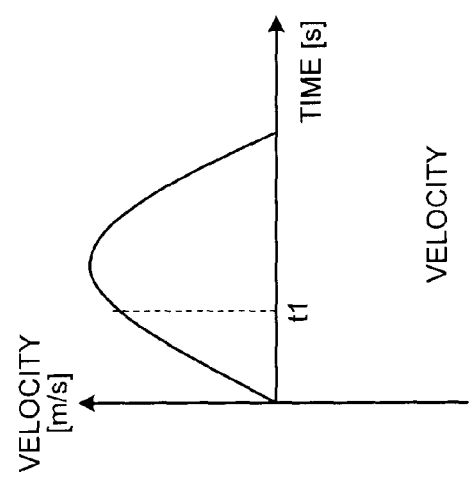
Figure 34A:
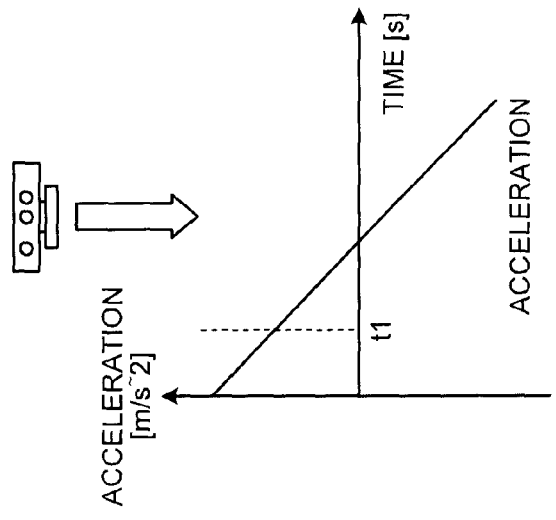

Next, an example of a process performed by the analyzing circuitry 1410 will be explained, with reference to FIGS. 34A to 35. FIGS. 34A to 34C are drawings for explaining an example of a process of calculating a moving distance of the motion information collecting circuitry 10 performed by the analyzing circuitry 1410 according to the eighth embodiment. FIGS. 34A to 34C illustrate an example in which the moving distance of the motion information collecting circuitry 10 is calculated by using an acceleration.

For example, as illustrated in FIG. 34A, the analyzing circuitry 1410 obtains an acceleration (m/s$^2$) at each of the times (e.g., t1 in FIGS. 34A to 34C) corresponding to the frames in which the motion information is acquired. After that, as illustrated in FIG. 34B, the analyzing circuitry 1410 calculates a velocity by integrating the obtained acceleration over time. Subsequently, as illustrated in FIG. 34C, the analyzing circuitry 1410 calculates a moving distance by multiplying the calculated velocity by the elapsed time. In this manner, the analyzing circuitry 1410 calculates the moving distance of the motion information collecting circuitry 10 from a point in time to another point in time (e.g., from t0 to t1). After that, the analyzing circuitry 1410 stores the calculated moving distance into the moving distance storage circuitry 1307 so as to be kept in correspondence with the time. In other words, the moving distance storage circuitry 1307 stores therein the information in which the moving distances of the motion information collecting circuitry 10 are kept in correspondence with the different points in time corresponding to the frames in which the motion information is acquired.

Besides the method described above for calculating the moving distances of the motion information collecting circuitry 10 that uses the acceleration, the analyzing circuitry 1410 is also able to calculate the moving distances of the motion information collecting circuitry 10 by using the rotation speed of a wheel of the moving mechanism 30, the rotation speed of the motor, or a Global Positioning System (GPS). Accordingly, even if it is not possible to obtain the acceleration of the motion information collecting circuitry 10, it is possible to calculate the moving distances of the motion information collecting circuitry 10.

Figure 35:
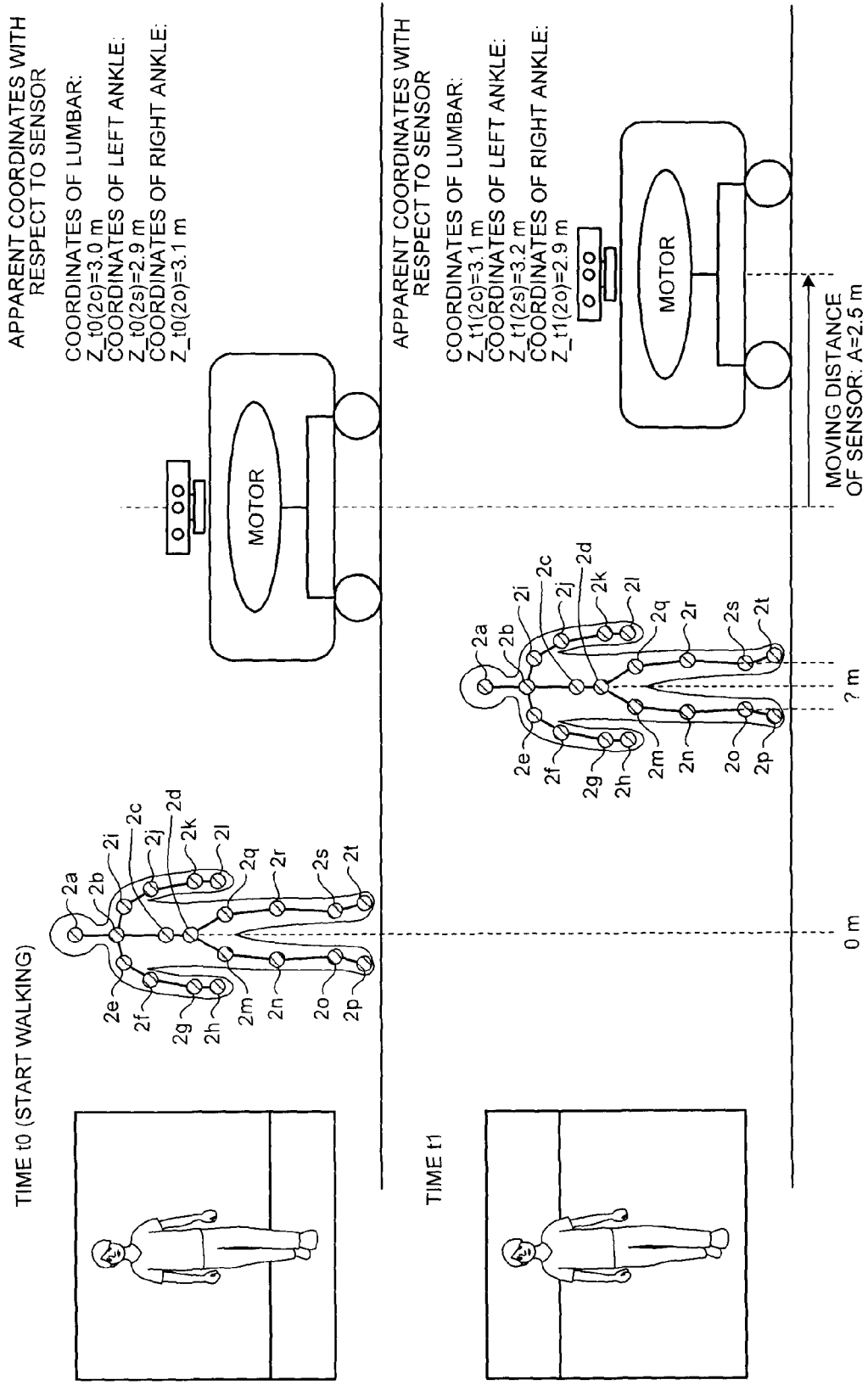
FIG. 35 is a drawing for explaining an example of a subject position analysis performed by the analyzing circuitry according to the eighth embodiment.

FIG. 35 is a drawing for explaining an example of a subject position analysis performed by the analyzing circuitry 1410 according to the eighth embodiment. In this situation, FIG. 35 illustrates an example in which the position of a subject performing walking training in the z-axis direction with respect to the floor at the time "t1" is calculated by using the position at the time "t0". In other words, according to the present disclosure, because the motion information collecting circuitry 10 moves in accordance with the spatial move of the subject, it is not possible to obtain position information of a fixed position within the coordinates of the fixed recognition range. For this reason, the analyzing circuitry 1410 calculates the position of the subject relative to the motion information collecting circuitry 10 and calculates the position of the subject with respect to the floor, on the basis of the calculated relative position and the moving distances of the motion information collecting circuitry 10 stored in the moving distance storage circuitry 1307.

In this situation, the drawing in the upper half of FIG. 35 illustrates the state of the subject and the motion information collecting circuitry 10 at the time "t0". The drawing in the lower half of FIG. 35 illustrates the state of the subject and the motion information collecting circuitry 10 at the time "t1". For example, as illustrated in the upper half of FIG. 35, the analyzing circuitry 1410 calculates a relative position (apparent coordinates corresponding to the sensor in the drawing) of a predetermined site of the subject relative to the motion information collecting circuitry 10, on the basis of skeleton information at the walking start time "t0". In one example, as illustrated in the upper half of FIG. 35, the analyzing circuitry 1410 calculates: a relative position "Z_t0 (2$c$)=3.0 m" of the joint "2$c$" corresponding to the lumbar of the subject relative to the motion information collecting circuitry 10; a relative position "Z_t0(2$s$)=2.9 m" of the joint "2$s$" corresponding to the left ankle relative to the motion information collecting circuitry 10; and a relative position "Z_t0(2$o$)=3.1 m" of the joint "2$o$" corresponding to the right ankle relative to the motion information collecting circuitry 10.

After that, as illustrated in the lower half of FIG. 35, on the basis of the skeleton information at the time "t1", the analyzing circuitry 1410 calculates: a relative position "Z_t1 (2$c$)=3.1 m" of the joint "2$c$" corresponding to the lumbar of the subject relative to the motion information collecting circuitry 10; a relative position "Z_t1(2$s$)=3.2 m" of the joint "2$s$" corresponding to the left ankle relative to the motion information collecting circuitry 10; and a relative position "Z_t1(2$o$)=2.9 m" of the joint "2$o$" corresponding to the right ankle relative to the motion information collecting circuitry 10.

Subsequently, the analyzing circuitry 1410 reads the moving distance corresponding to "t1" from the moving distance storage circuitry 1307 and calculates the position of the subject with respect to the floor, on the basis of the information about the calculated relative positions of the sites and the moving distance of the motion information collecting circuitry 10. For example, the analyzing circuitry 1410 reads the moving distance "A=2.5" of the motion information collecting circuitry 10 (the sensor illustrated in FIG. 35) at "t1" and calculates the position of the subject with respect to the floor in the manner described below.

For example, the analyzing circuitry 1410 calculates the position of the subject with respect to the floor, by adding the moving distance of the motion information collecting circuitry 10 to the difference between the relative positions of the subject before and after the spatial move. In one example, for the joint "2$c$" corresponding to the lumbar described above, the analyzing circuitry 1410 calculates the position of the z coordinate of the joint "2$c$" as "B_t1(2$c$)=(Z_t0(2$c$)−Z_t1(2$c$))+A=(3.0−3.1)+2.5=2.4 m". In other words, the analyzing circuitry 1410 calculates the value of the z-axis coordinate of the joint "2$c$" of the lumbar of the subject at the point in time "t1" as "2.4 m". In this situation, "2.4 m" corresponds to the distance from the z coordinate position of "2$c$" at the walking start time "t0".

Similarly, also for the joint "2$s$", the analyzing circuitry 1410 calculates the position of the z coordinate as "B_t1 (2$s$)=(Z_t0(2$s$)−Z_t1(2$s$))+A=(2.9−3.2)+2.5=2.2 m". Further, also for the joint "2$o$", the analyzing circuitry 1410 calculates the position of the z coordinate as "B_t1(2$o$)= (Z_t0(2$o$)−Z_t1(2$o$))+A=(3.1−2.9)+2.5=2.7 m".

In this manner, the analyzing circuitry 1410 calculates the coordinates of the different sites of the subject on the same axis as the moving direction of the moving mechanism 30, for each of the frames in which the motion information is acquired. As for the y-axis coordinates, it is possible to use the values acquired by the motion information collecting circuitry 10, regardless of the position of the moving mechanism 30 (the position of the recognition range of the motion information collecting circuitry 10 with respect to the floor). Also, as for the x-axis coordinates, it is possible to use the values acquired by the motion information collecting circuitry 10, as long as the extent of the recognition range in the x-axis direction does not change due to the move of the moving mechanism 30.

Figure 36:
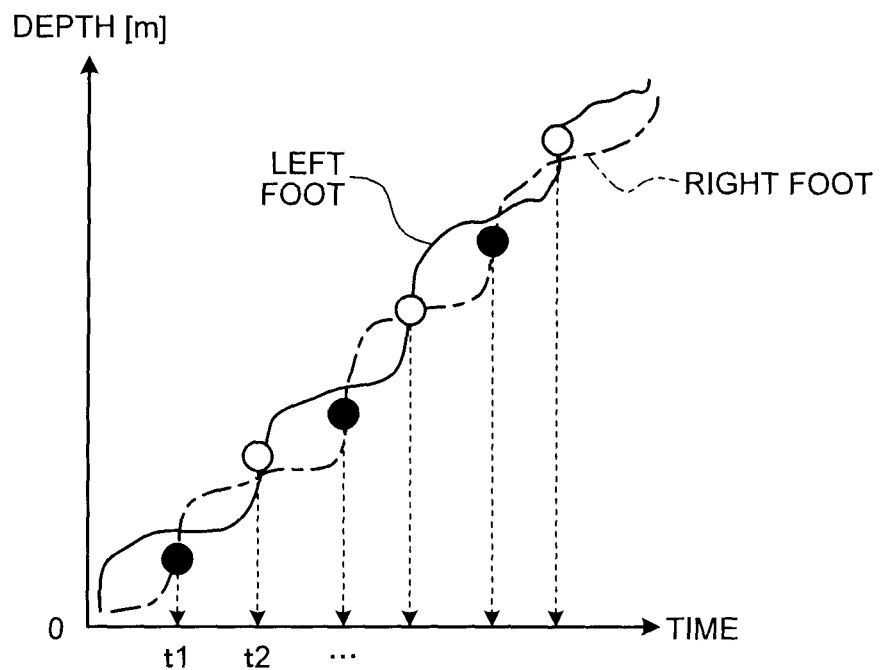
FIG. 36 is a drawing for explaining an example of a walking training analysis performed by the analyzing circuitry according to the eighth embodiment.

After that, the analyzing circuitry 1410 performs an analysis on the spatial move motion of the subject, by using the calculated coordinate information. For example, when the subject performs walking training, the analyzing circuitry 1410 analyzes feet landing points on the basis of changes in the z coordinates of the feet of the subject. FIG. 36 is a drawing for explaining an example of a walking training analysis performed by the analyzing circuitry 1410 according to the eighth embodiment. For example, the analyzing circuitry 1410 calculates the values of the z coordinates of the left and right feet in each of the frames during the walking training of the subject and generates a chart that expresses, for each foot, the depth (m) on the vertical axis and the time on the horizontal axis, as illustrated in FIG. 36.

Further, for the left and right feet in the chart in FIG. 36, the analyzing circuitry 1410 determines that the foot is on the floor at the point in time when the depth exhibits no change in the course of time. In other words, from the chart for the left and right feet illustrated in FIG. 36, the analyzing circuitry 1410 determines that each of the points in time when the change in the z coordinate value per circuitry time period is equal to or smaller than a predetermined threshold value is a point in time when the foot is on the floor, and thus determines the coordinate information of the foot at the determined point in time (the frame) as a landing point of the foot. In this situation, the predetermined threshold value used in the determination process may arbitrarily be set.

The configuration described above is merely an example. The coordinates that can be used are not limited to those described above. In other words, it is acceptable to use not only the z coordinates of the joints "$2s$" and "$2o$", but also the z coordinates of the joints "$2t$" and "$2p$" or the z coordinates of the knees, for example. Further, instead of using a single joint, it is also acceptable to use changes in the z coordinates of two joints, for example, so as to perform the determination process in a comprehensive manner. Further, the analyzing circuitry 1410 is also able to calculate the feet landing points, by using not only the z coordinates, but also y coordinates or x coordinates, for example.

In one example, when using y coordinates, the analyzing circuitry 1410 judges whether each of the feet is on the ground or not, on the basis of the y coordinate value of each of different joints (the height of each of the joints). In other words, if the y coordinate value of each of the joints is equal to or smaller than a predetermined threshold value, the analyzing circuitry 1410 determines that the foot is on the ground. The predetermined threshold value may arbitrarily be set for each joint. In another example, when using x coordinates, the analyzing circuitry 1410 determines that each of the feet is on the ground when the x coordinate value is substantially constant. In other words, while the subject is walking, the x coordinate values of joints in the foot on the ground hardly change. On the contrary, for the foot that is in the air, the x coordinate values fluctuate by small amounts. For this reason, when the x coordinate values are substantially constant, the analyzing circuitry 1410 determines that the foot is on the ground.

Further, with regard to the coordinates, it is also acceptable to perform the determination process by using a plurality of coordinate values in a comprehensive manner. For example, it is acceptable to analyze changes in the z coordinate and changes in the y coordinate and to determine whether each of the feet is on the ground or not on the basis of the result of each of the analyses. Further, it is also acceptable to add a predetermined coefficient to each of the coordinate values. For example, it is acceptable to perform the determination process by adding a coefficient "$\alpha$" to the y coordinate value.

Further, as explained above, the analyzing circuitry 1410 is capable of determining not only that each of the feet is on the ground, but also that each of the feet is in the air. For example, the analyzing circuitry 1410 determines that each of the feet is in the air when a change in the z coordinate value per unit time period exceeds a predetermined threshold value. Alternatively, for example, the analyzing circuitry 1410 determines that each of the feet is in the air when the y coordinate value exceeds a predetermined threshold value. Alternatively, for example, the analyzing circuitry 1410 determines that each of the feet is in the air when the x coordinate value fluctuates by small amounts. Further, the analyzing circuitry 1410 determines that the other foot that is different from the foot determined to be in the air is on the ground. For example, while the right foot is in the air during a walk, the analyzing circuitry 1410 is able to determine that the left foot is on the ground. Alternatively, by inputting the coordinates of the ground into a system in advance, the analyzing circuitry 1410 is also able to determine that each of the feet is on the ground when the foot is positioned close to the coordinates of the ground.

The analyzing circuitry 1410 analyzes the positions (the coordinates) of the feet landing points in the manner described above. Accordingly, for example, on the basis of the positions of the feet landing points resulting from the analysis, the analyzing circuitry 1410 analyzes a stride distance, step lengths, step widths, the number of steps, a cadence value, a walking time period, the time periods when each of the feet is on the ground, and the like. In other words, the analyzing circuitry 1410 analyzes the various types of information listed above, by using the coordinates of the feet landing points. In this situation, the analyzing circuitry 1410 is able to calculate the stride distance, the step lengths, the step widths, and the like while using the walking direction as a reference. In this situation, the "stride distance" is information indicating the distance between where one foot landed and where the same foot landed again. The "step length" is information indicating the distance in the advancing direction from the landing point of the right foot (or the left foot) to the landing point of the left foot (or the right foot) during a walk of the subject. The "step width" is information indicating the distance in the direction orthogonal to the advancing direction from the landing point of the right foot (or the left foot) to the landing point of the left foot (or the right foot) during a walk of the subject. The "number of steps" is information indicating the number of steps taken by the subject during walking training. The "cadence value" is information indicating the number of steps per unit time period.

Further, the analyzing circuitry 1410 is also capable of analyzing angles, by using the positions (the coordinates) of different sites of the subject with respect to the floor. For example, by using the coordinates of different sites of the subject with respect to the floor for each of the frames, the analyzing circuitry 1410 may calculate the angle of a predetermined site of the body of the subject with respect to a predetermined reference element. For example, when a subject performs walking training in the direction of the arrow along the z-axis direction in a predetermined space in the global coordinate system (a space in which the motion information collecting circuitry 10 is able to acquire the coordinate information) illustrated in FIG. 33, the analyzing circuitry 1410 is capable of calculating various angles.

For example, the analyzing circuitry 1410 calculates the angle of an axis (the body axis) from the joint "$2a$" corresponding to the head to the joint "$2d$" corresponding to a center part of the buttocks, with respect to the vertical direction on an x-y plane. In that situation, the analyzing circuitry 1410 calculates a straight line passing through the coordinate information of the joint "$2a$" corresponding to the head and the coordinate information of the joint "$2d$" corresponding to the center part of the buttocks in a predetermined frame and further calculates the angle formed by the calculated straight line and a straight line parallel to the y-axis. In other words, the analyzing circuitry 1410 calculates the degree of the angle to the left/right (the angle to the subject's left/right) as the subject is viewed from the front.

As another example, the analyzing circuitry 1410 calculates the angle of an axis from the joint "2e" corresponding to the right shoulder to the joint "2i" corresponding to the left shoulder, with respect to the horizontal direction on an x-z plane. In that situation, the analyzing circuitry 1410 calculates a straight line passing through the coordinate information of the joint "2e" corresponding to the right shoulder and the coordinate information of the joint "2i" corresponding to the left shoulder in a predetermined frame and further calculates the angle formed by the calculated straight line and a straight line parallel to the x-axis. In other words, the analyzing circuitry 1410 calculates the degree of a misalignment of the body in the rotation direction centered on the body axis, as the subject is viewed from above.

As yet another example, the analyzing circuitry 1410 calculates the angle of an axis (the body axis) from the joint "2a" corresponding to the head to the joint "2d" corresponding to a center part of the buttocks, with respect to the vertical direction on a y-z plane. In that situation, the analyzing circuitry 1410 calculates a straight line passing through the coordinate information of the joint "2a" corresponding to the head and the coordinate information of the joint "2d" corresponding to the center part of the buttocks in a predetermined frame and further calculates the angle formed by the calculated straight line and a straight line parallel to the y-axis. In other words, the analyzing circuitry 1410 calculates the degree of the angle to the left/right (the angle to the subject's front/back), as the subject is viewed from a side.

Alternatively, the analyzing circuitry 1410 may also use a part of the body of the subject as the predetermined reference element. More specifically, the analyzing circuitry 1410 calculates the angle of a predetermined site of the body of the subject with respect to a part of the body of the subject, by using positions of different sites of the subject with respect to the floor calculated for each of the frames. For example, when a subject performs walking training in the direction of the arrow along the z-axis direction in a predetermined space in the global coordinate system (a space in which the motion information collecting circuitry 10 is able to acquire the coordinate information) as illustrated in FIG. 33, the analyzing circuitry 1410 calculates the angle of the bone connecting the joint "2f" corresponding to the right elbow to the joint "2g" corresponding to the right wrist, with respect to the bone connecting the joint "2e" corresponding to the right shoulder to the joint "2f" corresponding to the right elbow. In other words, the analyzing circuitry 1410 analyzes the angle of the right arm (the right elbow) of the subject during the walking motion. In that situation, the analyzing circuitry 1410 calculates a straight line passing through the coordinate information of the joint "2e" and the coordinate information of the joint "2f" in a predetermined frame. The analyzing circuitry 1410 further calculates a straight line passing through the coordinate information of the joint "2f" and the coordinate information of the joint "2g". After that, the analyzing circuitry 1410 calculates the angle formed by the two calculated straight lines.

Further, the analyzing circuitry 1410 is also capable of analyzing velocities at different sites of the subject. For example, to analyze the velocities, the analyzing circuitry 1410 calculates a moving distance [m] by which the coordinates of a predetermined site of the subject has moved with respect to the floor, once every predetermined time period (e.g., 0.5 seconds). After that, the analyzing circuitry 1410 calculates the moving velocity [m/sec] of the subject for each predetermined time period, on the basis of the calculated moving distance per predetermined time period. In this situation, the analyzing circuitry 1410 may also calculate an average value of moving velocities of the subject during the walking training as a walking speed of the subject. In one example, the analyzing circuitry 1410 calculates a moving velocity of a site (e.g., one of the joints or a site of the body derived from joints) designated by the operator via the input circuitry 120. Further, the analyzing circuitry 1410 calculates an acceleration by using the calculated velocity. More specifically, the analyzing circuitry 1410 calculates the acceleration (the ratio of changes in the velocity per unit time period), by using the velocity per unit time period calculated by using the method described above.

As explained above, the analyzing circuitry 1410 performs the various types of analyses by using the coordinate information of the sites of the subject with respect to the floor for each of the frames. In this situation, the analyzing circuitry 1410 may perform the analyses described above automatically or may perform the analyses according to operations of the operator. Further, by using the analysis results, the analyzing circuitry 1410 is also capable of judging whether the walk of the subject is a walk that satisfies a predetermined criterion (a stable walk). Further, as an analysis performed according to an operation of the operator, the analyzing circuitry 1410 is also capable of measuring a distance or the like.

Returning to the description of FIG. 32, the display controlling circuitry 1411 is configured to cause the output circuitry 110 to output the information acquired by the motion information collecting circuitry 10, the analysis results obtained by the analyzing circuitry 1410, and the like. For example, the display controlling circuitry 1411 causes the output circuitry 110 to output the color image information acquired by the motion information collecting circuitry 10, the analysis result from the analysis performed on the walking training by the analyzing circuitry 1410, and the like.

Figure 37:
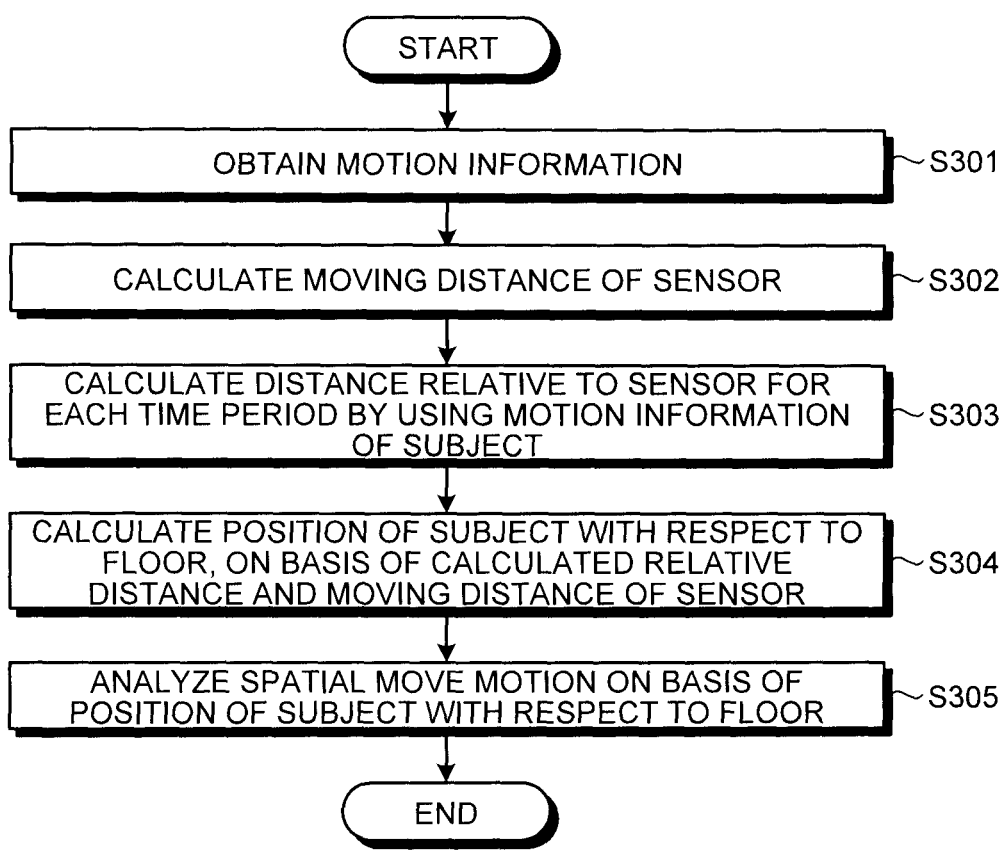
FIG. 37 is a flowchart of a procedure in a process performed by the motion information processing apparatus according to the eighth embodiment.

Next, a process performed by the motion information processing apparatus 100b according to the eighth embodiment will be explained with reference to FIG. 37. FIG. 37 is a flowchart of a procedure in the process performed by the motion information processing apparatus 100b according to the eighth embodiment.

As illustrated in FIG. 37, in the motion information processing apparatus 100b according to the eighth embodiment, when a spatial move motion is started, the obtaining circuitry 1408 obtains motion information of the subject performing the spatial move motion, from a sensor (step S301). In other words, the obtaining circuitry 1408 obtains the motion information acquired by the sensor serving as the motion information collecting circuitry 10, from the motion information storage circuitry 1306.

After that, the analyzing circuitry 1410 calculates a moving distance of the sensor (step S302) and calculates a relative distance relative to the sensor for each of the time periods (for each of the frames) by using the motion information of the subject (step S303). Subsequently, the analyzing circuitry 1410 calculates the position of the subject with respect to the floor, on the basis of the calculated relative distance and the calculated moving distance of the sensor (step S304).

After that, the analyzing circuitry 1410 analyzes the motion information on the basis of the position of the subject with respect to the floor for each of the frames (step S305). For example, the analyzing circuitry 1410 performs various types of analyses on the walking motion of the subject performing the walking training.

As explained above, according to the eighth embodiment, the obtaining circuitry 1408 obtains the motion information of the subject acquired from the predetermined position with respect to the subject performing the spatial move motion. The analyzing circuitry 1410 analyzes the spatial move motion of the subject, on the basis of the motion information obtained by the obtaining circuitry 1408. Accordingly, the motion information processing apparatus 100b according to the eighth embodiment is able to obtain the motion information from the predetermined position, at all times, with respect to the subject performing the spatial move motion. The motion information processing apparatus 100b thus makes it possible to provide the subject performing the spatial move motion with a stable aid. As a result, the motion information processing apparatus 100b according to the eighth embodiment enables medical doctors, physiotherapists, and the like to evaluate the rehabilitation with a higher level of precision.

Further, according to the eighth embodiment, the obtaining circuitry 1408 obtains the motion information of the subject acquired by the motion information collecting circuitry 10 of which the position is changed by the moving mechanism 30 in such a manner that the subject performing the spatial move motion is kept inside the recognition range of the motion information collecting circuitry 10 configured to acquire the motion information of the subject. Further, the analyzing circuitry 1410 analyzes the spatial move motion of the subject, on the basis of the motion information that is of the subject performing the spatial move motion and is obtained by the obtaining circuitry 1408 and the change amount in the position of the motion information collecting circuitry 10. Consequently, the motion information processing apparatus 100b according to the eighth embodiment is able to obtain, at all times, the motion information having a high level of precision and thus makes it possible to provide a more stable aid. For example, for walking training, the motion information processing apparatus 100b provide the walking training aiding function that allows the recognition range of the motion information collecting circuitry 10 to be long and has a constant level of precision. The motion information processing apparatus 100b thus makes it possible to evaluate the walking training in a clinically useful manner.

Further, according to the eighth embodiment, the analyzing circuitry 1410 calculates the relative position relative to the motion information collecting circuitry 10 by using the chronological motion information obtained by the obtaining circuitry 1408 and further analyzes the spatial move motion of the subject on the basis of the calculated relative position and the change amount in the position of the motion information collecting circuitry 10. Consequently, the motion information processing apparatus 100b according to the eighth embodiment makes it possible to perform an accurate analysis, even when the position of the motion information collecting circuitry 10 moves.

Further, according to the eighth embodiment, the change amount in the position of the motion information collecting circuitry 10 is calculated from the acceleration of the motion information collecting circuitry 10, from the rotation speed of a wheel or the motor provided for the moving mechanism 30, or by the wireless device provided for the moving mechanism 30. Consequently, the motion information processing apparatus 100b according to the eighth embodiment makes it possible to provide the subject performing the spatial move motion with a stable aid in various situations.

Ninth Embodiment

In the eighth embodiment described above, the example is explained in which the motion information collecting circuitry 10 is placed on the moving mechanism 30, so that the position thereof is moved in accordance with the spatial move of the subject. In a ninth embodiment, an example will be explained in which a subject performing a spatial move motion is aided, without the position of the motion information collecting circuitry 10 being moved. In the ninth embodiment, the moving mechanism 30 and specifics of processes performed by the moving mechanism controlling circuitry 1409 and the analyzing circuitry 1410 are different from those in the eighth embodiment. The ninth embodiment will be explained below while a focus is placed on the different processes.

Figure 38:
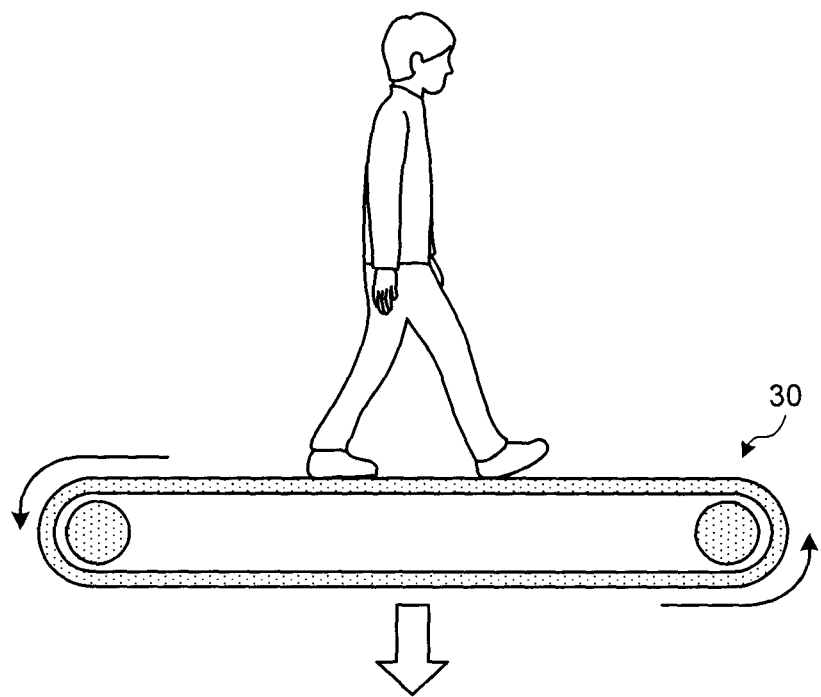
FIG. 38 is a drawing of an example of a moving mechanism according to a ninth embodiment.

FIG. 38 is a drawing of an example of the moving mechanism 30 according to the ninth embodiment. For example, as illustrated in FIG. 38, the moving mechanism 30 according to the ninth embodiment is a moving floor. Further, the moving mechanism controlling circuitry 1409 according to the ninth embodiment is configured to exercise control so as to move the moving mechanism (the moving floor) 30 illustrated in FIG. 38 at a predetermined speed. In other words, the moving mechanism controlling circuitry 1409 causes the floor on which the subject performs a spatial move motion to move at the predetermined speed, by causing the roller illustrated in FIG. 38 to turn at a predetermined speed. In this situation, as for the speed of the floor, it is possible to arrange the floor to move at an arbitrary speed and to adjust the speed to vary in accordance with each subject.

Further, the obtaining circuitry 1408 according to the ninth embodiment is configured to obtain motion information of the subject acquired at a predetermined distance from the subject performing the spatial move motion on the moving mechanism 30 (e.g., the moving floor) configured to cause the subject to perform the spatial move motion within a predetermined region. For example, the motion information collecting circuitry 10 is arranged to be in a predetermined position with respect to the subject performing walking training on the moving floor and is configured to acquire the motion information of the subject so as to store the acquired motion information into the motion information storage circuitry 1306. Further, the obtaining circuitry 1408 is configured to obtain the motion information stored in the motion information storage circuitry 1306.

Further, the analyzing circuitry 1410 according to the ninth embodiment is configured to analyze the spatial move motion of the subject, on the basis of the motion information that is of the subject performing the spatial move motion and is obtained by the obtaining circuitry 1408 and a moving amount of the moving floor. For example, as illustrated in FIG. 38, the analyzing circuitry 1410 calculates a moving distance A of the floor, on the basis of the rotation speed of the roller of the moving mechanism (the moving floor) 30. After that, the analyzing circuitry 1410 calculates, in the same manner as in the eighth embodiment, the position of the subject, by using the coordinate information of the subject in each of the frames and the calculated moving distance A. In other words, the analyzing circuitry 1410 calculates the coordinates of the subject in the global coordinate system, like the position of the subject with respect to the floor while the subject is performing walking training on an actual floor.

Further, by using the calculated coordinates of the subject in the global coordinate system, the analyzing circuitry 1410 performs various types of analyses on the spatial move motion, as described above. In other words, the analyzing circuitry 1410 performs an analysis on the walking and an analysis on the angles, the velocities, or the like of the subject.

As explained above, according to the ninth embodiment, the obtaining circuitry 1408 obtains the motion information of the subject acquired at the predetermined distance from the subject performing the spatial move motion on the moving mechanism (e.g., the moving floor) 30 configured to cause the subject to perform the spatial move motion within the predetermined region. Consequently, the motion information processing apparatus 100b according to the ninth embodiment makes it possible to obtain the motion information of the subject performing the spatial move motion in the limited space with a high level of precision.

Further, according to the ninth embodiment, the obtaining circuitry 1408 obtains the motion information of the subject performing the spatial move motion on the moving floor. Further, the analyzing circuitry 1410 analyzes the spatial move motion of the subject, on the basis of the motion information that is of the subject performing the spatial move motion and is obtained by the obtaining circuitry 1408 and the moving amount of the moving floor. Consequently, the motion information processing apparatus 100b according to the ninth embodiment makes it possible to easily perform the spatial move motion in the limited space.

Tenth Embodiment

The eighth and the ninth embodiments have thus been explained. The present disclosure, however, may be carried out in other various embodiments besides the eighth and the ninth embodiments described above.

In the eighth embodiment described above, the example is explained in which the moving mechanism 30 on which the motion information collecting circuitry 10 is placed moves in front of the subject; however, possible embodiments are not limited to this example. For instance, the moving mechanism 30 may move alongside the subject. In that situation, for example, the subject performing the walking training walks along the x-axis in the recognition range of the motion information collecting circuitry 10. Consequently, for example, the moving mechanism controlling circuitry 1409 controls the moving mechanism 30 in such a manner that the position of the center of the subject (e.g., the joint "2c" corresponding to the lumbar) is positioned at "0" on the x-axis (positioned at the center, in the x-axis direction, of the recognition range). Further, the analyzing circuitry 1410 calculates a moving distance of the moving mechanism 30. After that, the analyzing circuitry 1410 calculates the deviation of the subject from the "0" on the x-axis for each of the frames and further calculates the position (the coordinates) of the subject with respect to the floor, by using the deviations in two frames at mutually-different points in time and the moving distance.

In the eighth embodiment described above, the example is explained in which the moving mechanism 30 moves on a flat surface so that no shaking or the like is caused; however, possible embodiments are not limited to this example. For instance, the present disclosure is applicable even if the moving mechanism 30 moves on an uneven surface and shaking is caused. For example, if the moving mechanism 30 moves on an uneven surface having a small obstacle or the like or if shaking is caused due to the travelling of its own, the coordinates serving as the motion information may be shifted around on all axes. To cope with this situation, the motion information processing apparatus 100b according to a tenth embodiment is configured to eliminate or to fine-tune the shifts of the axes caused by the use of the moving mechanism 30.

More specifically, the analyzing circuitry 1410 according to the tenth embodiment calculates the shifts of the coordinates of the moving mechanism 30 during the move, on the basis of the coordinates of a reference position and further corrects the coordinates of the motion information on the basis of the calculated shifts. For example, by using the coordinates of a certain position at the start of the traveling of the moving mechanism 30 for a walking motion as a reference point, the analyzing circuitry 1410 calculates the shift of the coordinates of the position at each of the points in time when the motion information is acquired. In other words, the analyzing circuitry 1410 calculates the shift of the coordinates at each of the points in time, on the basis of the direction and the velocity in which and at which the moving mechanism 30 has moved since the start of the traveling. After that, on the basis of the calculated shifts, the analyzing circuitry 1410 corrects the coordinates of the acquired motion information. With this arrangement, it is possible to acquire the motion information having a higher level of precision.

In the eighth embodiment described above, the example is explained in which the motion information processing apparatus 100b analyzes the spatial move motion by obtaining the motion information of the subject performing the spatial move motion; however, possible embodiments are not limited to this example. For instance, the processes may be performed by a service providing apparatus connected to a network.

Figure 39:
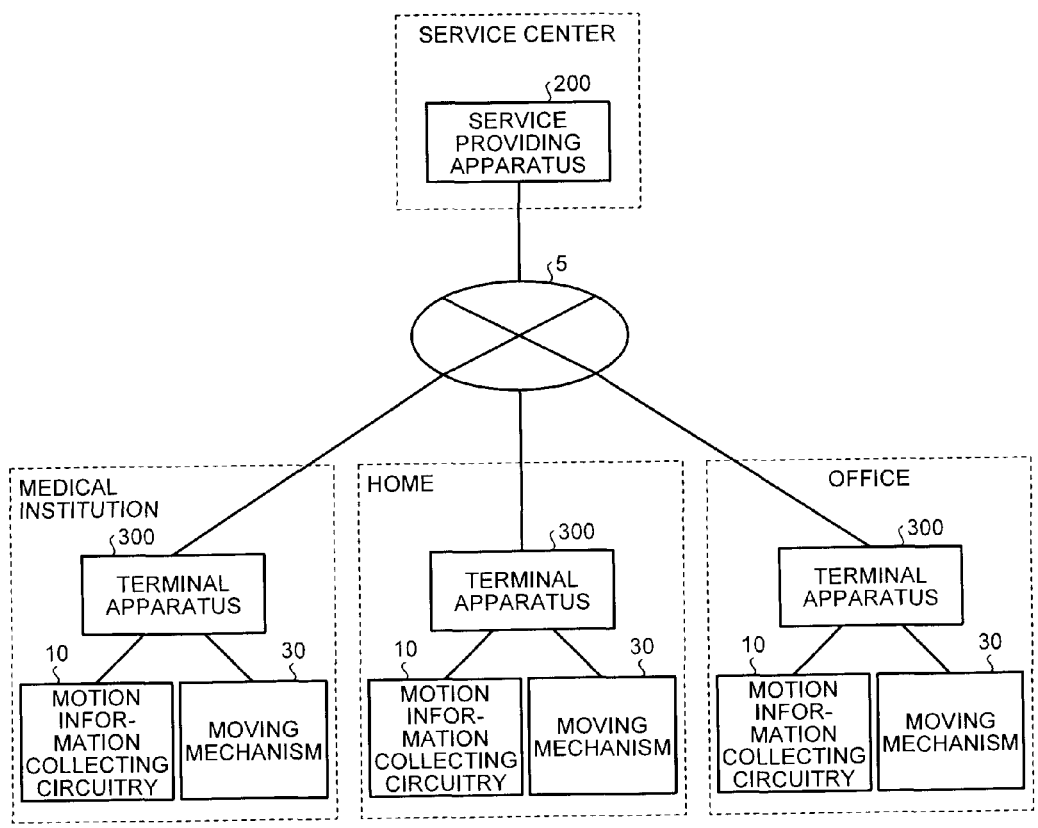
FIG. 39 is a diagram for explaining an example in which an aspect of the present disclosure is applied to a service providing apparatus according to a tenth embodiment.

FIG. 39 is a diagram for explaining an example in which an aspect of the present disclosure is applied to a service providing apparatus according to the tenth embodiment. As illustrated in FIG. 39, the service providing apparatus 200 is provided in a service center and is connected to, for example, the terminal apparatuses 300 that are provided in a medical institution, a home, and an office, via the network 5. To each of the terminal apparatuses 300 provided at the medical institution, the home, and the office, at least one motion information collecting circuitry 10 and at least one moving mechanism 30 are connected. Further, each of the terminal apparatuses 300 has a client function used for utilizing services provided by the service providing apparatus 200.

The service providing apparatus 200 is configured to provide, as the services, each of the terminal apparatuses 300 with the same processes as those of the motion information processing apparatus 100b. In other words, the service providing apparatus 200 includes functional circuitry that are equivalent to the obtaining circuitry 1408 and the analyzing circuitry 1410. Further, the functional circuitry equivalent to the obtaining circuitry 1408 is configured to obtain the motion information of a subject acquired from a predetermined position with respect to the subject performing a spatial move motion. Further, the functional circuitry equivalent to the analyzing circuitry 1410 is configured to analyze the spatial move motion of the subject on the basis of the motion information obtained by the functional circuitry equivalent to the obtaining circuitry 1408. The network 5 may be wired or wireless and may be configured with an arbitrary type of communication network such as the Internet, a Wide Area Network (WAN), or the like.

The configuration of the motion information processing apparatus 100b according to the eighth embodiment described above is merely an example, and it is possible to integrate together or separate any of the functional circuitry, as appropriate. For example, it is possible to integrate the motion information storage circuitry 1306 and the moving distance storage circuitry 1307 together. It is also possible to separate the analyzing circuitry 1410 into a calculating circuitry configured to calculate the moving distance and a motion information analyzing circuitry configured to analyze the spatial move motion.

Further, the functions of the obtaining circuitry 1408, the moving mechanism controlling circuitry 1409, the analyzing circuitry 1410, and the display controlling circuitry 1411 described in the eighth to the tenth embodiments may be realized by software. For example, the functions of the obtaining circuitry 1408, the moving mechanism controlling circuitry 1402, the analyzing circuitry 1410, and the display controlling circuitry 1411 may be realized by causing a computer to execute a medical information processing program that defines the procedure of the processes described as being performed by the obtaining circuitry 1408, the moving mechanism controlling circuitry 1409, the analyzing circuitry 1410, and the display controlling circuitry 1411 in the embodiments above. For example, the medical information processing program is stored in a hard disk, a semiconductor memory device, or the like so as to be read and executed by a processor such as a CPU, an MPU, or the like. Further, the medical information processing program may be distributed as being recorded on a computer-readable recording medium such as a Compact Disk Read-Only Memory (CD-ROM), a Magnetic Optical (MO) disk, a Digital Versatile Disk (DVD), or the like.

Eleventh Embodiment

The first to the tenth embodiments have thus been explained. The present disclosure, however, may be carried out in other various embodiments besides the first to the tenth embodiments described above. For example, among the first to the tenth embodiments described above, the first to the fourth embodiments refer to the motion information processing apparatus configured to obtain the detailed information about the motions of the subject undergoing the rehabilitation. The fifth to the seventh embodiments refer to the motion information processing apparatus configured to obtain the precise information of the subject undergoing the rehabilitation. The eighth to the tenth embodiments refer to the motion information processing apparatus configured to provide the subject performing the spatial move motion with the stable aid. The motion information processing apparatus according to the present disclosure, however, is capable of realizing any of the configurations and the processes described in these embodiments in an arbitrary combination.

For example, it is possible to provide viewers with a single piece of display information in which a plurality of pieces of motion information are kept in synchronization with one another, together with the subject information kept in synchronization with the pieces of motion information. In that situation, for example, the motion information processing apparatus has the plurality of motion information collecting circuitry connected thereto, as illustrated in FIG. 1, and further has the subject information collecting circuitry connected thereto, as illustrated in FIG. 20. Further, the motion information collecting circuitry include the functional circuitry illustrated in FIG. 5 and the functional circuitry illustrated in FIG. 22, so as to generate and display the display information in which the plurality of pieces of motion information are kept in correspondence with the subject information. In other words, in the motion information processing apparatus, a position calculating circuitry included therein is configured to bring the pieces of motion information generated by the plurality of motion information collecting circuitry into synchronization with one another, and further, a display information generating circuitry included in the apparatus is configured to generate the display information in which the motion information and the subject information are kept in association (synchronization) with each other and to cause a display circuitry to display the generated display information. Further, the motion information processing apparatus described above is also able to generate and display such display information in which an analysis result obtained by an analyzing circuitry included in the apparatus is further kept in association (synchronization) therewith.

Further, for example, a motion information processing apparatus is also able to bring a plurality of pieces of motion information into synchronization with one another, while a plurality of motion information collecting circuitry are configured to be moved by moving mechanisms. In that situation, for example, the motion information processing apparatus has the plurality of motion information collecting circuitry connected thereto as illustrated in FIG. 1 and further has the moving mechanisms connected thereto as illustrated in FIG. 31. Further, the motion information collecting circuitry include the functional circuitry illustrated in FIG. 5 and the functional circuitry illustrated in FIG. 32, so as to generate and display such display information in which the pieces of motion information generated by the plurality of motion information collecting circuitry moved by the moving mechanisms are kept in synchronization with one another. In other words, in the motion information processing apparatus, a moving mechanism controlling circuitry included therein is configured to control the plurality of moving mechanisms in such a manner that the distance between each of the plurality of motion information collecting circuitry and the subject is constant, and also, a position calculating circuitry included in the apparatus is configured to generate such display information in which the pieces of motion information generated by the plurality of motion information collecting circuitry are kept in synchronization with one another, so that the display circuitry displays the generated display information.

Further, for example, a motion information processing apparatus is also able to generate and display such display information in which the pieces of motion information generated by the motion information collecting circuitry moved by the moving mechanism are kept in association (synchronization) with the subject information. In that situation, for example, the motion information processing apparatus has the motion information collecting circuitry and the subject information collecting circuitry connected thereto, as illustrated in FIG. 20, and further has the moving mechanism connected thereto as illustrated in FIG. 31. Further, the motion information collecting circuitry includes the functional circuitry illustrated in FIG. 20 and the functional circuitry illustrated in FIG. 32, so as to generate and display the display information in which the pieces of motion information generated by the motion information collecting circuitry moved by the moving mechanism are kept in association (synchronization) with the subject information. In other words, in the motion information processing apparatus, the moving mechanism controlling circuitry included therein is configured to control the moving mechanism in such a manner that the distance between the motion information collecting circuitry and the subject is constant, and also, a display information generating circuitry included in the apparatus is configured to generate the display information in which the motion information and the subject information are kept in association (synchronization) with each other, so that the generated display information is displayed on the display circuitry.

Further, for example, a motion information processing apparatus is able to generate and display such display information in which a plurality of pieces of motion information generated by a plurality of motion information collecting circuitry moved by a plurality of moving mechanisms are kept in association with one another, and also, the subject information is further kept in association (synchronization) therewith. In that situation, for example, the motion information processing apparatus has the plurality of motion information collecting circuitry, the subject information collecting circuitry, and the plurality of moving mechanisms connected thereto and includes the functional circuitry illustrated in FIGS. 5, 22, and 32. The motion information processing apparatus is configured to generate and display the display information in which the plurality of pieces of motion information generated by the motion information collecting circuitry moved by the moving mechanisms are kept in synchronization with one another, while the subject information is further kept in association (synchronization) therewith. The motion information processing apparatus according to the present disclosure is able to use any other configurations and processes in various combinations, in addition to the combinations of configurations and processes described above.

The rehabilitation referred to in the first to the tenth embodiments described above does not necessarily have to be rehabilitation defined by the Japanese Orthopaedic Association or the like and may be rehabilitation defined by any of other various organizations. For example, the rehabilitation may refer to one defined by any of the following: International Society of Orthopaedic Surgery and Traumatology (SICOT); American Academy of Orthopaedic Surgeons (AAOS); European Orthopaedic Research Society (EORS); International Society of Physical and Rehabilitation Medicine (ISPRM); and American Academy of Physical Medicine and Rehabilitation (AAPM & R).

As explained above, according to at least one aspect of the first to the eleventh embodiments, the motion information processing apparatus of the present disclosure makes it possible to provide subjects undergoing rehabilitation with the effective aids.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A motion information processing apparatus, comprising:
processing circuitry configured to
obtain first motion information of a subject performing a predetermined motion acquired by a first sensor and second motion information of the subject performing the predetermined motion acquired by a second sensor arranged at a position different from a position of the first sensor,
calculate association information for synchronizing the obtained first motion information and the obtained second motion information based on information included in each of the first motion information and the second motion information, and
generate output information by synchronizing the first motion information and the second motion information based on the calculated association information, and exercise control so as to cause output circuitry to output the output information.

2. The motion information processing apparatus according to claim 1, wherein the processing circuitry is further configured to calculate the association information based on a predetermined position included in each of the obtained first motion information and the obtained second motion information.

3. The motion information processing apparatus according to claim 2, wherein the processing circuitry is further configured to calculate the association information by using either a relative relationship or absolute values of the predetermined position included in each of the obtained first motion information and the obtained second motion information.

4. The motion information processing apparatus according to claim 2, wherein the processing circuitry is further configured to calculate, as the association information, a positional relationship between the positions from which the first motion information and the second motion information are acquired, by comparing movement of the predetermined position with one another, the predetermined position being included in each of the obtained first motion information and the obtained second motion information.

5. The motion information processing apparatus according to claim 4, wherein the processing circuitry is further configured to exercise control so that, on a display screen of the output circuitry, display information is output in which images rendered by the first motion information and the second motion information are arranged in either positions corresponding to the calculated positional relationship or positions that are set in advance and from which the first motion information and the second motion information are acquired.

6. The motion information processing apparatus according to claim 2, wherein the processing circuitry is further configured to
receive a designating operation to designate the predetermined position included in each of the first motion information and the second motion information, and
calculate the association information based on the predetermined position received.

7. The motion information processing apparatus according to claim 1, wherein the processing circuitry is further configured to change display information used when the first motion information and the second motion information are displayed, in accordance with a movement of the subject included in the first motion information and the second motion information.

8. The motion information processing apparatus according to claim 7, wherein the processing circuitry is further configured to cause the display information to be displayed so as to be varied in accordance with the first and second motion information of the subject, which is acquired from the subject performing a walking motion.

9. The motion information processing apparatus according to claim 1, wherein the processing circuitry is further configured to obtain the first motion information and the second motion information of the subject acquired by the first sensor and the second sensor arranged along an advancing direction of a walk of the subject.

10. The motion information processing apparatus according to claim 9, wherein the processing circuitry is further configured to obtain the first motion information and the second motion information of the subject acquired from the plurality of positions in one of a direction that is parallel to the advancing direction of the subject, a direction that forms a predetermined angle with the advancing direction, and a direction that is orthogonal to the advancing direction.

11. The motion information processing apparatus according to claim 1, wherein the processing circuitry is further configured to obtain the first motion information and the second motion information of the subject acquired by the first sensor and the second sensor so as to be able to acquire a series of motion information during the predetermined motion performed by the subject.

12. The motion information processing apparatus according to claim 1, wherein the processing circuitry is further configured to exercise control so as to cause the output circuitry to output the output information that includes one of the following generated based on at least one of the first motion information and the second motion information of the subject performing a walking motion: locus information indicating a locus of a spatial move of a predetermined site of the subject, velocity information at the predetermined site, and angle information of the predetermined site of the subject.

13. A motion information processing apparatus, comprising:
processing circuitry configured to
obtain first motion information, acquired by a first sensor, of a subject performing a predetermined motion,
obtain second motion information that is of a different type from the first motion information and acquired by a second sensor different from a type of the first sensor,
generate display information by synchronizing the first motion information and the second motion information, and
exercise control so as to cause output circuitry to output the generated display information.

14. The motion information processing apparatus according to claim 13, wherein the processing circuitry is further configured to generate, as the display information, subject information of the subject corresponding to when the subject is performing the predetermined motion.

15. The motion information processing apparatus according to claim 13, wherein the processing circuitry is further configured to
obtain biological information as subject information, and
generate, as the display information, the biological information of the subject corresponding to when the subject is performing the predetermined motion.

16. The motion information processing apparatus according to claim 13, wherein the processing circuitry is further configured to
analyze motions of the subject by using the obtained first and second motion information, and
generate, as the display information, subject information at a point in time when the subject is performing the predetermined motion included in the analyzed motions of the subject.

17. The motion information processing apparatus according to claim 16, wherein the processing circuitry is further configured to
obtain high-precision motion information that has a higher level of precision than the obtained first and second motion information, and
analyze the motions of the subject after correcting the first and second motion information by using the obtained high-precision motion information.

18. The motion information processing apparatus according to claim 16, wherein the processing circuitry is further configured to exercise control so as to cause the output circuitry to display the display information including alert information based on an obtained analysis result obtained.

19. A motion information processing apparatus, comprising: processing circuitry configured to
move a sensor that acquires motion information so that a positional relationship between the sensor and a subject performing a spatial move motion has a predetermined relationship,
obtain the motion information of the subject acquired by the sensor, and
analyze the spatial move motion of the subject based on the obtained motion information,
wherein the processing circuitry is further configured to
change a position of the sensor in such a manner that the subject performing the spatial move motion is inside a recognition range of the sensor that acquires the motion information of the subject,
obtain the motion information of the subject acquired by the sensor, and
analyze the spatial move motion of the subject based on the motion information that is of the subject performing the spatial move motion and a change amount in the position of the sensor.

20. The motion information processing apparatus according to claim 19, wherein the processing circuitry is further configured to calculate a relative position relative to the sensor by using obtained chronological motion information and further analyze the spatial move motion of the subject based on the calculated relative position and the change amount in the position of the sensor.

21. The motion information processing apparatus according to claim 19, wherein the change amount in the position of the sensor is calculated based on a moving velocity of the sensor calculated from an acceleration of the sensor.

22. The motion information processing apparatus according to claim 19, wherein the processing circuitry is further configured to
cause the subject to perform the spatial move motion within a predetermined region, and
obtain the motion information of the subject acquired at a predetermined distance from the subject performing the spatial move motion while using a moving means.

23. The motion information processing apparatus according to claim 22, wherein the processing circuitry is further configured to obtain the motion information of the subject performing the spatial move motion on a moving floor, and analyze the spatial move motion of the subject based on the obtained motion information that is of the subject performing the spatial move motion and a moving amount of the moving floor.

* * * * *